United States Patent
Carninci et al.

(10) Patent No.: US 9,249,457 B2
(45) Date of Patent: Feb. 2, 2016

(54) METHOD OF MANUFACTURING A MIXTURE OF AMPLIFIED DOUBLE-STRANDED NUCLEIC ACIDS COMPRISING UNKNOWN SEQUENCE

(75) Inventors: Piero Carninci, Yokohama (JP); Charles Plessy, Yokohama (JP); Roberto Simone, Yokohama (JP)

(73) Assignee: Riken, Wako-shi (JP)

( * ) Notice: Subject to any disclaimer, the term of this patent is extended or adjusted under 35 U.S.C. 154(b) by 1344 days.

(21) Appl. No.: 12/999,203

(22) PCT Filed: Jun. 18, 2009

(86) PCT No.: PCT/JP2009/061552
§ 371 (c)(1),
(2), (4) Date: Mar. 16, 2011

(87) PCT Pub. No.: WO2009/154303
PCT Pub. Date: Dec. 23, 2009

(65) Prior Publication Data
US 2011/0159505 A1   Jun. 30, 2011

(30) Foreign Application Priority Data
Jun. 18, 2008   (JP) .................................. 2008-159527

(51) Int. Cl.
*C07H 21/02*   (2006.01)
*C12Q 1/68*   (2006.01)
*C12P 19/34*   (2006.01)

(52) U.S. Cl.
CPC .............. *C12Q 1/6848* (2013.01); *C07H 21/02* (2013.01); *C12P 19/34* (2013.01); *C12Q 1/68* (2013.01)

(58) Field of Classification Search
CPC ...................................................... C07H 21/02
USPC ................................ 435/6.12, 91.2; 536/23.1
See application file for complete search history.

(56) References Cited

U.S. PATENT DOCUMENTS

| | | | |
|---|---|---|---|
| 5,759,822 A | 6/1998 | Chenchik et al. | |
| 5,962,272 A | 10/1999 | Chenchik et al. | |
| 6,174,669 B1 | 1/2001 | Hayashizaki et al. | |
| 7,368,265 B2 * | 5/2008 | Brenner et al. | 435/91.2 |
| 7,670,810 B2 * | 3/2010 | Gunderson et al. | 435/91.2 |

FOREIGN PATENT DOCUMENTS

JP   9-511149 A   11/1997

OTHER PUBLICATIONS

Japanese-language Notice of Allowance dated Dec. 17, 2013 (Three (3) pages).
Jannine Brownie, et al., "The elimination of primer-dimer accumulation in PCR", Nucleic Acids Research, Jan. 1, 1997, pp. 3235-3241, vol. 25, No. 16, XP-002152588.
Piero Carninci, et al., "Normalization and Subtraction of Cap-Trapper-Selected cDNAs to Prepare Full-Length cDNA Libraries for Rapid Discovery of New Genes", Genome Research, Cold Spring Harbor Laboratory Press, Jan. 1, 2000, pp. 1617-1630, vol. 10, No. 10, XP-002944079.
Toshiyuki Shiraki, et al., "Cap analysis gene expression for high-throughput analysis of transcriptional starting point and identification of promoter usage", Proceedings of the National Academy of Sciences of USA, National Academy of Science, Dec. 23, 2003, pp. 15776-15781, vol. 100, No. 26, XP-001161070.
International Search Report dated Mar. 3, 2010 and PCT/ISA/237 Form (Eleven (11) pages).
European Office Action dated Feb. 18, 2013 (Five (5) pages).
European Summons to attend oral proceedings dated May 6, 2015 (Four (4) pages).

* cited by examiner

*Primary Examiner* — Ardin Marschel
(74) *Attorney, Agent, or Firm* — Crowell & Moring LLP

(57) ABSTRACT

The purpose of the subject invention is to provide a method of manufacturing a mixture of amplified double-stranded nucleic acids comprising unknown sequence including the complete 5' end sequence.

A method of manufacturing a mixture of amplified double-stranded nucleic acids comprising: (a) preparing a single-stranded nucleic acid comprising a single-stranded adapter 1, a single-stranded nucleic acid fragment and a single-stranded adapter 2, and (b) conducting PCR with said single-stranded nucleic acid prepared in step (a), a primer 1, and a primer 2 to amplify double-stranded nucleic acids.

12 Claims, 36 Drawing Sheets

1st PCR small scale

2nd PCR small scale

Bio Analyzer

| Peak | Size [bp] | Conc. [ng/µl] | Molarity [nmol/l] | Observations |
|------|-----------|---------------|-------------------|--------------|
| 2 | 121 | 2.47 | 30.8 | |

1st PCR small scale

2nd PCR small scale

Before cutting		After cutting

Bio Analyzer

1st PCR small scale

2nd PCR small scale

Before cutting    After cutting

Bio Analyzer

| Peak | Size [bp] | Conc. [ng/µl] | Molarity [nmol/l] | Observations |
|---|---|---|---|---|
| 2 | 121 | 5.07 | 63.4 | |

1st PCR small scale

2nd PCR small scale

Before cutting        After cutting

1st PCR small scale

1st round of 1st PCR large scale

2nd round of 1st PCR large scale

Figure 27
Purification of the tags
Before gel cutting
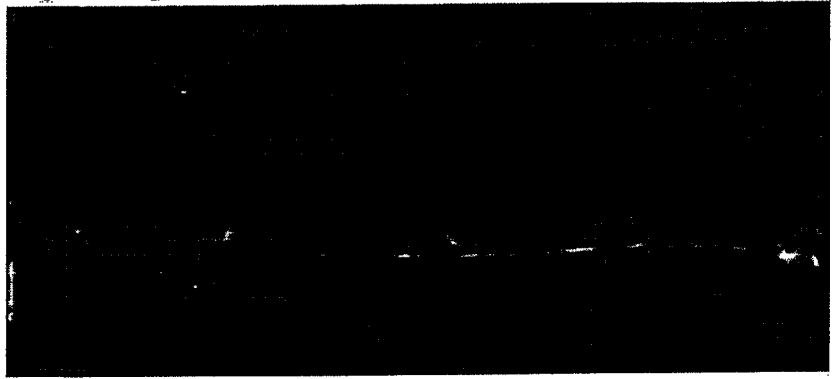
After gel cutting
Figure 28
Result
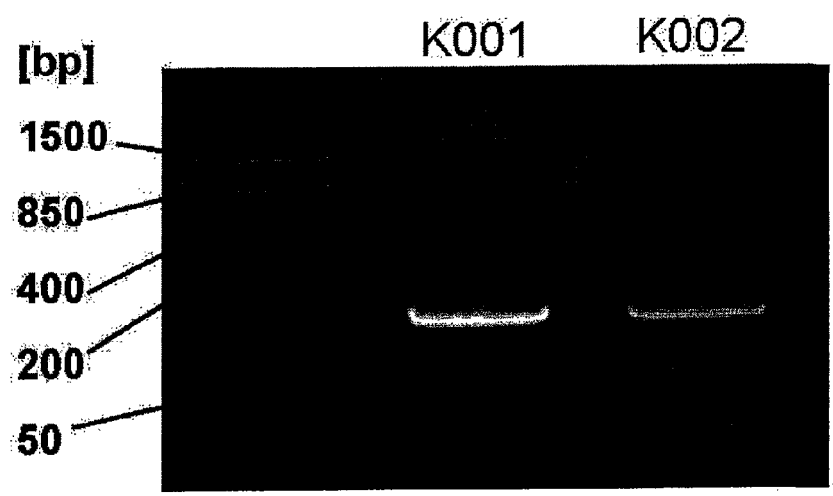

1st PCR small scale

1st round of 1st PCR large scale

Figure 31
2nd round of 1st PCR large scale
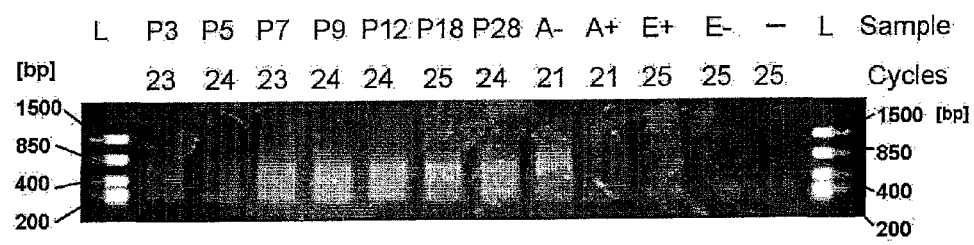
Figure 32
Purification of the 1st round tags
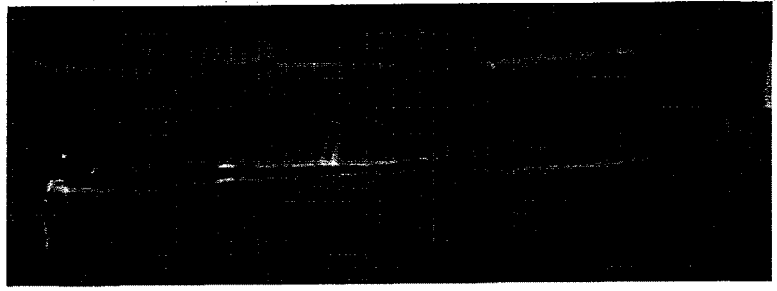

Figure 33
Purification of the 2nd round tags
Before gel cutting
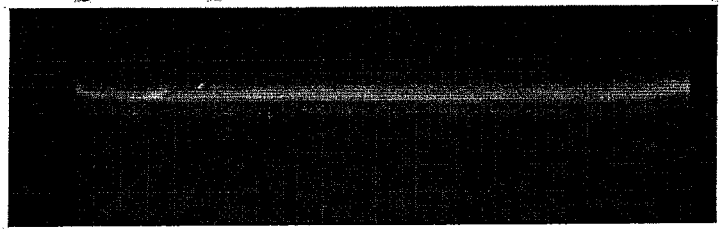
After gel cutting
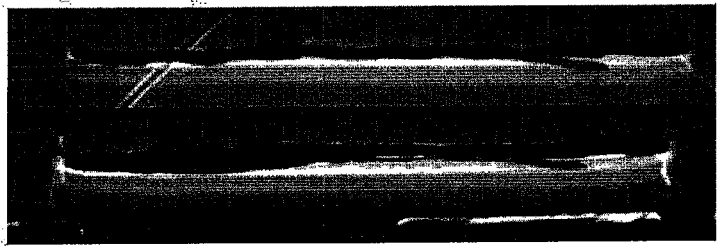
Figure 34
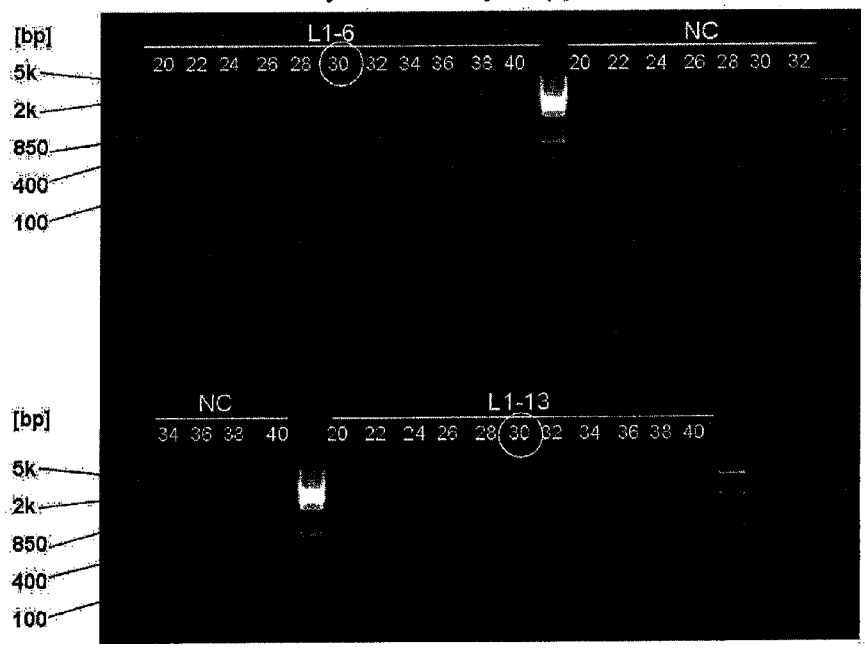

1st PCR small scale

Figure 38
2nd PCR small scale
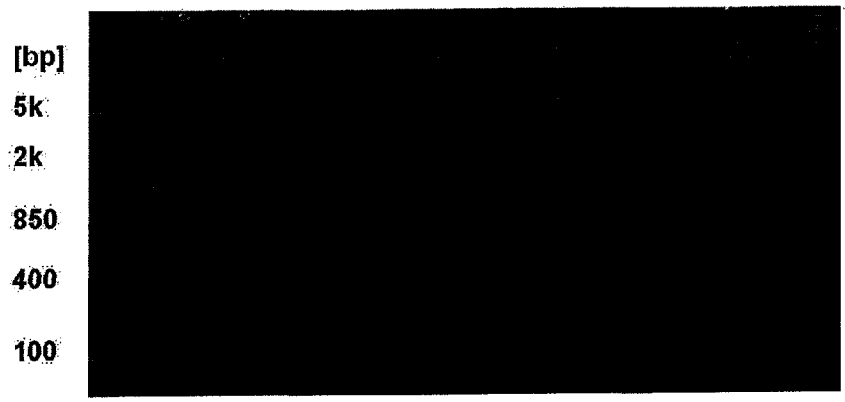
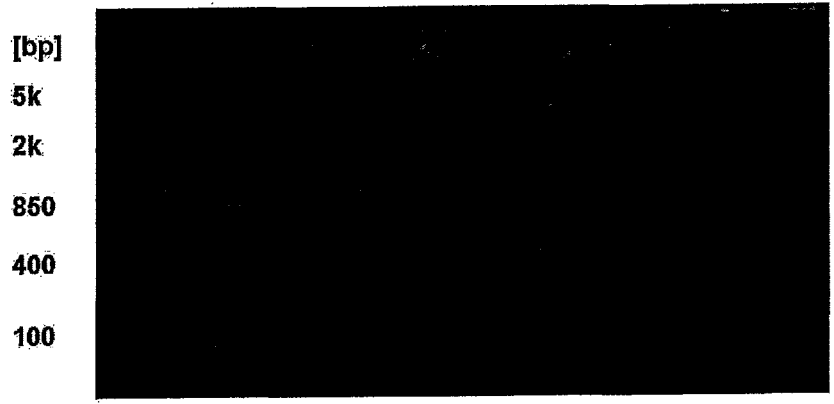

Figure 39
Before cutting
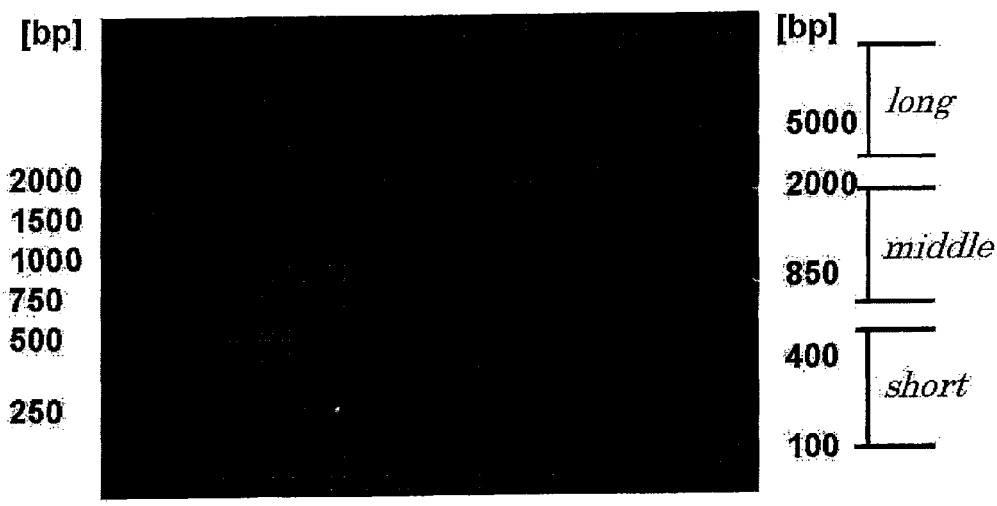
After cutting
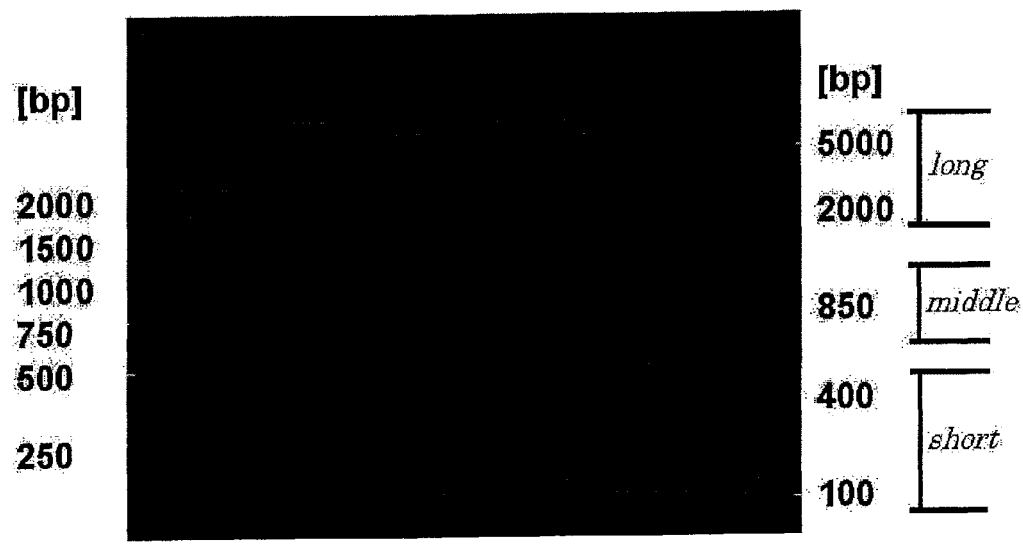

Real-time PCR

1st PCR

1st PCR products (GFX-CTAB) after purification

2$^{nd}$ PCR

2$^{nd}$ PCR products (AMpure) after purification

Figure 45
Deletions and one random permutation (shuffle) of random RT primer

| N-15 | 5'-GTACCAGCAGTAGTCGAACTGAAGGTCTCCTCTNNNNNNNNNNNNNNN-3' |
|---|---|
| N-15-notail | 5'-TAGTCGAACTGAAGGTCTCCTCTNNNNNNNNNNNNNNN-3' |
| N-15-del4 | 5'-GTACCAGCAG CGAACTGAAGGTCTCCTCTNNNNNNNNNNNNNNN-3' |
| N-15-del8 | 5'-GTACCAGCAG CTGAAGGTCTCCTCTNNNNNNNNNNNNNNN-3' |
| N-15-shuffled | 5'-CGTCATACCTCGGCACAATTGCGATATCGGGTANNNNNNNNNNNNNNN-3' |

Reverse PCR primers

| N-15 | 5'-GTACCAGCAGTAGTCGAACTGAAGGTCTCCTCT-3' |
|---|---|
| N-15-notail | 5'-            TAGTCGAACTGAAGGTCTCCTCT-3' |
| N-15-del4 | 5'-GTACCAGCAG    CGAACTGAAGGTCTCCTCT-3' |
| N-15-del8 | 5'-GTACCAGCAG          CTGAAGGTCTCCTCT-3' |
| N-15-shuffled | 5'-CGTCATACCTCGGCACAATTGCGATATCGGGTA-3' |

SEQUENCE LISTING

```
<160> NUMBER OF SEQ ID NOS: 145

<210> SEQ ID NO 1
<211> LENGTH: 27
<212> TYPE: DNA
<213> ORGANISM: Artificial sequence
<220> FEATURE:
<223> OTHER INFORMATION: Nucleic acid fragment

<400> SEQUENCE: 1
tagtcgaact gaaggtctcc agcaggg                                27

<210> SEQ ID NO 2
<211> LENGTH: 48
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (34)..(48)
<223> OTHER INFORMATION: n is a, c, g, or t

<400> SEQUENCE: 2
gtaccagcag tagtcgaact gaaggtctcc tctnnnnnnn nnnnnnnn        48

<210> SEQ ID NO 3
<211> LENGTH: 50
<212> TYPE: DNA
<213> ORGANISM: Artificial sequence
<220> FEATURE:
<223> OTHER INFORMATION: Nucleic acid fragment

<400> SEQUENCE: 3
gtaccagcag tagtcgaact gaaggtctcc tctttttttt tttttttttt      50
```

-continued

```
<210> SEQ ID NO 4
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 4
tagtcgaact gaaggtctcc agc                                             23

<210> SEQ ID NO 5
<211> LENGTH: 33
<212> TYPE: DNA
<213> ORGANISM: Artificial sequence
<220> FEATURE:
<223> OTHER INFORMATION: Nucleic acid fragment

<400> SEQUENCE: 5
gtaccagcag tagtcgaact gaaggtctcc tct                                  33

<210> SEQ ID NO 6
<211> LENGTH: 24
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t

<400> SEQUENCE: 6
nnagctgtag aactctgaac ctgt                                            24

<210> SEQ ID NO 7
<211> LENGTH: 22
<212> TYPE: DNA
<213> ORGANISM: Artificial sequence
<220> FEATURE:
<223> OTHER INFORMATION: Nucleic acid fragment

<400> SEQUENCE: 7
acaggttcag agttctacag ct                                              22

<210> SEQ ID NO 8
<211> LENGTH: 39
<212> TYPE: DNA
<213> ORGANISM: Artificial sequence
<220> FEATURE:
<223> OTHER INFORMATION: Nucleic acid fragment

<400> SEQUENCE: 8
aatgatacgg cgaccaccga caggttcaga gttctacag                            39

<210> SEQ ID NO 9
<211> LENGTH: 43
<212> TYPE: DNA
<213> ORGANISM: Artificial sequence
<220> FEATURE:
<223> OTHER INFORMATION: Nucleic acid fragment

<400> SEQUENCE: 9
caagcagaag acggcatacg atagtcgaac tgaaggtctc cag                       43

<210> SEQ ID NO 10
<211> LENGTH: 25
<212> TYPE: DNA
```

```
<213> ORGANISM: Artificial sequence
<220> FEATURE:
<223> OTHER INFORMATION: Nucleic acid fragment

<400> SEQUENCE: 10
gagtgacgag aggctttgtc cggtt                                            25

<210> SEQ ID NO 11
<211> LENGTH: 27
<212> TYPE: DNA
<213> ORGANISM: Artificial sequence
<220> FEATURE:
<223> OTHER INFORMATION: Nucleic acid fragment

<400> SEQUENCE: 11
tagtcgaact gaaggtctcc agcaggg                                          27

<210> SEQ ID NO 12
<211> LENGTH: 48
<212> TYPE: DNA
<213> ORGANISM: Artificial sequece
<220> FEATURE:
<223> OTHER INFORMATION: Nucleic acid fragment
<220> FEATURE:
<221> NAME/KEY: misc_feature
<222> LOCATION: (34)..(48)
<223> OTHER INFORMATION: n is a, c, g, or t

<400> SEQUENCE: 12
gtaccagcag tagtcgaact gaaggtctcc tctnnnnnnn nnnnnnnn                   48

<210> SEQ ID NO 13
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 13
tagtcgaact gaaggtctcc agc                                              23

<210> SEQ ID NO 14
<211> LENGTH: 33
<212> TYPE: DNA
<213> ORGANISM: Artificial sequence
<220> FEATURE:
<223> OTHER INFORMATION: Nucleic acid fragment

<400> SEQUENCE: 14
gtaccagcag tagtcgaact gaaggtctcc tct                                   33

<210> SEQ ID NO 15
<211> LENGTH: 25
<212> TYPE: DNA
<213> ORGANISM: Artificial sequece
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t

<400> SEQUENCE: 15
nnaccctgta gaactctgaa cctgt                                            25

<210> SEQ ID NO 16
<211> LENGTH: 22
```

<212> TYPE: DNA
<213> ORGANISM: Artificial sequence
<220> FEATURE:
<223> OTHER INFORMATION: Nucleic acid fragment

<400> SEQUENCE: 16
acaggttcag agttctacag ct                                              22

<210> SEQ ID NO 17
<211> LENGTH: 39
<212> TYPE: DNA
<213> ORGANISM: Artificial sequence
<220> FEATURE:
<223> OTHER INFORMATION: Nucleic acid fragment

<400> SEQUENCE: 17
aatgatacgg cgaccaccga caggttcaga gttctacag                            39

<210> SEQ ID NO 18
<211> LENGTH: 43
<212> TYPE: DNA
<213> ORGANISM: Artificial sequence
<220> FEATURE:
<223> OTHER INFORMATION: Nucleic acid fragment

<400> SEQUENCE: 18
caagcagaag acggcatacg atagtcgaac tgaaggtctc cag                       43

<210> SEQ ID NO 19
<211> LENGTH: 25
<212> TYPE: DNA
<213> ORGANISM: Artificial sequence
<220> FEATURE:
<223> OTHER INFORMATION: Nucleic acid fragment

<400> SEQUENCE: 19
gacagaagcg agtccgactg tgctc                                           25

<210> SEQ ID NO 20
<211> LENGTH: 27
<212> TYPE: DNA
<213> ORGANISM: Artificial sequence
<220> FEATURE:
<223> OTHER INFORMATION: Nucleic acid fragment

<400> SEQUENCE: 20
tagtcgaact gaaggtctcc agcaggg                                         27

<210> SEQ ID NO 21
<211> LENGTH: 48
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (34)..(48)
<223> OTHER INFORMATION: n is a, c, g, or t

<400> SEQUENCE: 21
gtaccagcag tagtcgaact gaaggtctcc tctnnnnnnn nnnnnnnn                  48

<210> SEQ ID NO 22
<211> LENGTH: 23
<212> TYPE: DNA
<213> ORGANISM: Artificial sequence
<220> FEATURE:

<223> OTHER INFORMATION: Nucleic acid fragment

<400> SEQUENCE: 22
tagtcgaact gaaggtctcc agc                                             23

<210> SEQ ID NO 23
<211> LENGTH: 33
<212> TYPE: DNA
<213> ORGANISM: Artificial sequence
<220> FEATURE:
<223> OTHER INFORMATION: Nucleic acid fragment

<400> SEQUENCE: 23
gtaccagcag tagtcgaact gaaggtctcc tct                                  33

<210> SEQ ID NO 24
<211> LENGTH: 25
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t

<400> SEQUENCE: 24
nngtcctgta gaactctgaa cctgt                                           25

<210> SEQ ID NO 25
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 25
acaggttcag agttctacag gac                                             23

<210> SEQ ID NO 26
<211> LENGTH: 39
<212> TYPE: DNA
<213> ORGANISM: Artificial sequence
<220> FEATURE:
<223> OTHER INFORMATION: Nucleic acid fragment

<400> SEQUENCE: 26
aatgatacgg cgaccaccga caggttcaga gttctacag                            39

<210> SEQ ID NO 27
<211> LENGTH: 43
<212> TYPE: DNA
<213> ORGANISM: Artificial sequence
<220> FEATURE:
<223> OTHER INFORMATION: Nucleic acid fragment

<400> SEQUENCE: 27
caagcagaag acggcatacg atagtcgaac tgaaggtctc cag                       43

<210> SEQ ID NO 28
<211> LENGTH: 27
<212> TYPE: DNA
<213> ORGANISM: Artificial sequence
<220> FEATURE:
<223> OTHER INFORMATION: Nucleic acid fragment

<400> SEQUENCE: 28
tagtcgaact gaaggtctcc agcaggg                                                27

<210> SEQ ID NO 29
<211> LENGTH: 48
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (34)..(48)
<223> OTHER INFORMATION: n is a, c, g, or t

<400> SEQUENCE: 29
gtaccagcag tagtcgaact gaaggtctcc tctnnnnnnn nnnnnnn                           48

<210> SEQ ID NO 30
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 30
tagtcgaact gaaggtctcc agc                                                    23

<210> SEQ ID NO 31
<211> LENGTH: 33
<212> TYPE: DNA
<213> ORGANISM: Artificial sequence
<220> FEATURE:
<223> OTHER INFORMATION: Nucleic acid fragment

<400> SEQUENCE: 31
gtaccagcag tagtcgaact gaaggtctcc tct                                         33

<210> SEQ ID NO 32
<211> LENGTH: 25
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t

<400> SEQUENCE: 32
nnggactgta gaactctgaa cctgt                                                  25

<210> SEQ ID NO 33
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 33
acaggttcag agttctacag tcc                                                    23

<210> SEQ ID NO 34
<211> LENGTH: 39
<212> TYPE: DNA
<213> ORGANISM: Artificial sequence
<220> FEATURE:
<223> OTHER INFORMATION: Nucleic acid fragment

<400> SEQUENCE: 34
aatgatacgg cgaccaccga caggttcaga gttctacag                                      39

<210> SEQ ID NO 35
<211> LENGTH: 43
<212> TYPE: DNA
<213> ORGANISM: Artificial sequence
<220> FEATURE:
<223> OTHER INFORMATION: Nucleic acid fragment

<400> SEQUENCE: 35
caagcagaag acggcatacg atagtcgaac tgaaggtctc cag                                 43

<210> SEQ ID NO 36
<211> LENGTH: 27
<212> TYPE: DNA
<213> ORGANISM: Artificial sequence
<220> FEATURE:
<223> OTHER INFORMATION: Nucleic acid fragment

<400> SEQUENCE: 36
tagtcgaact gaaggtctcc agcaggg                                                   27

<210> SEQ ID NO 37
<211> LENGTH: 48
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (34)..(48)
<223> OTHER INFORMATION: n is a, c, g, or t

<400> SEQUENCE: 37
gtaccagcag tagtcgaact gaaggtctcc tctnnnnnnn nnnnnnn                             48

<210> SEQ ID NO 38
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 38
tagtcgaact gaaggtctcc agc                                                       23

<210> SEQ ID NO 39
<211> LENGTH: 33
<212> TYPE: DNA
<213> ORGANISM: Artificial sequence
<220> FEATURE:
<223> OTHER INFORMATION: Nucleic acid fragment

<400> SEQUENCE: 39
gtaccagcag tagtcgaact gaaggtctcc tct                                            33

<210> SEQ ID NO 40
<211> LENGTH: 25
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t

```
<400> SEQUENCE: 40
nngagctgta gaactctgaa cctgt                                         25

<210> SEQ ID NO 41
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 41
acaggttcag agttctacag ctc                                           23

<210> SEQ ID NO 42
<211> LENGTH: 39
<212> TYPE: DNA
<213> ORGANISM: Artificial sequence
<220> FEATURE:
<223> OTHER INFORMATION: Nucleic acid fragment

<400> SEQUENCE: 42
aatgatacgg cgaccaccga caggttcaga gttctacag                          39

<210> SEQ ID NO 43
<211> LENGTH: 43
<212> TYPE: DNA
<213> ORGANISM: Artificial sequence
<220> FEATURE:
<223> OTHER INFORMATION: Nucleic acid fragment

<400> SEQUENCE: 43
caagcagaag acggcatacg atagtcgaac tgaaggtctc cag                     43

<210> SEQ ID NO 44
<211> LENGTH: 27
<212> TYPE: DNA
<213> ORGANISM: Artificial sequence
<220> FEATURE:
<223> OTHER INFORMATION: Nucleic acid fragment

<400> SEQUENCE: 44
tagtcgaact gaaggtctcc agcaggg                                       27

<210> SEQ ID NO 45
<211> LENGTH: 48
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (34)..(48)
<223> OTHER INFORMATION: n is a, c, g, or t

<400> SEQUENCE: 45
gtaccagcag tagtcgaact gaaggtctcc tctnnnnnnn nnnnnnnn                48

<210> SEQ ID NO 46
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 46
```

-continued

```
tagtcgaact gaaggtctcc agc                                            23

<210> SEQ ID NO 47
<211> LENGTH: 33
<212> TYPE: DNA
<213> ORGANISM: Artificial sequence
<220> FEATURE:
<223> OTHER INFORMATION: Nucleic acid fragment

<400> SEQUENCE: 47
gtaccagcag tagtcgaact gaaggtctcc tct                                  33

<210> SEQ ID NO 48
<211> LENGTH: 25
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t

<400> SEQUENCE: 48
nngctctgta gaactctgaa cctgt                                           25

<210> SEQ ID NO 49
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 49
acaggttcag agttctacag agc                                             23

<210> SEQ ID NO 50
<211> LENGTH: 39
<212> TYPE: DNA
<213> ORGANISM: Artificial sequence
<220> FEATURE:
<223> OTHER INFORMATION: Nucleic acid fragment

<400> SEQUENCE: 50
aatgatacgg cgaccaccga caggttcaga gttctacag                            39

<210> SEQ ID NO 51
<211> LENGTH: 43
<212> TYPE: DNA
<213> ORGANISM: Artificial sequence
<220> FEATURE:
<223> OTHER INFORMATION: Nucleic acid fragment

<400> SEQUENCE: 51
caagcagaag acggcatacg atagtcgaac tgaaggtctc cag                       43

<210> SEQ ID NO 52
<211> LENGTH: 27
<212> TYPE: DNA
<213> ORGANISM: Artificial sequence
<220> FEATURE:
<223> OTHER INFORMATION: Nucleic acid fragment

<400> SEQUENCE: 52
tagtcgaact gaaggtctcc agcaggg                                         27
```

```
<210> SEQ ID NO 53
<211> LENGTH: 48
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (34)..(48)
<223> OTHER INFORMATION: n is a, c, g, or t

<400> SEQUENCE: 53
gtaccagcag tagtcgaact gaaggtctcc tctnnnnnnn nnnnnnnn                        48

<210> SEQ ID NO 54
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 54
tagtcgaact gaaggtctcc agc                                                   23

<210> SEQ ID NO 55
<211> LENGTH: 33
<212> TYPE: DNA
<213> ORGANISM: Artificial sequence
<220> FEATURE:
<223> OTHER INFORMATION: Nucleic acid fragment

<400> SEQUENCE: 55
gtaccagcag tagtcgaact gaaggtctcc tct                                        33

<210> SEQ ID NO 56
<211> LENGTH: 25
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t

<400> SEQUENCE: 56
nnaaactgta gaactctgaa cctgt                                                 25

<210> SEQ ID NO 57
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 57
acaggttcag agttctacag ttt                                                   23

<210> SEQ ID NO 58
<211> LENGTH: 25
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t
```

<400> SEQUENCE: 58
nnaccctgta gaactctgaa cctgt    25

<210> SEQ ID NO 59
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 59
acaggttcag agttctacag ggt    23

<210> SEQ ID NO 60
<211> LENGTH: 25
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t

<400> SEQUENCE: 60
nnaggctgta gaactctgaa cctgt    25

<210> SEQ ID NO 61
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 61
acaggttcag agttctacag cct    23

<210> SEQ ID NO 62
<211> LENGTH: 25
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t

<400> SEQUENCE: 62
nnattctgta gaactctgaa cctgt    25

<210> SEQ ID NO 63
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 63
acaggttcag agttctacag aat    23

<210> SEQ ID NO 64
<211> LENGTH: 25
<212> TYPE: DNA
<213> ORGANISM: Artificial sequence
<220> FEATURE:
<223> OTHER INFORMATION: Nucleic acid fragment

```
<220> FEATURE:
<221> NAME/KEY: misc_feature
<222> LOCATION: (1)..(2)
<223> OTHER INFORMATION: n is a, c, g, or t

<400> SEQUENCE: 64
nnctactgta gaactctgaa cctgt                                              25

<210> SEQ ID NO 65
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 65
acaggttcag agttctacag tag                                                23

<210> SEQ ID NO 66
<211> LENGTH: 25
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t

<400> SEQUENCE: 66
nncacctgta gaactctgaa cctgt                                              25

<210> SEQ ID NO 67
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 67
acaggttcag agttctacag gtg                                                23

<210> SEQ ID NO 68
<211> LENGTH: 25
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t

<400> SEQUENCE: 68
nnccgctgta gaactctgaa cctgt                                              25

<210> SEQ ID NO 69
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 69
acaggttcag agttctacag cgg                                                23

<210> SEQ ID NO 70
```

```
<211> LENGTH: 25
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t

<400> SEQUENCE: 70
nncgtctgta gaactctgaa cctgt                                              25

<210> SEQ ID NO 71
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 71
acaggttcag agttctacag acg                                                23

<210> SEQ ID NO 72
<211> LENGTH: 25
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t

<400> SEQUENCE: 72
nngagctgta gaactctgaa cctgt                                              25

<210> SEQ ID NO 73
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 73
acaggttcag agttctacag ctc                                                23

<210> SEQ ID NO 74
<211> LENGTH: 39
<212> TYPE: DNA
<213> ORGANISM: Artificial sequence
<220> FEATURE:
<223> OTHER INFORMATION: Nucleic acid fragment

<400> SEQUENCE: 74
aatgatacgg cgaccaccga caggttcaga gttctacag                               39

<210> SEQ ID NO 75
<211> LENGTH: 43
<212> TYPE: DNA
<213> ORGANISM: Artificial sequence
<220> FEATURE:
<223> OTHER INFORMATION: Nucleic acid fragment

<400> SEQUENCE: 75
caagcagaag acggcatacg atagtcgaac tgaaggtctc cag                          43
```

```
<210> SEQ ID NO 76
<211> LENGTH: 27
<212> TYPE: DNA
<213> ORGANISM: Artificial sequence
<220> FEATURE:
<223> OTHER INFORMATION: Nucleic acid fragment

<400> SEQUENCE: 76
tagtcgaact gaaggtctcc agcaggg                                          27

<210> SEQ ID NO 77
<211> LENGTH: 48
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (34)..(48)
<223> OTHER INFORMATION: n is a, c, g, or t

<400> SEQUENCE: 77
gtaccagcag tagtcgaact gaaggtctcc tctnnnnnnn nnnnnnnn                   48

<210> SEQ ID NO 78
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 78
tagtcgaact gaaggtctcc agc                                              23

<210> SEQ ID NO 79
<211> LENGTH: 33
<212> TYPE: DNA
<213> ORGANISM: Artificial sequence
<220> FEATURE:
<223> OTHER INFORMATION: Nucleic acid fragment

<400> SEQUENCE: 79
gtaccagcag tagtcgaact gaaggtctcc tct                                   33

<210> SEQ ID NO 80
<211> LENGTH: 25
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t

<400> SEQUENCE: 80
nnaaactgta gaactctgaa cctgt                                            25

<210> SEQ ID NO 81
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 81
acaggttcag agttctacag ttt                                              23
```

<210> SEQ ID NO 82
<211> LENGTH: 25
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t

<400> SEQUENCE: 82
nnaccctgta gaactctgaa cctgt                                  25

<210> SEQ ID NO 83
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 83
acaggttcag agttctacag ggt                                    23

<210> SEQ ID NO 84
<211> LENGTH: 25
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t

<400> SEQUENCE: 84
nnaggctgta gaactctgaa cctgt                                  25

<210> SEQ ID NO 85
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 85
acaggttcag agttctacag cct                                    23

<210> SEQ ID NO 86
<211> LENGTH: 25
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t

<400> SEQUENCE: 86
nnattctgta gaactctgaa cctgt                                  25

<210> SEQ ID NO 87
<211> LENGTH: 23
<212> TYPE: DNA
<213> ORGANISM: Artificial sequence
<220> FEATURE:
<223> OTHER INFORMATION: Nucleic acid fragment

```
<400> SEQUENCE: 87
acaggttcag agttctacag aat                                           23

<210> SEQ ID NO 88
<211> LENGTH: 25
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t

<400> SEQUENCE: 88
nncgtctgta gaactctgaa cctgt                                         25

<210> SEQ ID NO 89
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 89
acaggttcag agttctacag acg                                           23

<210> SEQ ID NO 90
<211> LENGTH: 25
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t

<400> SEQUENCE: 90
nnggactgta gaactctgaa cctgt                                         25

<210> SEQ ID NO 91
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 91
acaggttcag agttctacag tcc                                           23

<210> SEQ ID NO 92
<211> LENGTH: 25
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t

<400> SEQUENCE: 92
nngtcctgta gaactctgaa cctgt                                         25

<210> SEQ ID NO 93
```

```
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 93
acaggttcag agttctacag gac                                              23

<210> SEQ ID NO 94
<211> LENGTH: 25
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t

<400> SEQUENCE: 94
nngagctgta gaactctgaa cctgt                                            25

<210> SEQ ID NO 95
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 95
acaggttcag agttctacag ctc                                              23

<210> SEQ ID NO 96
<211> LENGTH: 25
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (1)..(2)
<223> OTHER INFORMATION: n is a, c, g, or t

<400> SEQUENCE: 96
nngctctgta gaactctgaa cctgt                                            25

<210> SEQ ID NO 97
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 97
acaggttcag agttctacag agc                                              23

<210> SEQ ID NO 98
<211> LENGTH: 39
<212> TYPE: DNA
<213> ORGANISM: Artificial sequence
<220> FEATURE:
<223> OTHER INFORMATION: Nucleic acid fragment

<400> SEQUENCE: 98
aatgatacgg cgaccaccga caggttcaga gttctacag                             39
```

-continued

```
<210> SEQ ID NO 99
<211> LENGTH: 43
<212> TYPE: DNA
<213> ORGANISM: Artificial sequence
<220> FEATURE:
<223> OTHER INFORMATION: Nucleic acid fragment

<400> SEQUENCE: 99
caagcagaag acggcatacg atagtcgaac tgaaggtctc cag          43

<210> SEQ ID NO 100
<211> LENGTH: 48
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (34)..(48)
<223> OTHER INFORMATION: n is a, c, g, or t

<400> SEQUENCE: 100
gtaccagcag tagtcgaact gaaggtctcc tctnnnnnnn nnnnnnn      48

<210> SEQ ID NO 101
<211> LENGTH: 42
<212> TYPE: DNA
<213> ORGANISM: Artificial sequence
<220> FEATURE:
<223> OTHER INFORMATION: Nucleic acid fragment

<400> SEQUENCE: 101
tagtcgaact gaaggtctcc agcacaagaa gcctacagga ct            42

<210> SEQ ID NO 102
<211> LENGTH: 42
<212> TYPE: DNA
<213> ORGANISM: Artificial sequence
<220> FEATURE:
<223> OTHER INFORMATION: Nucleic acid fragment

<400> SEQUENCE: 102
tagtcgaact gaaggtctcc agcgcctaca ggactccaaa ta            42

<210> SEQ ID NO 103
<211> LENGTH: 33
<212> TYPE: DNA
<213> ORGANISM: Artificial sequence
<220> FEATURE:
<223> OTHER INFORMATION: Nucleic acid fragment

<400> SEQUENCE: 103
gtaccagcag tagtcgaact gaaggtctcc tct                      33

<210> SEQ ID NO 104
<211> LENGTH: 42
<212> TYPE: DNA
<213> ORGANISM: Artificial sequence
<220> FEATURE:
<223> OTHER INFORMATION: Nucleic acid fragment

<400> SEQUENCE: 104
catctgttcc ctccctgtct cagacaagaa gcctacagga ct            42

<210> SEQ ID NO 105
<211> LENGTH: 42
<212> TYPE: DNA
```

```
<213> ORGANISM: Artificial sequence
<220> FEATURE:
<223> OTHER INFORMATION: Nucleic acid fragment

<400> SEQUENCE: 105
catctgttcc ctccctgtct caggcctaca ggactccaaa ta                              42

<210> SEQ ID NO 106
<211> LENGTH: 46
<212> TYPE: DNA
<213> ORGANISM: Artificial sequence
<220> FEATURE:
<223> OTHER INFORMATION: Nucleic acid fragment

<400> SEQUENCE: 106
ctatcccctg ttgcgtgtct cagtagtcga actgaaggtc tcctct                          46

<210> SEQ ID NO 107
<211> LENGTH: 44
<212> TYPE: DNA
<213> ORGANISM: Artificial sequence
<220> FEATURE:
<223> OTHER INFORMATION: Nucleic acid fragment

<400> SEQUENCE: 107
ccatctcatc cctgcgtgtc ccatctgttc cctccctgtc tcag                            44

<210> SEQ ID NO 108
<211> LENGTH: 44
<212> TYPE: DNA
<213> ORGANISM: Artificial sequence
<220> FEATURE:
<223> OTHER INFORMATION: Nucleic acid fragment

<400> SEQUENCE: 108
cctatcccct gtgtgccttg cctatcccct gttgcgtgtc tcag                            44

<210> SEQ ID NO 109
<211> LENGTH: 27
<212> TYPE: DNA
<213> ORGANISM: Artificial sequence
<220> FEATURE:
<223> OTHER INFORMATION: Nucleic acid fragment

<400> SEQUENCE: 109
tagtcgaact gaaggtctcc agcaggg                                               27

<210> SEQ ID NO 110
<211> LENGTH: 44
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (39)..(44)
<223> OTHER INFORMATION: n is a, c, g, or t

<400> SEQUENCE: 110
tagtcgaact gaaggtctcc gaaccgctct tccgatctnn nnnn                            44

<210> SEQ ID NO 111
<211> LENGTH: 47
<212> TYPE: DNA
<213> ORGANISM: Artificial sequence
<220> FEATURE:
<223> OTHER INFORMATION: Nucleic acid fragment
```

```
<220> FEATURE:
<221> NAME/KEY: misc_feature
<222> LOCATION: (42)..(47)
<223> OTHER INFORMATION: n is a, c, g, or t

<400> SEQUENCE: 111
tagtcgaact gaaggtctcc gaaccgctct tccgatctcg annnnnn        47

<210> SEQ ID NO 112
<211> LENGTH: 47
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (42)..(47)
<223> OTHER INFORMATION: n is a, c, g, or t

<400> SEQUENCE: 112
tagtcgaact gaaggtctcc gaaccgctct tccgatctat cnnnnnn        47

<210> SEQ ID NO 113
<211> LENGTH: 47
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (42)..(47)
<223> OTHER INFORMATION: n is a, c, g, or t

<400> SEQUENCE: 113
tagtcgaact gaaggtctcc gaaccgctct tccgatctgc tnnnnnn        47

<210> SEQ ID NO 114
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 114
tagtcgaact gaaggtctcc agc                                  23

<210> SEQ ID NO 115
<211> LENGTH: 35
<212> TYPE: DNA
<213> ORGANISM: Artificial sequence
<220> FEATURE:
<223> OTHER INFORMATION: Nucleic acid fragment

<400> SEQUENCE: 115
tgacgtcgtc tagtcgaact gaaggtctcc gaacc                     35

<210> SEQ ID NO 116
<211> LENGTH: 44
<212> TYPE: DNA
<213> ORGANISM: Artificial sequence
<220> FEATURE:
<223> OTHER INFORMATION: Nucleic acid fragment

<400> SEQUENCE: 116
aatgatacgg cgaccaccga gatctacact agtcgaactg aagg           44

<210> SEQ ID NO 117
```

<211> LENGTH: 61
<212> TYPE: DNA
<213> ORGANISM: Artificial sequence
<220> FEATURE:
<223> OTHER INFORMATION: Nucleic acid fragment

<400> SEQUENCE: 117
caagcagaag acggcatacg agatcggtct cggcattcct gctgaaccgc tcttccgatc    60
t                                                                   61

<210> SEQ ID NO 118
<211> LENGTH: 27
<212> TYPE: DNA
<213> ORGANISM: Artificial sequence
<220> FEATURE:
<223> OTHER INFORMATION: Nucleic acid fragment

<400> SEQUENCE: 118
tagtcgaact gaaggtctcc agcaggg                                        27

<210> SEQ ID NO 119
<211> LENGTH: 27
<212> TYPE: DNA
<213> ORGANISM: Artificial sequence
<220> FEATURE:
<223> OTHER INFORMATION: Nucleic acid fragment

<400> SEQUENCE: 119
tagtcgaact gaaggtctcc agcaaaa                                        27

<210> SEQ ID NO 120
<211> LENGTH: 27
<212> TYPE: DNA
<213> ORGANISM: Artificial sequence
<220> FEATURE:
<223> OTHER INFORMATION: Nucleic acid fragment

<400> SEQUENCE: 120
tagtcgaact gaaggtctcc agcaccc                                        27

<210> SEQ ID NO 121
<211> LENGTH: 24
<212> TYPE: DNA
<213> ORGANISM: Artificial sequence
<220> FEATURE:
<223> OTHER INFORMATION: Nucleic acid fragment

<400> SEQUENCE: 121
tagtcgaact gaaggtctcc agca                                           24

<210> SEQ ID NO 122
<211> LENGTH: 44
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (39)..(44)
<223> OTHER INFORMATION: n is a, c, g, or t

<400> SEQUENCE: 122
tagtcgaact gaaggtctcc gaaccgctct tccgatctnn nnnn                     44

<210> SEQ ID NO 123
<211> LENGTH: 23

```
<212> TYPE: DNA
<213> ORGANISM: Artificial sequence
<220> FEATURE:
<223> OTHER INFORMATION: Nucleic acid fragment

<400> SEQUENCE: 123
tagtcgaact gaaggtctcc agc                                      23

<210> SEQ ID NO 124
<211> LENGTH: 35
<212> TYPE: DNA
<213> ORGANISM: Artificial sequence
<220> FEATURE:
<223> OTHER INFORMATION: Nucleic acid fragment

<400> SEQUENCE: 124
tgacgtcgtc tagtcgaact gaaggtctcc gaacc                         35

<210> SEQ ID NO 125
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 125
tagtcgaact gaaggtctcc agc                                      23

<210> SEQ ID NO 126
<211> LENGTH: 35
<212> TYPE: DNA
<213> ORGANISM: Artificial sequence
<220> FEATURE:
<223> OTHER INFORMATION: Nucleic acid fragment

<400> SEQUENCE: 126
tgacgtcgtc tagtcgaact gaaggtctcc gaacc                         35

<210> SEQ ID NO 127
<211> LENGTH: 44
<212> TYPE: DNA
<213> ORGANISM: Artificial sequence
<220> FEATURE:
<223> OTHER INFORMATION: Nucleic acid fragment

<400> SEQUENCE: 127
aatgatacgg cgaccaccga gatctacact agtcgaactg aagg               44

<210> SEQ ID NO 128
<211> LENGTH: 61
<212> TYPE: DNA
<213> ORGANISM: Artificial sequence
<220> FEATURE:
<223> OTHER INFORMATION: Nucleic acid fragment

<400> SEQUENCE: 128
caagcagaag acggcatacg agatcggtct cggcattcct gctgaaccgc tcttccgatc    60
t                                                              61

<210> SEQ ID NO 129
<211> LENGTH: 27
<212> TYPE: DNA
<213> ORGANISM: Artificial sequence
<220> FEATURE:
<223> OTHER INFORMATION: Nucleic acid fragment
```

<400> SEQUENCE: 129
tagtcgaact gaaggtctcc agcaggg                                           27

<210> SEQ ID NO 130
<211> LENGTH: 48
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (34)..(48)
<223> OTHER INFORMATION: n is a, c, g, or t

<400> SEQUENCE: 130
gtaccagcag tagtcgaact gaaggtctcc tctnnnnnnn nnnnnnn                     48

<210> SEQ ID NO 131
<211> LENGTH: 38
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (24)..(38)
<223> OTHER INFORMATION: n is a, c, g, or t

<400> SEQUENCE: 131
tagtcgaact gaaggtctcc tctnnnnnnn nnnnnnn                                38

<210> SEQ ID NO 132
<211> LENGTH: 44
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (30)..(44)
<223> OTHER INFORMATION: n is a, c, g, or t

<400> SEQUENCE: 132
gtaccagcag cgaactgaag gtctcctctn nnnnnnnnn nnnn                         44

<210> SEQ ID NO 133
<211> LENGTH: 40
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (26)..(40)
<223> OTHER INFORMATION: n is a, c, g, or t

<400> SEQUENCE: 133
gtaccagcag ctgaaggtct cctctnnnnn nnnnnnnnn                              40

<210> SEQ ID NO 134
<211> LENGTH: 48
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (34)..(48)
<223> OTHER INFORMATION: n is a, c, g, or t

```
<400> SEQUENCE: 134 cgtcataacct cggcacaatt gcgatatcgg gtannnnnnn nnnnnnnn            48

<210> SEQ ID NO 135
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 135
tagtcgaact gaaggtctcc agc                                       23

<210> SEQ ID NO 136
<211> LENGTH: 33
<212> TYPE: DNA
<213> ORGANISM: Artificial sequence
<220> FEATURE:
<223> OTHER INFORMATION: Nucleic acid fragment

<400> SEQUENCE: 136
gtaccagcag tagtcgaact gaaggtctcc tct                            33

<210> SEQ ID NO 137
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 137
tagtcgaact gaaggtctcc tct                                       23

<210> SEQ ID NO 138
<211> LENGTH: 29
<212> TYPE: DNA
<213> ORGANISM: Artificial sequence
<220> FEATURE:
<223> OTHER INFORMATION: Nucleic acid fragment

<400> SEQUENCE: 138
gtaccagcag cgaactgaag gtctcctct                                 29

<210> SEQ ID NO 139
<211> LENGTH: 25
<212> TYPE: DNA
<213> ORGANISM: Artificial sequence
<220> FEATURE:
<223> OTHER INFORMATION: Nucleic acid fragment

<400> SEQUENCE: 139
gtaccagcag ctgaaggtct cctct                                     25

<210> SEQ ID NO 140
<211> LENGTH: 33
<212> TYPE: DNA
<213> ORGANISM: Artificial sequence
<220> FEATURE:
<223> OTHER INFORMATION: Nucleic acid fragment

<400> SEQUENCE: 140 cgtcataacct cggcacaatt gcgatatcgg gta                           33

<210> SEQ ID NO 141
```

```
<211> LENGTH: 27
<212> TYPE: DNA
<213> ORGANISM: Artificial sequence
<220> FEATURE:
<223> OTHER INFORMATION: Nucleic acid fragment

<400> SEQUENCE: 141
tagtcgaact gaaggtctcc agcaggg                                              27

<210> SEQ ID NO 142
<211> LENGTH: 27
<212> TYPE: DNA
<213> ORGANISM: Artificial sequence
<220> FEATURE:
<223> OTHER INFORMATION: Nucleic acid fragment

<400> SEQUENCE: 142
tagtcgaact gaaggtctcc agcaggg                                              27

<210> SEQ ID NO 143
<211> LENGTH: 48
<212> TYPE: DNA
<213> ORGANISM: Artificial sequence
<220> FEATURE:
<223> OTHER INFORMATION: Nucleic acid fragment
<220> FEATURE:
<221> NAME/KEY: misc_feature
<222> LOCATION: (34)..(48)
<223> OTHER INFORMATION: n is a, c, g, or t

<400> SEQUENCE: 143
gtaccagcag tagtcgaact gaaggtctcc tctnnnnnnn nnnnnnnn                       48

<210> SEQ ID NO 144
<211> LENGTH: 23
<212> TYPE: DNA
<213> ORGANISM: Artificial sequence
<220> FEATURE:
<223> OTHER INFORMATION: Nucleic acid fragment

<400> SEQUENCE: 144
tagtcgaact gaaggtctcc agc                                                  23

<210> SEQ ID NO 145
<211> LENGTH: 33
<212> TYPE: DNA
<213> ORGANISM: Artificial sequence
<220> FEATURE:
<223> OTHER INFORMATION: Nucleic acid fragment

<400> SEQUENCE: 145
gtaccagcag tagtcgaact gaaggtctcc tct                                       33
```

METHOD OF MANUFACTURING A MIXTURE OF AMPLIFIED DOUBLE-STRANDED NUCLEIC ACIDS COMPRISING UNKNOWN SEQUENCE

CROSS REFERENCE TO RELATED APPLICATIONS

This application is a national stage of PCT International Application No. PCT/JP2009/061552, filed Jun. 18, 2009, which claims priority under Japanese patent application: JP2008-159527, filed Jun. 18, 2008 in the Japanese Patent Office, the disclosure of which is herein incorporated by reference in its entirety.

BACKGROUND OF THE INVENTION

1. Field of the Invention

The subject invention pertains to a unique method of manufacturing a mixture of amplified double-stranded nucleic acids comprising unknown sequence.

2. Discussion of the Background

The 5' End of Nucleic Acid Strand and the Methods to Capture it

The precise determination of the sequence around each 5' end of nucleic acids is of a special interest in biology. In the case of ribonucleic acid (RNA), this sequence reveals a corresponding location in the chromosomes, the gene promoter, which is a crucial component of the gene regulation mechanism. Therefore, many efforts have been made to isolate 5' ends of RNA molecules. However, it is difficult to be certain that the observed 5' end corresponds to a molecule really existing in vivo and is not the product of the truncation of a longer RNA molecule during the experiment.

Several approaches have taken advantage of the fact that the 5' ends of the complex fraction of the total RNA content of living cells—comprising the messenger RNAs (mRNAs)—can be distinguished by the presence of a specific modification, called the cap, which consists of a guanosine 5' triphosphate modified by one or more methylations. In experimental conditions, RNA molecules bearing the cap can be considered intact in their 5' end, and methods aimed to capture the 5' ends ensure that only these molecules participate to the final product. For instance, in the Cap-Trapper method, the diol group of the cap is used to bind 5'-intact RNA molecules on beads and to exclude complementary deoxyribonucleic acids (cDNAs) of truncated RNA molecules [Caminci 2001 the disclosure of which is herein incorporated by reference in its entirety.]. In the oligo-capping method, a 5' oligonucleotide is attached to the RNA molecules in three reactions using phosphatase, pyrophosphatase and ligase [Maruyama 1994, the disclosure of which is herein incorporated by reference in its entirety.]. In the CAPswitch method, the propensity of the reverse transcriptase (RTase) to add extra cytidine nucleotides to the first-strand cDNAs templated from capped molecules is exploited to distinguish them from the uncapped RNAs [Chenchik 1999, U.S. Pat. No. 5,962,272, the disclosure of which is herein incorporated by reference in its entirety.].

The CAPswitch Method

Chenchick et al invented the CAPswitch method, "for the synthesis and cloning of full-length cDNA, or cDNA fragments, that correspond to the complete sequence of 5'-ends of mRNA molecules". Pivotal in this method is the use of a template switching (TS) oligonucleotide that serves as a new template to extend the first-strand cDNAs after they reach the cap of their mRNA template. The mechanism of CAPswitch was not clearly understood at the when this method was patented. The optimal sequence at the 3' end of the TS oligonucleotide was determined by Chenchick et al by using TS oligonucleotide finishing with random nucleotides and analyzing the sequence of the resulting full-length cDNAs. It was then refined by a mutagenesis analysis. They hypothesized that the TS oligonucleotide would hybridize to the cap structure of the mRNA (see the CAPswitch patent's abstract and figures), or to extra 3' cytidine residues on the first-strand cDNA added by a terminal transferase activity of the RTase. The role of the CAP was unclear, as it was stated that it was not a necessary requirement for strand template-switching, but was making the reaction more effective for full-length In fact, It has been demonstrated that the mechanism for first-strand cDNA extension depends on the molecular nature of the cap, because it is used by the RTase as a template for a short extension of the full-length cDNA: cytosines are added for 7-methylguanosine caps [Hirzmann 1993, the disclosure of which is herein incorporated by reference in its entirety.], but in the case of adenosine caps (very frequent intermediate steps in enzymatic reactions), the extra nucleotides added are thymidines [Ohtake 2004, the disclosure of which is herein incorporated by reference in its entirety.]. A residual terminal transferase activity is detected for cap-less RNA molecules and as a 5% background for capped molecules. This explains why only cDNAs that reached the 5' end of a RNA molecule can switch template.

The patent of Chenchick et al is written broadly and covers usage of total RNA or polyA-tailed RNA, the use of oligodT or random RT primers, the specific amplification of one gene or the amplification of a whole library.

However, eight years after it was issued, there is no academic or commercial evidence that the patented method can be used to amplify a library of complete 5' ends of capped RNA (with and without polyA tails) using random RT primers on total RNA at nanogram scale. In the example number 1 of the patent, a library is made using random primers, but together with polyadenylated RNA. In example 2, a library is made from 100 nanograms of total RNA, but using oligodT RT primers. In example number 3 polyadenylated RNA is reverse-transcribed with a double stranded oligodT primer. In example number 4, total RNA is reverse-transcribed by oligodT primers, and the subsequent steps include a enzymatic cleavage in which the 5' completeness is lost. The patent does contain an example of usage of CAPswitch with total RNA and random RT primers. However, it is in the context of the "5' rapid amplification of cDNA ends" method, which is gene-specific: the products of the RT are not amplified as a library.

Consequently, simultaneous practical usage of random RT primers and total RNA for preparing a library of complete 5' ends is absent in the patent or in the later literature, and thus the RT products having the complete 5' ends are not amplified as a library.

Suppressive PCR

Suppressive PCR is known as a method used for the preparation of libraries of target nucleic acids in a complex nucleic acid mixture and used to selectively control the size of PCR products which can be amplified in a reaction.

Suppressive PCR was invented by Chenchik et al, who were issued the U.S. Pat. No. 5,565,340 in 1996 ([Chenchik 1996, the disclosure of which is herein incorporated by reference in its entirety.]). In this method, some DNA molecules are prevented from being amplified during a PCR by adding complementary adapters to their 5' and 3' ends. The complementarity between the adapters exceeds the complementarity between adapters and PCR primers. During the annealing step of the reaction, intramolecular folding will be favored compared to hybridization with PCR primers, and the folded templates will not be extended. Due to the exponential nature of the PCR, when a significant number of molecules skip amplification at every cycle, their contribution to the final product becomes neglectable.

The strategies of suppressive PCR can be classified in two categories. In the first, the PCR is made with a pair of different forward and reverse primers, and each adapter have complementarity to one of them. Therefore, the templates flanked by the same adapter will be suppressed, whereas templates that match both PCR primers will be amplified.

In the second category, the PCR is made with a single primer. In this case, the molecules that will be amplified are the ones for which the intramolecular folding is the less probable: the longer molecules. This approach is usually employed to suppress primer dimers and counterbalance the tendency of the PCR to favour the shortest amplicons [Brownie 1997, the disclosure of which is herein incorporated by reference in its entirety.].

To summarize, there are two possible strategies of suppressive PCR with distinct advantages: the first strategy described above results in a sequence-based selection while the latter strategy gives rise to a size-based selection, trying to overcome the bias towards short-sized templates that commonly affects PCR.

However, it is unfortunately difficult to get all the benefits of the suppressive PCR method at the same time: to normalize the size of the amplicons and eliminate primer dimers, the templates should have the suppressive sequences in 5' and 3', but when the method is used to eliminate other artifacts, the desired templates should be amplified with distinct forward and reverse PCR primers.

The reason why it was very difficult to combine total RNA, CAPswitch and random priming for the preparation of libraries of complete 5' ends from nanograms of template is the artifacts created during the RT. Since only low quantities of template are used, the second-strand cDNA synthesis should be coupled with an amplification step, typically PCR, in which the artifacts will outcompete the 5'-complete cDNAs. Artifacts can be created in the following situations:

TS oligonucleotides can compete with RT primers for binding the RNA molecules, especially at the cool temperatures used for annealing the random RT primers. (See FIG. 48A)

RT primers can invade the DNA-RNA duplex when the RTase pauses (this enzyme is not very processive), and terminate the reaction by premature template-switching. (See FIG. 48B)

As 25% of the random RT primers finish by a guanine, they can compete with the TS oligonucleotides for binding the extra cytosines added in 5' of the first strand cDNA by the RT. (See FIG. 48C)

TS oligonucleotides can hybridise with the random RT primers, and the RTase can extend these complexes. (See FIG. 48D)

Random RT primers hybridize each other can and be extended as well. (See FIG. 48D)

At first the inventors thought to use suppressive PCR to avoid the amplification of the primers dimers, by giving them a sequence tail designed according to Chenchick et al's method and using single universal PCR primer.

SUMMARY OF THE INVENTION

However, this design does not allow suppressing the artifacts created by premature template-switching after strand invasion, or by priming the RNA with the TS oligonucleotide. Each artifact introduces noise in the information: when the RT primer triggers template switching of the RTase, some internal sequences can be mistaken for transcription starting sites, and when the TS oligonucleotide primes the RNA, the resulting cDNA loses directionality and can be mistaken for an antisense transcript.

Therefore, the purpose of the subject invention is to provide a method of manufacturing a mixture of amplified double-stranded nucleic acids comprising unknown sequence including the complete 5' end sequence.

The inventors found that using a different sequence for the TS oligonucleotide and the RT primer tails would tackle the problem of the long artifacts, but in practice the primer dimers originating from the interaction between the TS oligonucleotide and the RT primer take over the PCR.

Consequently, the inventors succeeded in inventing the following method to tackle all issues at the same time based on the above finding.

[1]. A method of manufacturing a mixture of amplified double-stranded nucleic acids comprising:
(a) preparing a single-stranded nucleic acid comprising a single-stranded adapter 1, a single-stranded nucleic acid fragment and a single-stranded adapter 2,
wherein said single-stranded adapter 1 comprises at least a common sequence 1 and a suffix sequence 1,
said single-stranded adapter 2 comprises at least a suffix sequence 2 and a common sequence 2,
wherein said common sequence 1 and said common sequence 2 are reverse-complementary, and
said suffix sequence 1 and said suffix sequence 2 are not reverse-complementary; and
(b) conducting PCR with said single-stranded nucleic acid prepared in step (a), a primer 1 comprising at least a part of the common sequence 1 and the suffix sequence 1, and a primer 2 comprising a part of the reverse-complement of the common sequence 2 and the reverse-complement of the suffix sequence 2 to amplify double-stranded nucleic acids.

[2]. The method according to the above [1], wherein said adapter 1 further comprises a prefix sequence 1 at 5' end thereof and said primer 1 further comprises said prefix sequence 1 at 5' end thereof, or
said primer 1 further comprises said prefix sequence 1 at 5' end thereof

[3]. The method according to the above [1] or [2], wherein said adapter 2 further comprises a prefix sequence 2 at 3' end thereof and said primer 2 further comprises a sequence reverse-complementary to said prefix sequence 2 at 5' end thereof, or
said primer 2 further comprises a sequence reverse-complementary to said prefix sequence 2 at 5' end thereof.

[4]. The method according to any one of the above [1] to [3], wherein in a case where a single-stranded template nucleic acid comprising a sequence complementary to the single-stranded nucleic acid fragment has a cap structure or one or more extra 3'-ribonucleotide at 5' end thereof, said step (a) comprises nucleic acid strand synthesis reaction using the single-stranded template nucleic acid; an oligonucleotide comprising at 3' end thereof at least one nucleotide that can hybridize to extra 3'-nucleotides at 3' end of the single-stranded nucleic acid fragment, and a sequence reverse-complementary to the adapter 2; and a primer 3 comprising at least a random sequence or an oligo-T at 3' end thereof and a sequence corresponding to the adapter 1.

[5]. The method according to the above [4], wherein the single-stranded template nucleic acid is RNA and the nucleic acid strand synthesis reaction is reverse transcription reaction.

[6]. The method according to any one of the above [1] to [5], wherein said common sequence 1 and said common sequence 2 comprise at least a restriction site, respectively.
[7]. The method according to any one of the above [1] to [6], wherein the nucleotide length of said suffix sequence 1 and said suffix sequence 2 is 2 to 5 bases.
[8]. The method according to any one of the above [1] to [7], wherein the nucleotide length of said common sequence 1 and said common sequence 2 is 15 to 30 bases.
[9]. The method according to any one of the above [2] to [8], wherein the nucleotide length of said prefix sequence 1 is 8 to 15 bases.
[10]. The method according to any one of the above [3] to [9], wherein the nucleotide length of said prefix sequences 2 is 8 to 15 bases.
[11]. The method according to any one of the above [1] to [10], wherein each of the amplified double-stranded nucleic acids is a double-stranded cDNA comprising a sequence corresponding to a 5' end side sequence of RNA.
[12]. The method according to any one of the above [5] to [11], wherein said single-stranded adapter 1 further comprises an extra sequence 1 at 5' end of the suffix sequence 1, and/or said single-stranded adapter 2 further comprises an extra sequence 2 at 3' end of the suffix sequence 2.
[13]. The method according to the above [12], wherein the nucleotide length of said extra sequence 1 is 15 to 30, and the nucleotide length of said extra sequence 2 is 15 to 30 bases.
[14]. A method for determining the 5' end side sequence of RNA comprising determining the 5' end side sequence of RNA used as the single-stranded template nucleic acid by sequencing from 3' end side to 5' end side and/or from 5' end side to 3' end side the double-stranded nucleic acids in the mixture of amplified double-stranded nucleic acids obtained by the method according to any one of the above [5] to [13].

BRIEF DESCRIPTION OF THE DRAWINGS

FIG. 27 shows the result of purification of the tags before/after gel cutting carried out with Example 7.

FIG. 28 shows the result of the purity of the sample carried out with Example 7.

FIG. 31 shows the agarose gel analysis result of 2nd round of 1st PCR (moderately suppressive PCR) large scale carried out with Example 8.

FIG. 32 shows the result of purification of the 1st round tags before/after gel cutting carried out with Example 8.

FIG. 33 shows the result of purification of the 2nd round tags before/after gel cutting carried out with Example 8.

FIG. 34 shows the result of 3'-RACE by moderately suppressive PCR carried out with Example 9. 1.5% Agarose gel: 100V, 27 min, NC: Negative control (no template)

FIG. 38 shows the agarose gel analysis result of 2nd PCR small scale carried out with Example 10

FIG. 39 shows the agarose gel analysis of the PCR products before/after cutting carried out with Example 10.

FIG. 45 shows a list of primers used in the moderately suppressive PCR carried out with Comparison of RT/moderately suppressive primers. The sequence of the primers are:

| Random RT primers | Reverse PCR primers |
|---|---|
| N-15, SEQ ID NO: 130 | N-15, SEQ ID NO: 136 |
| N-15-notail, SEQ ID NO: 131 | N-15-notail, SEQ ID NO: 137 |
| N-15-del4, SEQ ID NO: 132 | N-15-del4, SEQ ID NO: 138 |
| N-15-del8, SEQ ID NO: 133 | N-15-del8, SEQ ID NO: 139 |
| N-15-shuffled, SEQ ID NO: 134 | N-15-shuffled, SEQ ID NO: 140 |

Figure 46:
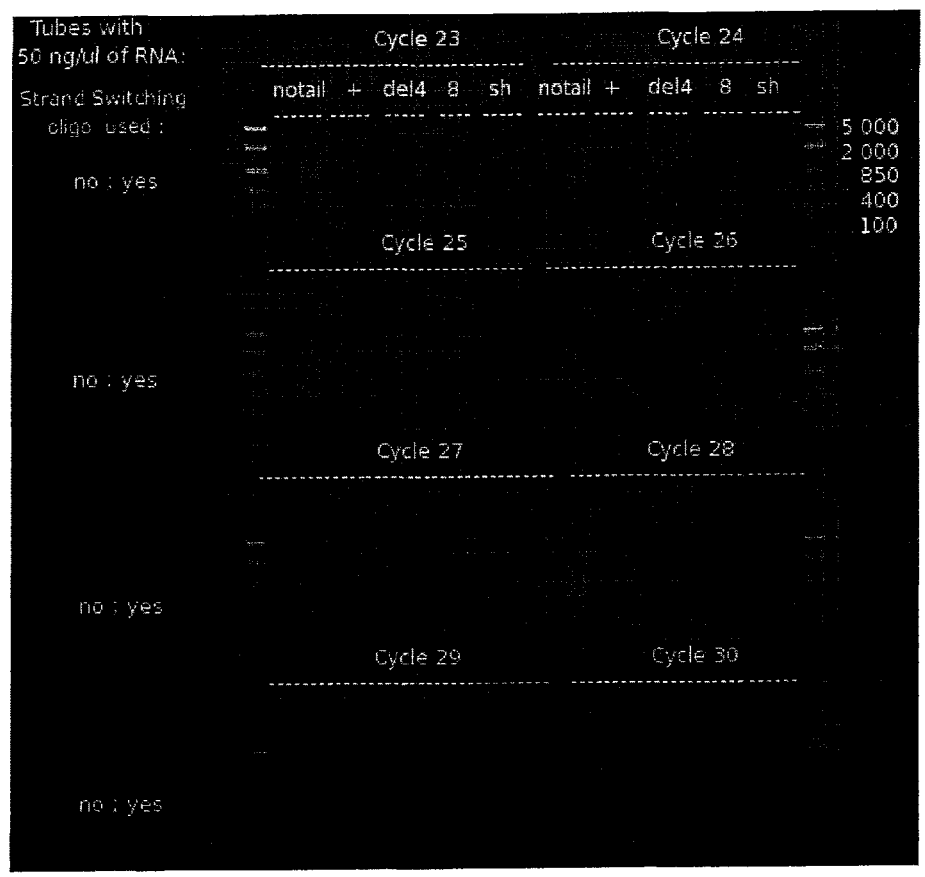

FIG. 46 shows the result of PCR carried out with Comparison of RT/moderately suppressive primers.

Figure 47:
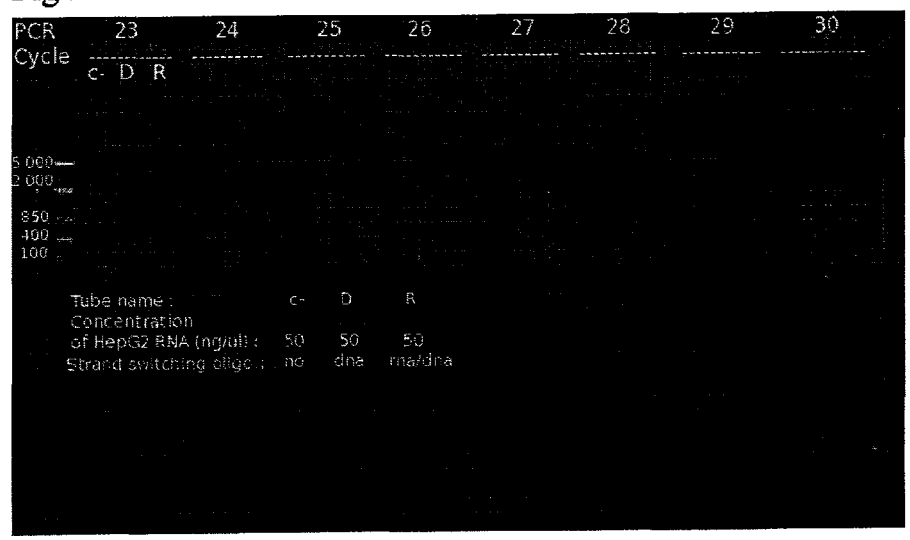
Figure 48A:
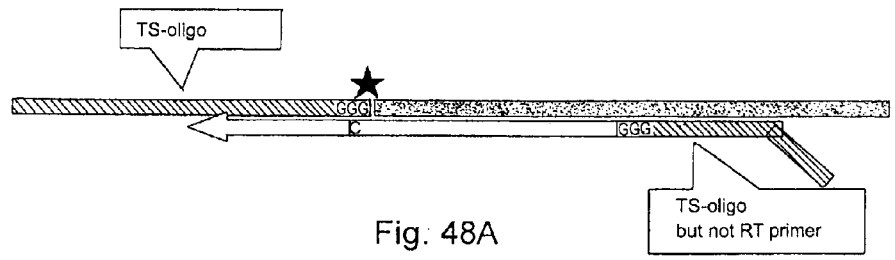
Figure 48B:
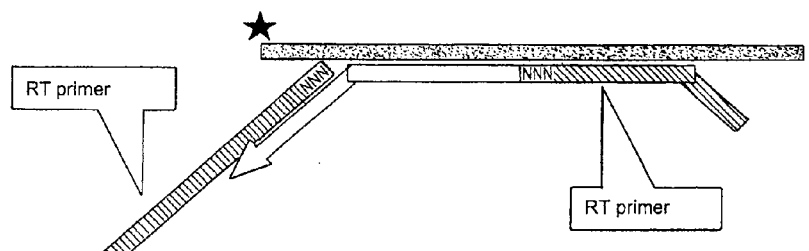
Figure 48C:
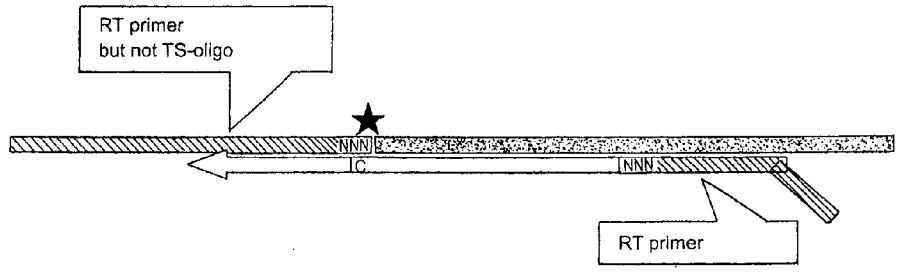
Figure 48D:
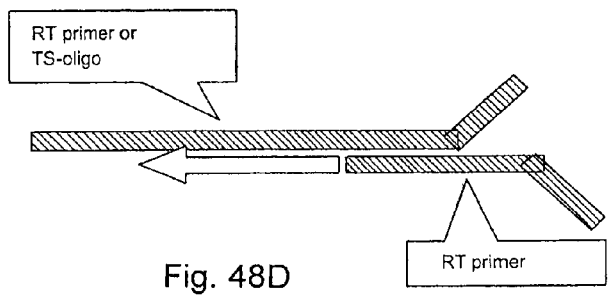

FIG. 47 shows the result of PCR carried out with Comparison of DNA TS oligo.

FIG. 48 shows situations where artifacts can be created during RT: (A) demonstrates TS oligonucleotides can compete with RT primers for binding the RNA molecules, especially at the cool temperatures used for annealing the random RT primers, (B) demonstrates that RT primers can invade the DNA-RNA duplex when the RTase pauses (this enzyme is not very processive), and terminate the reaction by premature template-switching; (C) demonstrates that as 25% of the random RT primers finish by a guanine, they can compete with the TS oligonucleotides for binding the extra cytosines added in 5' of the first strand cDNA by the RT, and; (D) demonstrates that TS oligonucleotides can hybridise with the random RT primers, and the RTase can extend these complexes. Random RT primers hybridize each other can and be extended as well.

Figure 49:
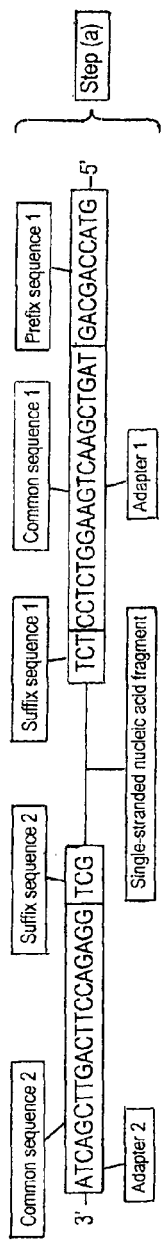

FIG. 49 is an example of the single-stranded nucleic acid where the adapter 1 (nucleotides 1-33 of SEQ ID NO: 2) comprises the prefix sequence 1.

Figure 50:
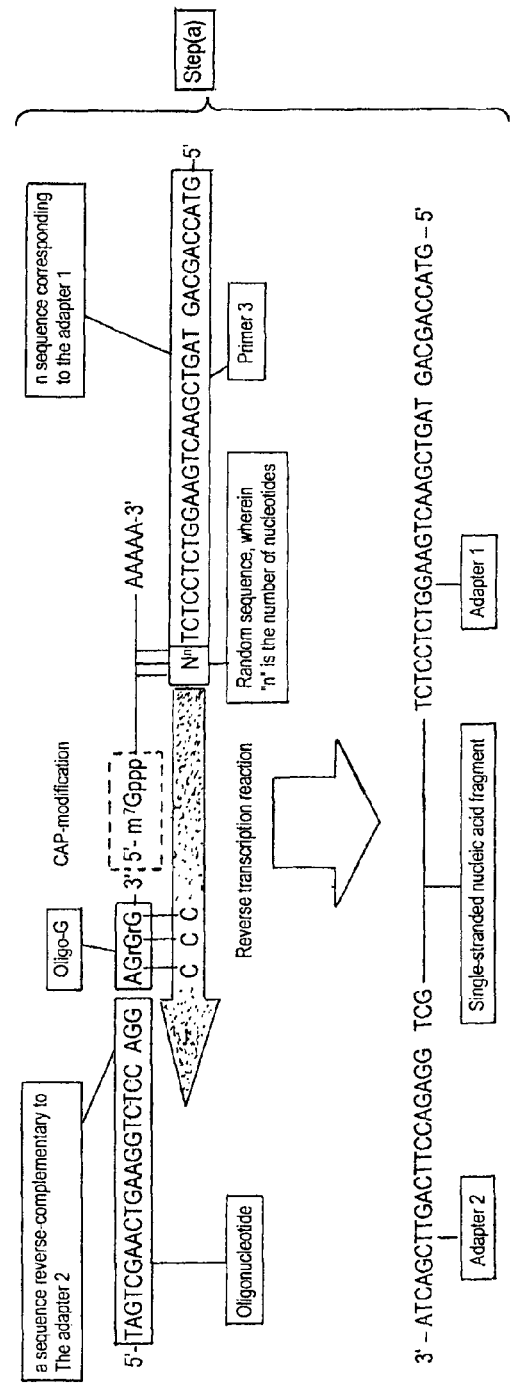

FIG. 50 shows an example where the primer 3 comprises nucleotides 1-33 of SEQ ID NO: 2 with random sequence at 3' end thereof. The sequences of the oligonucleotide, the adapters and primer below are: oligonucleotide, SEQ ID NO: 4 with oligo-riboguanosine at 3' end thereof; Adapter 1 and Primer 1, nucleotides 1-33 of SEQ ID NO: 2; Primer 2, SEQ ID NO: 4; Adapter 2, the complement of SEQ ID NO: 4; primer 3, nucleotides 1-33 of SEQ ID NO: 2.

Figure 51:
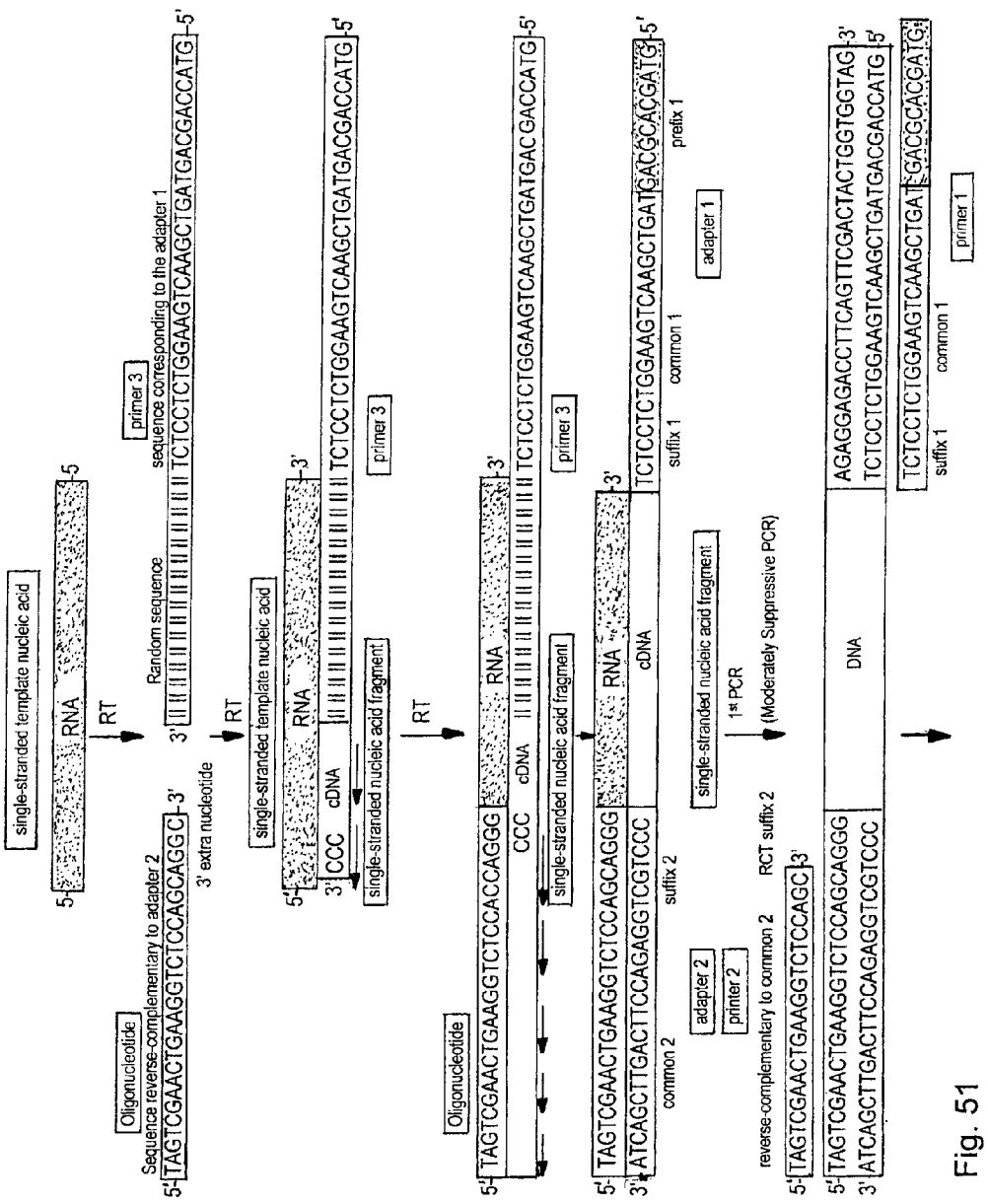
Figure 51:
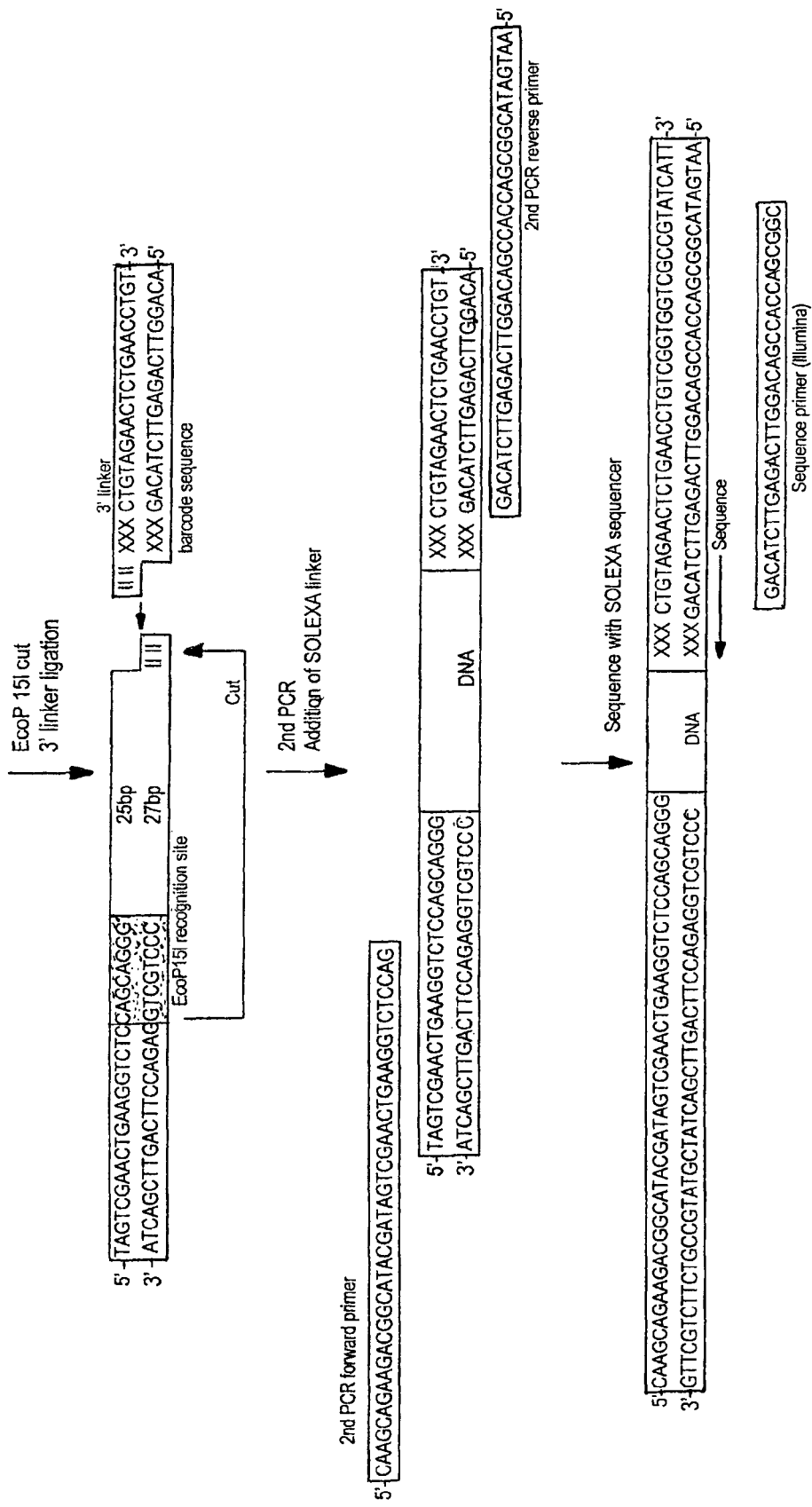

FIG. 51 shows a strategy of determining the 5' end side sequence of RNA used as the single-stranded template nucleic acid by sequencing from the 3' end side to the 5' end side the double-stranded nucleic acids in the mixture of amplified double-stranded nucleic acids obtained by the method of the subject invention. (The sequences in the following scheme are: Oligonucleotide, SEQ ID NO: 1; Primer 1 and adapter 1, SEQ ID NO: 137; Primer 2 and adapter 2, nucleotides 1-23 of SEQ ID NO: 1; primer 3, SEQ ID NO: 5; 3' linker, nucleotides 20-39 of SEQ ID NO: 8; 2d PCR forward primer, SEQ ID NO: 43; 2nd PCR reverse primer, SEQ ID NO: 39; Sequence Primer (Illumina), nucleotides 8-39 of SEQ ID NO: 8).

Figure 52:
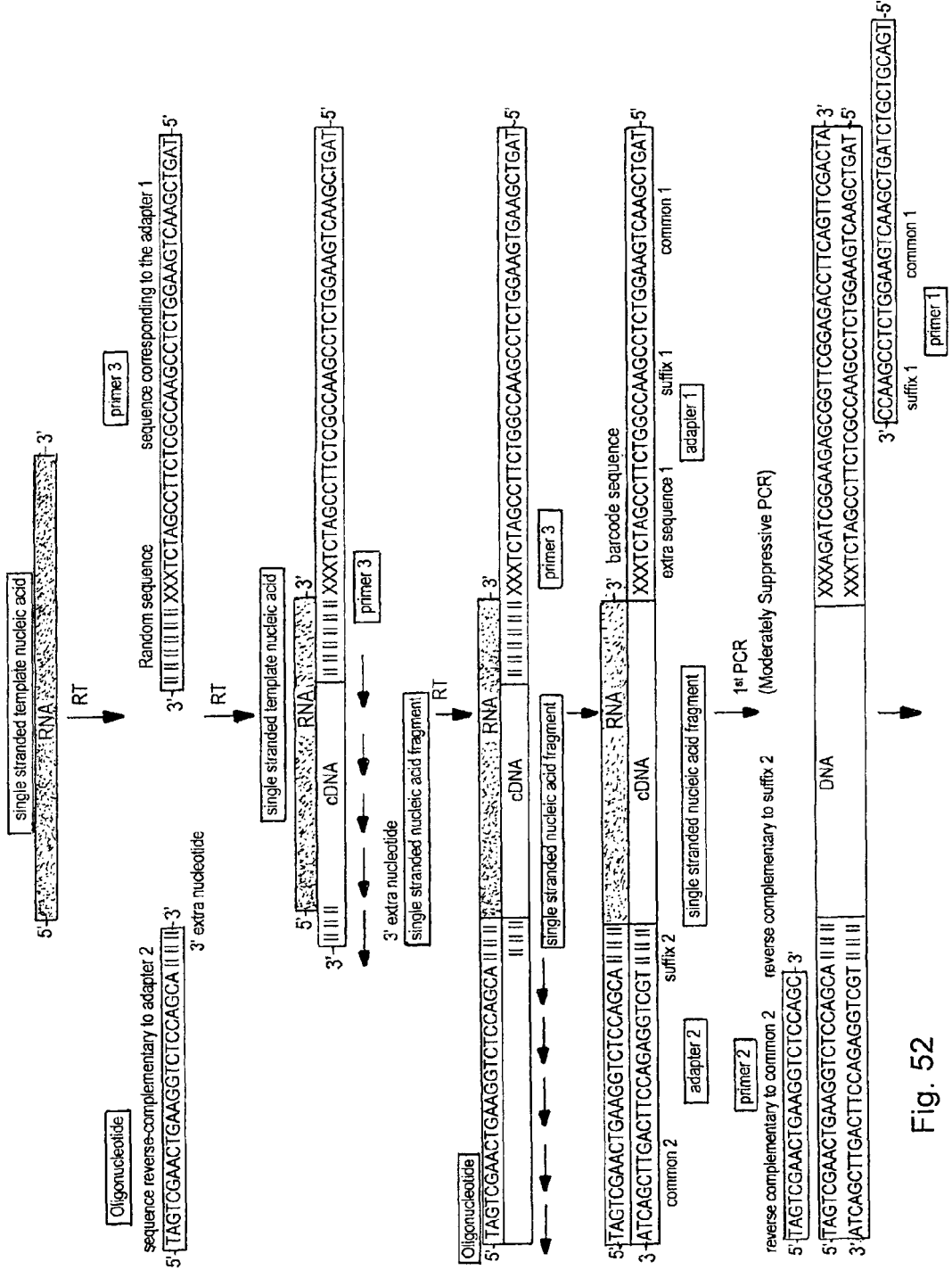
Figure 52:
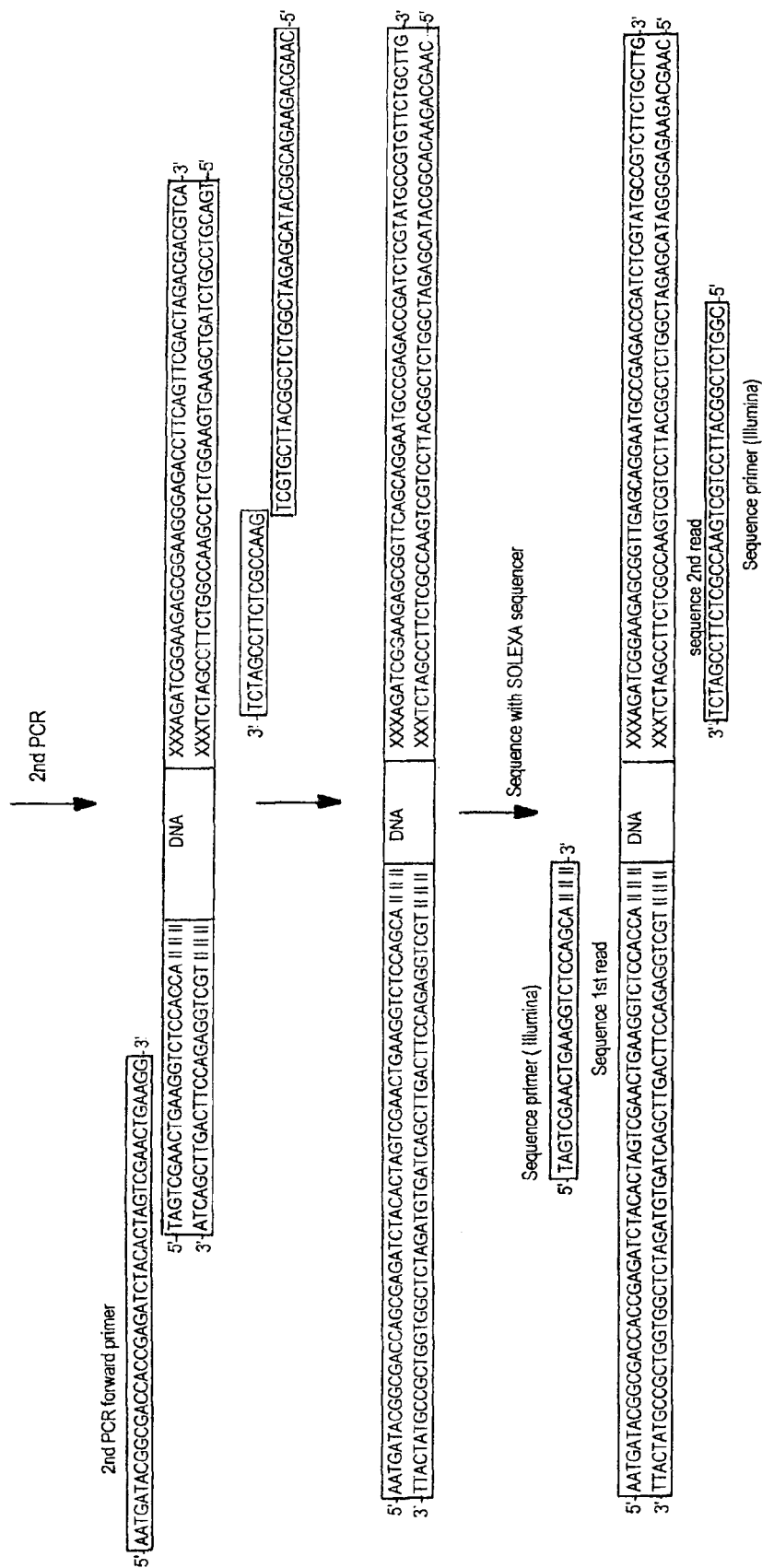

FIG. 52 shows a strategy of determining the 5' end side sequence of RNA used as the single-stranded template nucleic acid by sequencing from the 5' end side to the 3' end side or from both end side the double-stranded nucleic acids in the mixture of amplified double-stranded nucleic acids obtained by the method of the subject invention. (Oligonucleotide, nucleotides 1-24 of SEQ ID NO: 109; Primer 1, SEQ ID NO: 115, adapter 1, nucleotides 1-38 of SEQ ID NO: 110; Primer 2, nucleotides 1-23 of SEQ ID NO: 109; primer 3, SEQ ID NO: 110; adapter 2 complement of nucleotides 1-24 of SEQ ID NO: 109; 2d PCR forward primer, SEQ ID NO: 116; 2nd PCR reverse primer, SEQ ID NO: 117; Sequence Primer (Illumina) sequence first read, nucleotides 1-24 of SEQ ID NO: 109, Sequence Primer (Illumina) sequence second read, nucleotides 25-61 of SEQ ID NO: 117).

Figure 53:
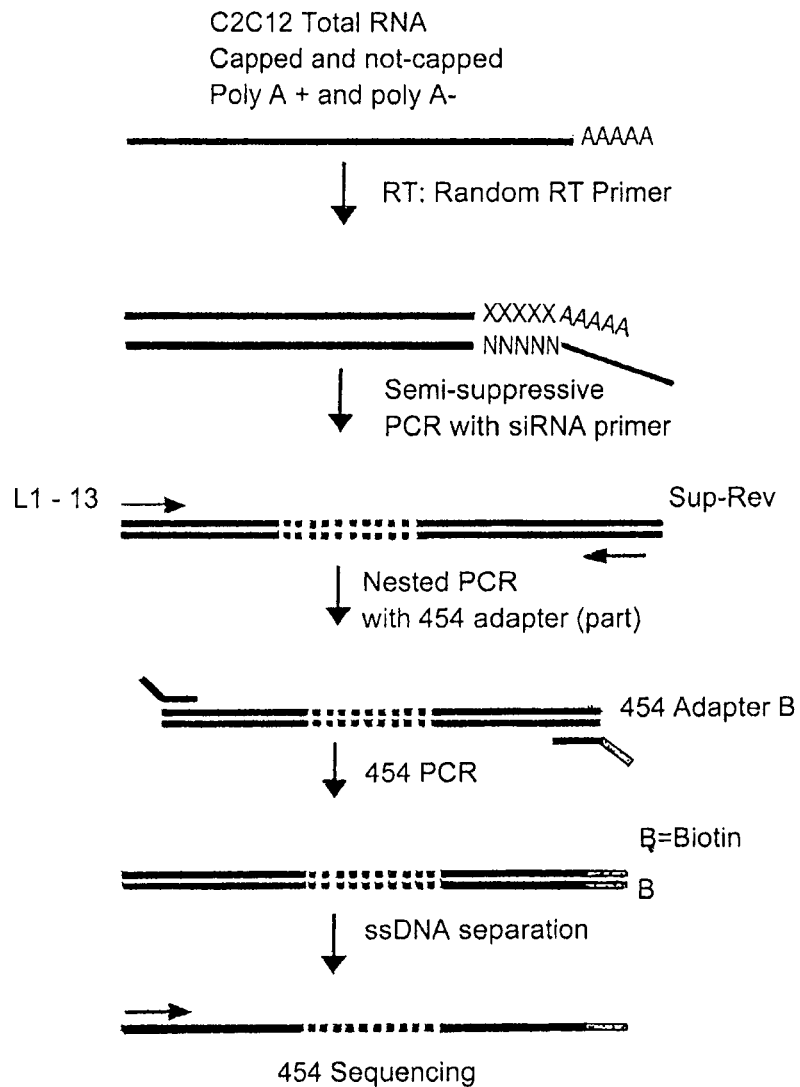

FIG. 53 shows an another strategy of determining the 5' end side sequence of RNA used as the single-stranded template nucleic acid by sequencing from the 5' end side to the 3' end side the double-stranded nucleic acids in the mixture of amplified double-stranded nucleic acids obtained by the method of the subject invention.

DESCRIPTIONS OF THE EMBODIMENTS

The subject invention relates to a method of manufacturing a mixture of amplified double-stranded nucleic acids.

The method of the subject invention comprises (a) preparing a single-stranded nucleic acid comprising a single-stranded adapter 1, a single-stranded nucleic acid fragment and a single-stranded adapter 2, and (b) conducting PCR with the single-stranded nucleic acid prepared in step (a). Example of the single-stranded nucleic acid is one comprising the single-stranded adapter 1, the single-stranded nucleic acid fragment and the single-stranded adapter 2 in 5' to 3' direction.

In step (a), the single-stranded adapter 1 comprises a common sequence 1 and a suffix sequence 1, the single-stranded adapter 2 comprises a common sequence 2 and a suffix sequence 2. The common sequence 1 and the common sequence 2 are reverse-complementary. The suffix sequence 1 and the suffix sequence 2 are not reverse-complementary. Example of the single-stranded adapter 1 is one comprising the common sequence 1 and the suffix sequence 1 in 5' to 3' direction, example of the single-stranded adapter 2 is one comprising the suffix sequence 2 and the common sequence 2 in 5' to 3' direction, In step (b), a primer 1 comprising a part of the common sequence 1 and the suffix sequence 1, and a primer 2 reverse-complementary to a part of the common sequence 2 and the suffix sequence 2 are used to amplify double-stranded nucleic acids. In the embodiments herein, the primer 1 is being referred to as "reverse PCR primer" in moderately suppressive PCR, and the primer 2 is being referred to as "forward PCR primer" in the moderately suppressive PCR.

The single-stranded nucleic acid fragment either comprises a target sequence or consists of a target sequence. The target sequence is a desired sequence to be amplified in the mixture of amplified double-stranded nucleic acids. Examples of the target sequence include sequence of 5' end side of RNA which is of a special interest in biology and is not the product of the truncation of a longer RNA molecule during the experiment.

The common sequence 1 and the common sequence 2 have the same nucleotide length and the nucleotide length is preferably in a range of from 10 to 40, more preferably is in a range of from 15 to 30, still more preferably is in a range of from 20 to 30. This is because in step (b), the nucleotide length of the common sequences 1 and 2 in the above range allows the common sequences 1 and 2 to hybridize with each other.

The common sequence 1 is reverse-complementary the common sequence 2. The reason why the nucleotide sequences of the common sequences 1 and 2 are in the above relation is that the common sequences 1 and 2 can hybridize with each other in step (b). Examples of the common sequence 1 and the common sequence 2 are ones that are the same nucleotide length, but nucleotide sequence in 5' to 3' direction of the common sequence 1 is complementary to nucleotide sequence in 3' to 5' direction of the common sequence 2.

The common sequence 1 and the common sequence 2 may form a restriction site(s) when annealed, and the number thereof can be one, two, three, four or more.

The suffix sequence 1 and the suffix sequence 2 have the same nucleotide length and the nucleotide length is preferably in a range of from 2 to 10, more preferably is in a range of from 2 to 5, still more preferably is 3 or 4. This is because the nucleotide length of the suffix sequences 1 and 2 in the above range can moderately suppress PCR of step (b), as stated below.

Nucleotide sequence of the suffix sequence 1 is not reverse-complementary to the suffix sequence 2. The reason why the nucleotide sequence directions of the suffix sequences 1 and 2 are in the above relation is that the suffix sequences 1 and 2 cannot hybridize with each other in step (b). Examples of the suffix sequence 1 and the suffix sequence 2 are ones that are the same nucleotide length, but nucleotide sequence in 5' to 3' direction of the suffix sequence 1 is not complementary to nucleotide sequence in 3' to 5' direction of the suffix sequence 2.

The adapter 1 preferably comprises a prefix sequence 1 at 5' end of the adapter 1 and the adapter 2 preferably comprises a prefix sequence 2 at 3' end of the adapter 2. The prefix sequences 1 and 2 have the same or different nucleotide length and the nucleotide lengths are independently and preferably in a range of from 1 to 25, more preferably are from 5 to 20, still more preferably is from 5 to 15. This is because the nucleotide length of the prefix sequences 1 and 2 in the above range can moderately suppress PCR of step (b) together with the suffix sequences 1 and 2.

It is preferable that the nucleotide sequence in of the prefix sequence 1 is not reverse-complementary to nucleotide sequence of the prefix sequence 2 to distinguish the prefix sequences 1 and 2 from the common sequences 1 and 2.

In a case where the adapter 1 comprises the common sequence 1 and the suffix sequence 1, the nucleotide length of the adapter 1 is preferably about 12 to 50, more preferably 20 to 40. In a case where the adapter 1 comprises the common sequence 1, the suffix sequence 1 and the prefix sequence 1, the nucleotide length of the adapter 1 is preferably about 13 to 75, more preferably 25 to 50. The same is true of the adapter 2. This is because in step (b), the nucleotide length of the adapter 1 in the above range allows the adapter 1 to hybridize with the primer 1.

FIG. 49 is an example of the single-stranded nucleic acid where the adapter 1 (nucleotides 1-33 of SEQ ID NO: 2) comprises the prefix sequence 1.

As described below, preparation of the single-stranded nucleic acid in step (a) preferably comprises attaching a sequence reverse-complementary to the adapter 2 (the complement of SEQ ID NO: 4) to 5' end of a single-stranded template nucleic acid comprising a sequence reverse-complementary to the single-stranded nucleic acid fragment, and conducting nucleic acid strand synthesis reaction with a primer comprising both the adapter 1 at 5' end side thereof and a sequence complementary to at least a part of the single-stranded nucleic acid fragment at 3' end thereof. However, there is no intention to limit the present invention to the above mode.

The adapter 2 is preferably introduced through the tail of an oligonucleotide (e.g. also referred to as "strand-switching oligonucleotide" and "TS oligo" herein) and the adapter 1 is preferably introduced through the tail of a primer 3 by means of nucleic acid strand synthesis reaction such as reverse transcription reaction using the CAPswitch method. In the embodiments herein, the primer 3 is being referred to as "random RT primer" in the moderately suppressive PCR. For example, in a case where the single-stranded template nucleic acid comprising a sequence complementary to the single-stranded nucleic acid fragment has a cap structure such as 7-methylguanosine caps at 5' end thereof, or one or more extra 3'-ribonucleotide such as 3'-cytidine at 5' end thereof, said step (a) can comprise nucleic acid strand synthesis reaction using the single-stranded template nucleic acid; an oligonucleotide comprising at 3' end thereof at least one nucleotide that can hybridize to the extra 3'-ribonucleotide at 3' end of the single-stranded nucleic acid fragment, a sequence reverse-complementary to the adapter 2, and the primer 3 comprising at least a random sequence or an oligo-T at 3' end thereof and a sequence corresponding to the adapter 1. In the case where the single-stranded template nucleic acid has 7-methylguanosine cap(s) or adenosine cap(s), example of the step (a) comprises reverse transcription reaction using RNA comprising a sequence complementary to the single-stranded nucleic acid fragment, the oligonucleotide comprising at least an oligo-riboguanosine or an oligo-riboadenosine at 3' end thereof and a sequence reverse-complementary to the adapter 2, and the primer 3 comprising at least a random sequence or an oligo-T at 3' end thereof and a sequence corresponding to the adapter 1.

FIG. 50 shows an example of step (a) where the primer 3 comprises nucleotides 1-33 of SEQ ID NO: 2 with random sequence at 3' end thereof and the oligonucleotide comprises SEQ ID NO: 4 with oligo-riboguanosine at 3' end thereof. The sequences of the oligonucleotide, the adapters and primer below are: oligonucleotide, SEQ ID NO: 4 with oligo-riboguanosine at 3' end thereof; Adapter 1 and Primer 1, nucleotides 1-33 of SEQ ID NO: 2; Primer 2, SEQ ID NO: 4; Adapter 2, the complement of SEQ ID NO: 4; primer 3, nucleotides 1-33 of SEQ ID NO: 2.

In the above case, the reverse transcriptase reaches 3' end of RNA in course of reverse transcription reaction with the primer 3 and then the reverse transcribed cDNA that is complementary to RNA adds some extra cytosine residues to 3' end of the cDNA if a cap is present at 5' end of RNA. The oligonucleotide having some guanine residues at 3' end thereof can hybridize with the extra cytosine residues added to RNA. This hybrid is then extended by the reverse transcription reaction. The remarkable point is that the above oligonucleotide hybridizes with the first strand cDNA, not with RNA.

The oligo-riboguanosine and the oligo-riboadenosine mean a sequence consisting of consecutive riboguanosine or riboadenosine residues. In the oligonucleotide, the use of the oligo-riboguanosine or the oligo-riboadenosine depends on 5' end modification of the single-stranded template nucleic acid. When the modification is a cap, the oligo-riboguanosine can be employed. When the modification is an ADP moiety, the oligo-riboadenosine can be employed.

The random sequence consists of a random sequence and the oligo-T consists of consecutive thymine residues sequence, which can specifically hybridize with a part of the single-stranded template nucleic acid.

The primer 1 used in step (b) comprises both a part of the common sequence 1 and the whole suffix sequence 1. The primer 1 preferably comprises the prefix sequence 1 at 5' end thereof. Whenever the adapter 1 comprises the prefix sequence 1, the primer 1 comprises the prefix sequence 1. However, when the primer 1 comprises the prefix sequence 1, the adapter 1 may be a sequence not comprising the prefix sequence 1.

The primer 2 used in step (b) comprises a sequence reverse-complementary to a part of the common sequence 2 and a sequence reverse-complementary to the whole suffix sequence 2, and preferably comprises a sequence reverse-complementary to the prefix sequence 2 at 5' end thereof. Whenever the adapter 2 comprises the prefix sequence 2, the primer 2 comprises a sequence reverse-complementary to the prefix sequence 2. However, when the primer 2 comprises a sequence reverse-complementary to the prefix sequence 2, the adapter 2 may be a sequence not comprising the prefix sequence 2.

Figure 7:
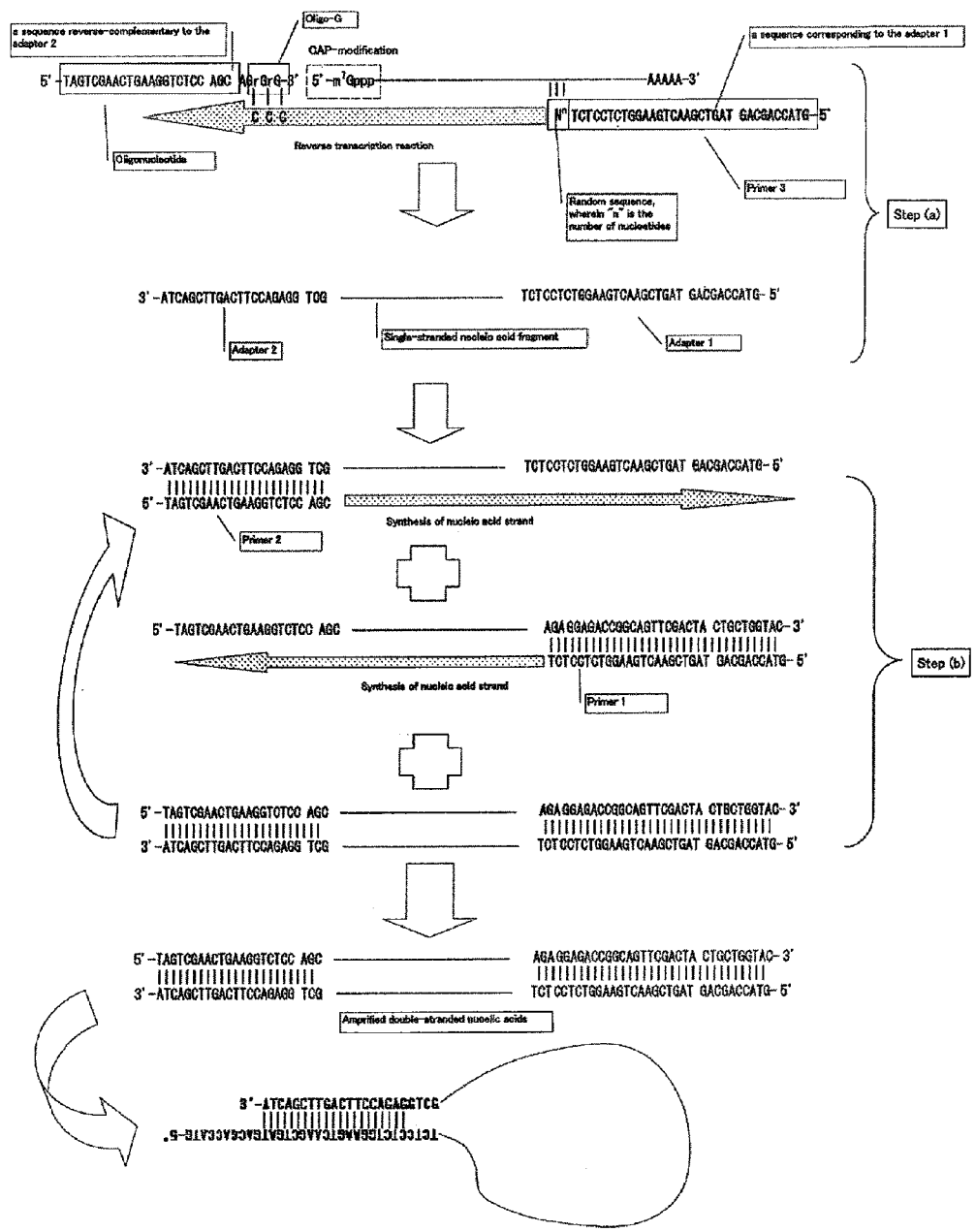
FIG. 7 shows an example of the method of the subject invention comprising step (a) and step (b) where the single-stranded template nucleic acid is RNA; the nucleic acid strand synthesis reaction is reverse transcription reaction; the primer 3 comprises nucleotides 1-33 of SEQ ID NO: 2 with random sequence at 3' end thereof; and the oligonucleotide (SEQ ID NO: 4) comprises oligo-riboguanosine at 3' end thereof. The sequences of the adapters and primer are: Adapter 1 and Primer 1, nucleotides 1-33 of SEQ ID NO: 2; Primer 2, SEQ ID NO: 4; Adapter 2, the complement of SEQ ID NO: 4.

FIG. 7 shows as example of the method of the subject invention comprising step (a) and step (b) where the single-stranded template nucleic acid is RNA; the nucleic acid strand synthesis reaction is reverse transcription reaction; the primer 3 comprises random sequence at 3' end thereof; and the oligonucleotide comprises oligo-riboguanosine at 3' end thereof.

The PCR conducted in step (b) can carried out under the general PCR conditions such as 5 min 95° C., n×(10 s at 95° C., 15 s at 65° C., 6 min at 68° C.) and using hot start, wherein n represents the number of cycles, for example 30.

In the PCR, a sequence reverse-complementary to the single-stranded nucleic acid is extended starting from the primer 1 hybridized with the single-stranded nucleic acid as a template to obtain a double-stranded nucleic acid. The double-stranded nucleic acid is then amplified by using the primer 1 and the primer 2 under the general conditions. The PCR conditions can be modified optimally in view of the nucleotide length and sequence of the sequence to amplify.

Figure 1:
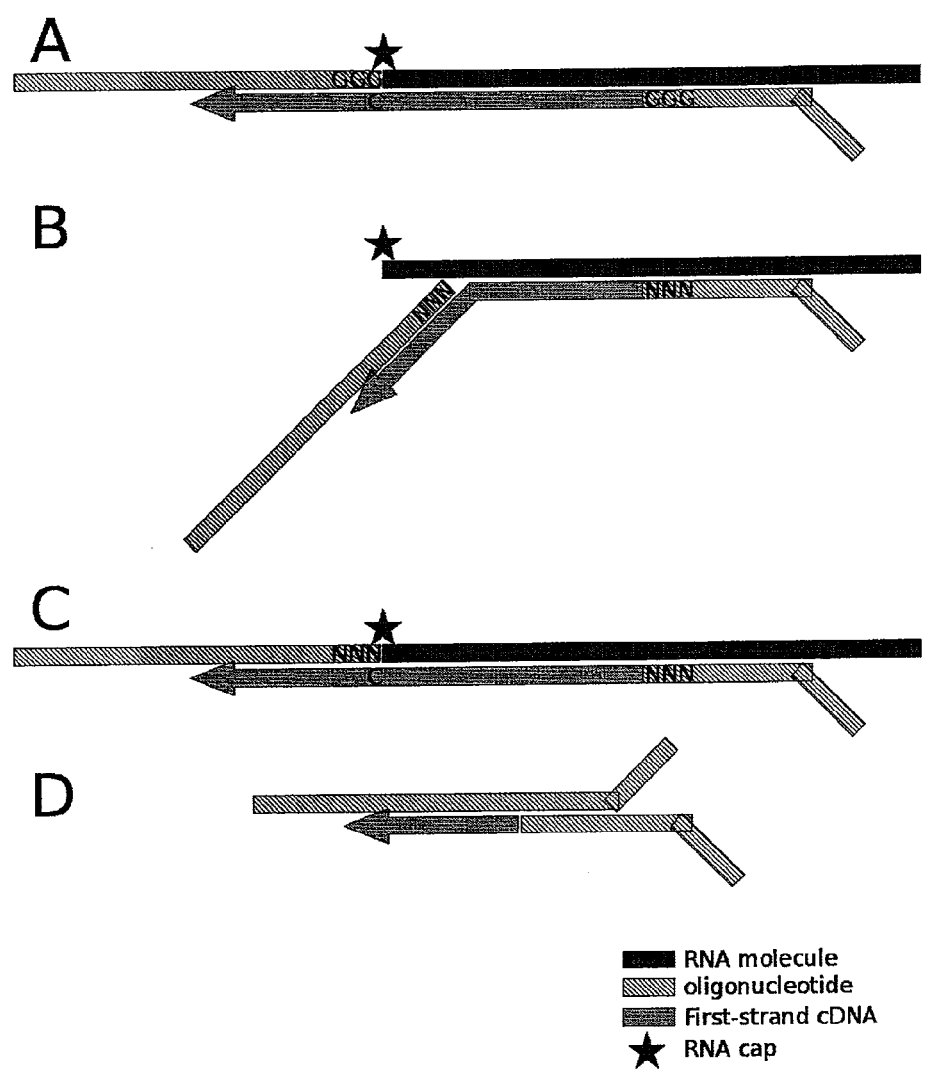
FIG. 1 shows artifacts produced by the CAPswitch method of Chenchik et al.
Figure 2:
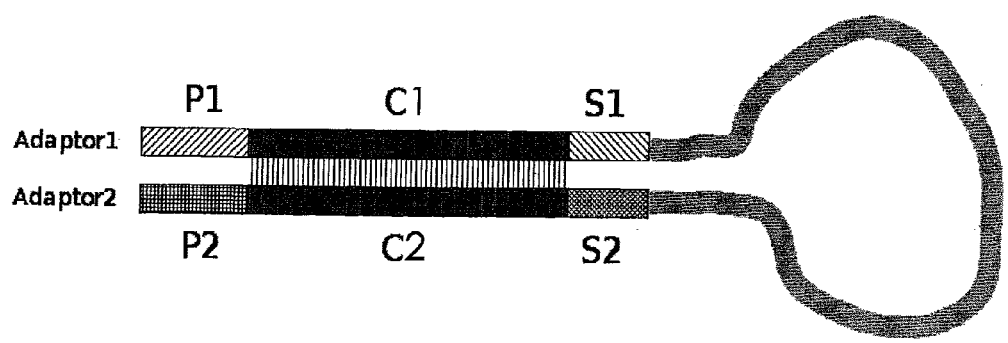
FIG. 2 shows the method of the subject invention using two adapters that are partially complementary. The method of the subject invention uses two adapters that are partially complementary.

FIG. 2 shows the single-stranded nucleic acid prepared by step (a) in the method of the subject invention. C1 and C2 represent the common sequences 1 and 2, respectively. S1 and S2 represent the suffix sequences 1 and 2, respectively. P1 and P2 represent the prefix sequences 1 and 2, respectively. As described in FIG. 2, during the amplification by PCR, the complementarity of 5' and 3' ends of the single-stranded nucleic acid flanked by the adapter 1 and the adapter 2 corresponds to the length of the common sequence.

Figure 3:
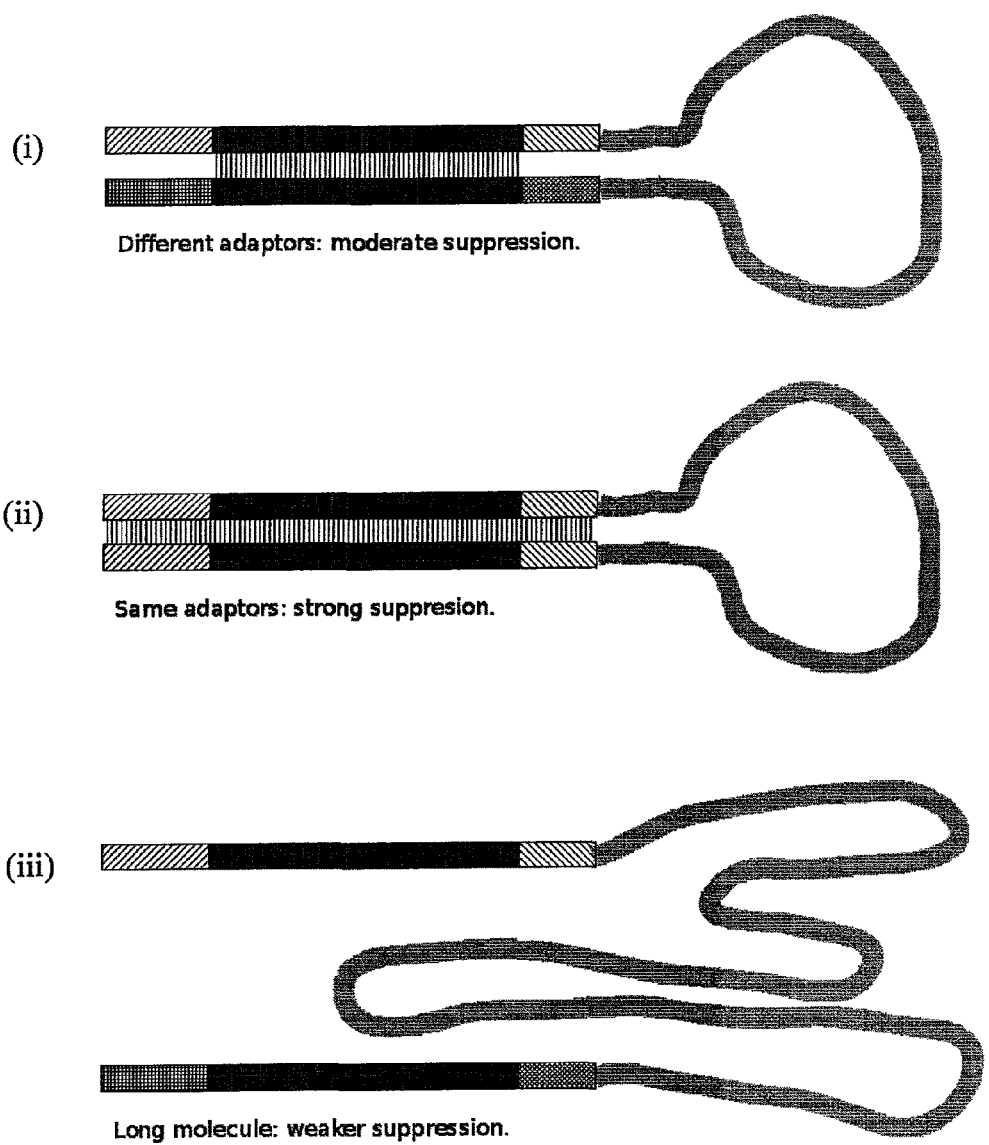
FIG. 3 shows the suppression effect caused by various combinations of the adaptors. The suppression is the weakest for the long molecules that have a different adapter at each end. "Moderate suppression" means that the suppressive effect is detectable (for instance, there are no cDNAs smaller than 200 bp on the gel pictures), but will be weaker compared to the case of "strong suppression". The consequence of this is that during the course of the polymerase chain reaction, the "moderately suppressed" molecules will be preferentially amplified.

FIG. 3 shows three types of the single-stranded nucleic acids that can be prepared by step (a) in the method of the subject invention. Item (i) of FIG. 3 shows the single-stranded nucleic acid flanked by different adapters, the adapter 1 and the adapter 2. In this case, the single-stranded nucleic acid is moderately suppressed in course of step (b) depending on the nucleotide lengths of the single-stranded nucleic acid fragment and the common sequence. For example, in a case where the nucleotide length of the single-stranded nucleic acid fragment is 200 bp and the nucleotide length of the common sequences 1 and 2 is 20 bp, no cDNA that is smaller than 200 bp will be detectable after step (b). Item (ii) of FIG. 3 shows the single-stranded nucleic acid flanked by the same adapters, two adapters 1 or two adapters 2. The suppression effect of item (ii) can be stronger than that of item (i) since the complementarity spans the length of the adapter 1 or the adapter 2 which is always longer than the common sequence alone. Therefore, the amplification of the single-stranded nucleic acid flanked by the adapter 1 and the adapter 2 is superior to the amplification of the single-stranded nucleic acid flanked by two copies of the same adapter. In a case as shown in item (iii) where the nucleotide length of the single-stranded nucleic acid fragment is much longer, the suppression effect of the single-stranded nucleic acid fragment flanked by the different adapters is the weakest.

The single-stranded adapter 1 may comprise an additional sequence, named extra sequence 1, at 3' end of the suffix sequence 1. As well, the single-stranded adapter 2 may comprise an extra sequence 2 at 3' end of the suffix sequence 2, regardless of whether the single-stranded adapter 1 comprises the extra sequence 1 or not. The extra sequences 1 and/or 2 can hybridize with a primer used in order to sequence the single-stranded nucleic acid fragment by using methods known to persons having ordinary skills in the art. Each length of the extra sequences 1 and 2 is one capable of hybridizing with the primer under the condition of annealing step in a general PCR, which is such as, but not limited to, 15 to 30 bp.

The method of the subject invention is that the dimers that contain any combination of the adapters can be also suppressed. Although the adapter 1 and the adapter 2 are not fully complementary, they share the common sequence (see FIG. 2) so that the great proximity of their 5' and 3' end strongly increases the formation of intramolecular complexes that can not be amplified by PCR (see FIG. 3 (*ii*)).

The method of the subject invention allows in a single reaction the suppression of the smallest single-stranded nucleic acid and the discrimination of the single-stranded nucleic acid that is flanked by two identical adapters. This was not possible in suppressive PCR published by Chenchick et al.

Figure 4:
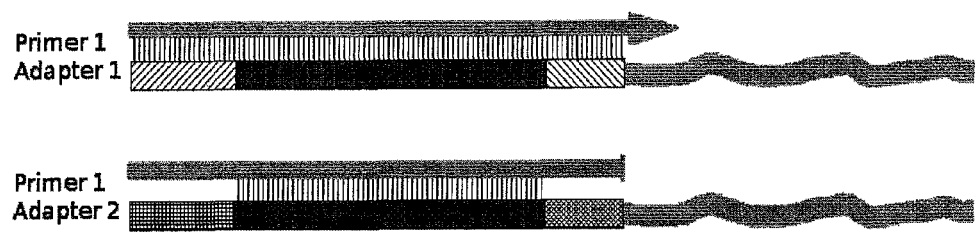
FIG. 4 shows two types of adapter identity. Adapter identity is maintained during PCR because the PCR primers cannot be extended if they are annealed on the wrong adapter.

As shown in FIG. 4, the primer 1 binds to both the adapter 1 and the adapter 2. The primer 2 binds to the adapters 1 and 2 as well. For example, when the primer 1 is annealed on the adapter 1, the sequence complementary to the single-stranded nucleic acid can be extended starting from the primer 1 during PCR. However, in the other case where the primer 1 is annealed on the adapter 2, the above sequence cannot be extended during PCR because the primer 1 is not fully complementary to the adapter 2. The same is true to the combination of the primer 2 and the adapter 1.

In the worst scenario, the yield of an amplification during which half of the adapters are occupied by primers that do not allow the sequence complementary to the single-stranded nucleic acid to extend (because the suffix sequence 1 and the suffix sequence 2 mismatch) would be $(3/4)^n$ of a normal PCR, where n is the number of cycles. For 30 cycles, this is a reduction of more than 5000 times. However, by using an annealing temperature that is not too different from the melting temperature of nucleic acid duplexes of the common sequence, it is possible to let the primer 1 and the primer 2 compete efficiently for their best target sequence, and obtain an acceptable yield, while benefiting of the suppressive and discriminative advantages of the suppressing PCR method.

The comparison of the method of the subject invention with suppressive PCR is shown in the following table.

TABLE 1

The comparison of the method of the subject invention vs. suppressive PCR

| | the method of the subject invention | suppressive PCR |
|---|---|---|
| Moderation of suppression | According to size and combination of adapters. | According to size. |
| Circumstance of molecule to be suppressed | All molecules | Only molecules with the same adapter on both ends. |
| length of molecule to be suppressed | All sizes | All sizes (if subjected to suppression). |
| Suppression for molecules that use two different adapters (to keep directionality). | Yes | No |

As shown in Table 1, the method of the subject invention is superior to suppressive PCR in terms of the moderate of suppression, the circumstance and length of molecule to be suppressed, and the suppression for molecules that use two different adapters. Furthermore, the method of the subject invention can suppress amplification of primer dimers, resulting in amplifying a small quantity of RNA e.g. polysomal poly A– RNA, which cannot be analyzed with CAGE.

Surprisingly, the method of the subject invention can keep directionality and suppress small artifacts that cannot be achieved by suppressive PCR.

The use of the primers 1 and 2 that match the common sequence at 5' end side and the suffix sequence at 3' end side in the method of the subject invention is very innovative. This is because taking into consideration suppressive PCR, it is even recommended that the PCR primers match only the 5' half or the common sequence but not the whole primer.

The method of the subject invention can provide double-stranded cDNA comprising a sequence corresponding to a 5' end side sequence of RNA. Therefore, the 5' end side sequence of RNA that is used as the single-stranded template nucleic acid can be determined by sequencing the double-stranded nucleic acids in the mixture of amplified double-stranded nucleic acids obtained by the method of the subject invention. the sequencing of the double-stranded nucleic acids can be carried out (i) from 3' end side to 5' end side, (ii) from 5' end side to 3' end side, or (iii) simultaneously from both 3' and 5' end sides by means of the methods known to those skilled in the art.

The embodiments of the above (i) are being shown in the following Examples 1 to 8. The embodiments of the above (ii) are being shown in the following Examples 9 and 11. Furthermore, the embodiment of the above (iii) is being shown in the following Example 10.

The method for determining the 5' end side sequence of RNA in the case of the above (i) may comprise moderately suppressive PCR followed by, but not limited to, the steps of cleavage of the 3' end sides of the double-stranded nucleic acids with a restriction enzyme such as, but not limited to, EcoP15I; ligation of an adapter at the cleavage site; 2nd PCR; exonuclease treatment; and then sequencing the double-stranded nucleic acids obtained as the 2nd PCR production. The method for determining the 5' end side sequence of RNA in the case of the above (ii) may comprise moderately suppressive PCR followed by, but not limited to, the steps of 2nd PCR or inner 3' RACE, 454 adapter PCR, and then sequencing the double-stranded nucleic acids obtained as the 454 adapter PCR production. The method for determining the 5' end side sequence of RNA in the case of the above (iii) may comprise moderately suppressive PCR followed by, but not limited to, the steps of 2nd PCR, and then sequencing the double-stranded nucleic acids obtained as the 2nd PCR production. As well, the method for determining the 5' end side sequence of RNA in each case of the above (i) to (iii) may comprise moderately suppressive PCR followed by the known method such as, but not limited to, the method for utilizing the 5' end of mRNA for cloning and analysis disclosed in WO 03/106672, including sequencing the double-stranded nucleic acids.

FIG. 51 shows a strategy of determining the 5' end side sequence of RNA used as the single-stranded template nucleic acid by sequencing from 3' end side to 5' end side the double-stranded nucleic acids in the mixture of amplified double-stranded nucleic acids obtained by the method of the subject invention (The sequences in the following scheme are: Oligonucleotide, SEQ ID NO: 1; Primer 1 and adapter 1, SEQ ID NO: 137; Primer 2 and adapter 2, nucleotides 1-23 of SEQ ID NO: 1; primer 3, SEQ ID NO: 5; 3' linker, nucleotides 20-39 of SEQ ID NO: 8; 2d PCR forward primer, SEQ ID NO: 43; $2^{nd}$ PCR reverse primer, SEQ ID NO: 39; Sequence Primer (Illumina), nucleotides 8-39 of SEQ ID NO: 8).

FIG. 52 shows a strategy of determining the 5' end side sequence of RNA used as the single-stranded template nucleic acid by sequencing from 5' end side to 3' end side or from both end side the double-stranded nucleic acids in the mixture of amplified double-stranded nucleic acids obtained by the method of the subject invention. (Oligonucleotide, nucleotides 1-24 of SEQ ID NO: 109; Primer 1, SEQ ID NO: 115, adapter 1, nucleotides 1-38 of SEQ ID NO: 110; Primer 2, nucleotides 1-23 of SEQ ID NO: 109; primer 3, SEQ ID NO: 110; adapter 2 complement of nucleotides 1-24 of SEQ ID NO: 109; 2d PCR forward primer, SEQ ID NO: 116; $2^{nd}$ PCR reverse primer, SEQ ID NO: 117; Sequence Primer (Illumina) sequence first read, nucleotides 1-24 of SEQ ID NO: 109, Sequence Primer (Illumina) sequence second read, nucleotides 25-61 of SEQ ID NO: 117).

FIG. 53 shows an another strategy of determining the 5' end side sequence of RNA used as the single-stranded template nucleic acid by sequencing from 5' end side to 3' end side the double-stranded nucleic acids in the mixture of amplified double-stranded nucleic acids obtained by the method of the subject invention.

According to the method of the subject invention, a reverse transcription reaction is executed with RNA as a single-stranded template nucleic acid, the oligonucleotide, and the primer 3 to produce the single-stranded nucleic acid comprising the adapters 1 and 2 as well as cDNA complementary to RNA. Moderately-suppressive PCR is then conducted with the single-stranded nucleic acid as a template as well as the primers 1 and 2 to amplify the double-stranded nucleic acids. Optionally, there may be additional PCRs such as, but not limited to, nested PCR and 454 PCR and the other treatments suitable for the following sequencing. As the result, the sequence can be determined by carrying out the sequencing with the methods known by those skilled in the art such as, but not limited to, 454 Sequencing.

Each of the sequencings in the case of the above (i) to (iii) has benefits different from each other. For example, in this case, no protocol to make 3' RACE analysis with random primers would be used. As well, the sequencing of the double-stranded nucleic acids from both 5' and 3' end sides at the same time can analyze inner exons with a shorter protocol that does not involve tag cleavage and amplification.

EXAMPLES

Example 1

The presented method is embodied in the following protocol, used create a library of 5' end sequence tags (CAGE tags, [Shiraki 2003, the disclosure of which h is herein incorporated by reference in its entirety.]) suitable for direct sequencing with Illumina-Solexa platform.

Figure 5:
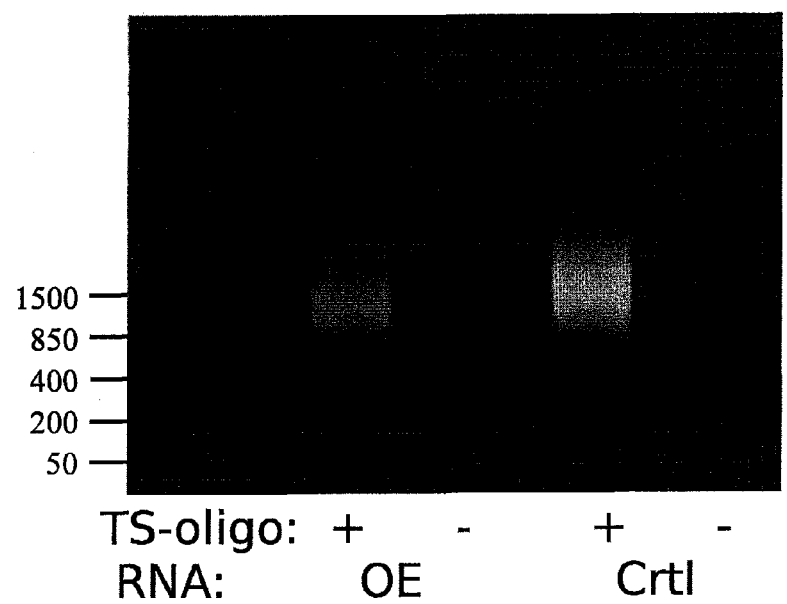
FIG. 5 shows the results of Example 1 demonstrating 5' cDNAs amplified by moderately suppressive PCR after reverse transcription using the CAPswitch method. 5' cDNAs amplified by moderately suppressive PCR after reverse transcription using the CAPswitch method. As a control, the template-switching oligonucleotides were omitted in some reactions. The RNA used during reverse-transcription was either extracted from the mouse olfactory epithelium (OE), or mouse embryos (Ctrl).

5 to 10 ng of total RNA microdissected from fixed cryostat histrological sections were heat-denatured at 65° C. for 10 min in a final volume of 5 μl with 50 pmol of strand-switching oligonucleotide (TAGTCGAACTGAAGGTCTCCAGCArGrGrG wherein rG shows riboguanosine) (SEQ ID NO:1), 10 pmol of random RT primer (GTACCAGCAGTAGTC-GAACTGAAGGTCTCCTCTN$_{15}$) (SEQ ID NO: 2), 10 pmol of polythimine RT primer (GTACCAGCAGTAGTC-GAACTGAAGGTCTCCTCT$_{18}$) (SEQ ID NO: 3) and then transferred quickly on ice/water mix. RT was accomplished in a volume of 20 μl adding the following components to reach these final concentrations: 1× first strand buffer (Invitrogen), 0.5 mM dNTPs (TaKaRa), 1 mM DTT (Invitrogen), 0.75 M betaine (WAKO), 0.41 M D-Threalose (Nacalai Tesque), 3.4% D-Sorbitol (WAKO) and 400 units of SuperScripth (Invitrogen), and incubated at 12 C for 10 min, 50 C for 45 min, 75° C. for 10 min in a MWG thermocycler. The tubes were then immediately transferred on ice/water mix. For the second strand synthesis a small scale moderately suppressive PCR reaction was performed to evaluate the optimal number of cycles, defined as the last cycle before the intensity of the product ceases to increase. 10 μl aliquotes were taken every two cycles and analyzed on 1 agarose gel. 2 μl of first strand cDNA were amplified in a total volume of 100 μl using a mixture containing 1× ExTaq Buffer (TaKaRa), 250 μM dNTPs (TaKaRa), 100 nM forward PCR primer (TAGTCGAACTGAAGGTCTCCAGC) (SEQ ID NO: 4), 100 nM reverse PCR primer (GTACCAGCAGTAGTC-GAACTGAAGGT CTCCTCT) (SEQ ID NO: 5), and 5 units of ExTaq (TaKaRa) with the following PCR program 5 min 95° C., n×(10 s at 95° C., 15 s at 65° C., 6 min at 68° C.) and using hot start (FIG. 5). A large scale moderately suppressive PCR preparation using all the first-strand cDNA (180) was performed in 9 reactions of 100 μl. PCR products were cleaned using Qiaquick PCR purification columns (Qiagen) and all of them were pooled together.

Half of the pooled cDNA was digested in 4 reactions of 300 μl each, using 150 units of EcoP15I (NEB), 1× buffer 3 (NEB), 1 mM ATP (NEB), 1×BSA (NEB) incubated at 37° C. for 4 hours. The low molecular weight cleavage products were purified through the Microcon YM-100 membranes (Millipore) and the flow-through was concentrated on Microcon YM-10 (Millipore) according to the manufacturer's instructions. Equimolar amounts of the teo oligonucleotides (NNAGCTGTAGAACTCTGAACCTGT (SEQ ID NO: 6) and ACAGGTTCAGAGTTCTACAGCT (SEQ ID NO: 7)), were annealed in a water bath heated at 95° C. and left to cool down to room temperature. to form ligation adapters. 2 μM adapters were ligated to 15 μl of the EcoP15I cleavage products 1200 units of T4 DNA ligase (NEB) in 30 μl and incubated for 16 hours at 16° C. in a water bath. Optimal number of cycles for the ligation product to be amplified was determined by PCR with 5 μM of forward PCR primer (AAT-GATACGGCGACCACC GACAGGTTCAGAGTTCTA-CAG) (SEQ ID NO: 8), 5 μM of reverse PCR primer (CAAGCAGAAGACGGrCATACGATAGTC-GAACTGAAGGTCTCCAG) (SEQ ID NO: 9), 1× ExTaq buffer (TaKaRa), 200 μM dNTPs (TaKaRa), 5 units of ExTaq (TaKaRa). The program was 5 min 95° C., n×(20 s at 95 C, 20 s at 57 C, 20 s at 68 C). 6 PCR reactions in 100 μl for each sample were performed.

The excess of the primers was digested with 20 units of Exonuclease I (TaKaRa) at 37° C. for 30 min and then the enzyme was heat inactivated at 55° C. for 15 min. Then the PCR products were purified by electrophoresis on 10% polyacrylamide gel and the band corresponding to the expected size (112 base pairs) was cut, passed through a syringe to break the structure of polyacrylamide and the DNA was extracted at R.T. in microtube on rotation with 800 μl of 1×TE buffer over night. The tubes were centrifuged at 13,000 rpm for 10 min and the supernatant was collected. 600 μl of 1×TE buffer were added to the polyacrylamide in the microtube and let to rotate at room temperature for 1 hour. This step was repeated once more. Then for each sample, all the collected fractions were pooled together and passed through a Microspin filter (GE Healthcare) to eliminate residual traces of polyacrylamide. A total of 2 ml of filtrate was concentrated to 100 μl passing through a Microcon YM-10 column (Millipore), further purified using a Qiaquick PCR purification column (Qiagen) and eluted in 100 μl of EB buffer (10 mM Tris-HCl pH 8.5). The purity and the concentration of the sample was estimated by Nanodrop UV spectrophotometer and Agilent 2100 Bioanalyzer and an aliquot of 10 μl was analyzed by polyacrylamide gel electrophoresis to check for the correct size of the recovered DNA.

The library was sequenced using a Illumina-Solexa platform. 2,859,511 reads were recorded, and 2,535,405 CAGE tags were extracted. 33,558 were mapped to mouse ribosomal DNA and 2,316,861 to the mouse genome (assembly mm9). The most frequent tag mapped to the ubb gene on the chromosome 14 in the region 46,703,702-46,703,726 and was counted 18,116 times. The very low proportion of tags matching ribosomal sequences indicates that capped molecules were correctly discriminated from non-capped molecules like the very abundant 28 S and 18 S ribosomal RNAs. The tags identify many 5' ends, as exemplified by the tag GAGTGAC-GAGAGGCTTTGTCCGGTT (SEQ ID NO: 10) that matches with the 5' end of the ubb transcript, which encodes for the ubiquitin B protein, important for neuronal survival.

Example 2

In this experiment, total RNA from the hepatocellular carcinoma cell line Hep G2 (ATCC number HB-8065) was used to create CAGE tags by random priming.

Figure 6:
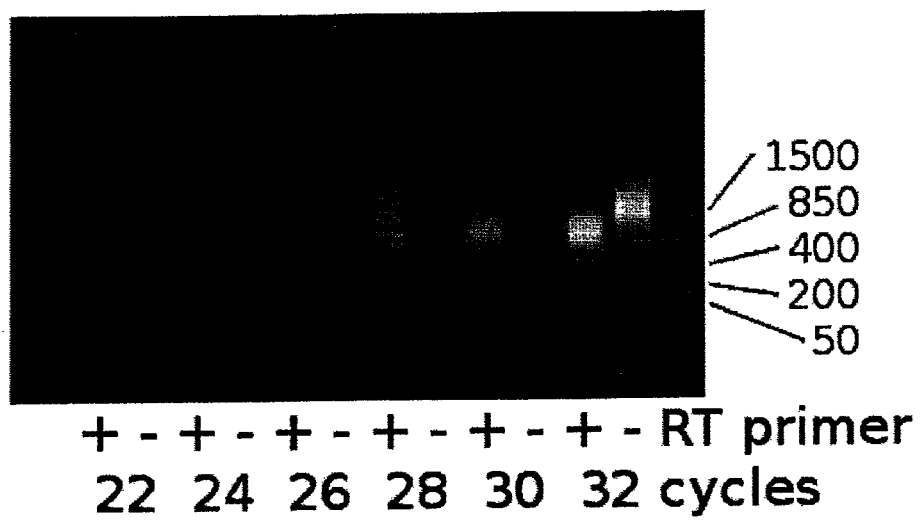
FIG. 6 shows the results of Example 2 demonstrating 5' cDNAs amplified by moderately suppressive PCR after reverse transcription using the CAPswitch method. 5' cDNAs amplified by moderately suppressive PCR after reverse transcription using the CAPswitch method. As a control, the reverse-transcription primers were omitted in some reactions. The PCR was monitored by taking aliquots every two cycles.

50 ng of total RNA were heat-denatured at 65° C. for 10 min in a final volume of 2 µl with 100 pmol of strand-switching oligonucleotide (TAGTCGAACTGAAGGTCTCCAG-CArGrGrG) (SEQ ID NO: 11) and 10 pmol of random RT primer (GTACCAGCAGTAGTCGAACTGAAG-GTCTCCTCTN$_{15}$) (SEQ ID NO: 12), in 1.62 µM D-Threalose (Nacalai Tesque) and 13.3% D-Sorbitol (WAKO) and then transferred quickly on ice/water mix. RT was accomplished in a volume of 10 µl adding the following components to reach these final concentrations: 1× first strand buffer (Invitrogen), 0.5 mM dNTPs (TaKaRa), 1 mM DTT (Invitrogen), 0.75 M betaine (WAKO) and 400 units of SuperScriptII (Invitrogen), and incubated at 22° C. for 10 min, 50° C. for 45 min, 75° C. for 10 min in a MWG thermocycler. The tubes were then immediately transferred on ice/water mix. For the second strand synthesis a small scale moderately suppressive PCR reaction was performed to evaluate the optimal number of cycles (FIG. 6). 5 µl aliquotes were taken every two cycles and analyzed on 1% agarose gel. 2 µl of first strand cDNA were amplified in a total volume of 100 µl using a mixture containing 1× ExTaq Buffer (TaKaRa), 250 µM dNTPs (TaKaRa), 100 nM forward PCR primer (TAGTCGAACT-GAAGGTCTCCAGC) (SEQ ID NO: 13), 100 nM reverse PCR primer (GTACCAGCAGTAGTCGAACTGAAG-GTCTCCTCT) (SEQ ID NO: 14), and 5 units of ExTaq (TaKaRa) with the following PCR program 5 min 95° C., n×(10 s at 95° C., 15 s at 65° C., 6 min at 68° C.) and using hot start. A large scale moderately suppressive PCR preparation using 2 µl of first-strand cDNA was performed in 1 reaction of 100 PCR products were cleaned using Qiaquick PCR purification columns (Qiagen), and recovered in 50 µl of EB buffer (Qiagen).

All the cDNAs were digested at 37° C. for 4 hours in a volume of 96 µl each, using 100 units of EcoP15I (NEB), 1× buffer 3 (NEB), 1 mM ATP (NEB), 1×BSA (NEB). The low molecular weight cleavage products were purified through the Microcon YM-100 membranes (Millipore) and the flow-through was concentrated on Microcon YM-10 (Millipore) according to the manufacturer's instructions. The two oligonucleotides NNACCCTGTAGAACTCTGAACCTGT (SEQ ID NO: 15) and ACAGGTTCAGAGT TCTACAGCT (SEQ ID NO: 16) were annealed in 10 µl at 1 mM each in a thermocycler heated at 95° C. and left to cool down to room temperature. to form ligation adapters. 1 pmol adapters were ligated to 10 µl of the EcoP15I cleavage products using 10 µl of Mighty Ligation Mix (TaKaRa) and incubated for 16 hours at 16° C. in a water bath. Optimal number of cycles for the ligation product to be amplified was determined by PCR with 5 µM of forward PCR primer (AATGATACGGCGACCACC GACAGGTTCAGAGTTCTACAG) (SEQ ID NO: 17), 5 µM of reverse PCR primer (CAAGCAGAAGACGGCATAC-GATAGTCGAACTGAAGGTCTCCAG) (SEQ ID NO: 18), 1× ExTaq buffer (TaKaRa), 200 µM dNTPs (TaKaRa), 5 units of ExTaq (TaKaRa) and 1 µl of ligation product. The program was 2 min 95° C., n×(10 s at 95° C., 10 s at 57° C.). For the large-scale amplification, 3×100 µl of PCR were performed with 1 µl of ligation product in each tube and 12 cycles.

The excess of the primers was digested with 20 units of Exonuclease I (TaKaRa) at 37° C. for 30 min and then the enzyme was heat inactivated at 55° C. for 15 min. Then the PCR products were purified by electrophoresis on 6% polyacrylamide gel and the band corresponding to the expected size (112 base pairs) was cut, passed through a syringe to break the structure of polyacrylamide and the DNA was extracted at R.T. in microtube on rotation with 800 µl of 1×TE buffer over night. The tubes were centrifuged at 13,000 rpm for 10 min and the supernatant was collected. 600 µl of 1×TE buffer were added to the polyacrylamide in the microtube and let to rotate at room temperature for 1 hour. This step was repeated once more. Then for each sample, all the collected fractions were pooled together and passed through a Microspin filter (GE Healthcare) to eliminate residual traces of polyacrylamide. A total of 2 ml of filtrate was concentrated to 100 µl passing through a Microcon YM-10 column (Millipore). The purity and the concentration of the sample was estimated by Nanodrop UV spectrophotometer and Agilent 2100 Bioanalyzer and an aliquot of 10 µl was analyzed by polyacrylamide gel electrophoresis to check for the correct size of the recovered DNA.

The library was sequenced using a Illumina-Solexa platform. 4,314,825 reads were recorded, and 1,972,665 CAGE tags were extracted. 215,933 were mapped to mouse ribosomal DNA and 1,458,717 to the mouse genome (assembly mm9). The most frequent tag mapped to the TF gene on the chromosome 3 in the region 134,947,926-134,947,950 and was counted 12,446 times. The very low proportion of tags matching ribosomal sequences indicates that capped molecules were correctly discriminated from non-capped molecules like the very abundant 28 S and 18 S ribosomal RNAs. The tags identify many 5' ends, as exemplified by the tag GACAGAAGCGAGTCCGACTGTGCTC (SEQ ID NO: 19) that matches with the 5' end of the TF transcript, which encodes for the transferrin protein, that is important for iron metabolism and abundant in liver.

Example 3

In this experiment, polysomal polyA-RNA from the K562 cell line (ATCC lot number 4607240) was used to create CAGE tags by random priming.

Figure 8:
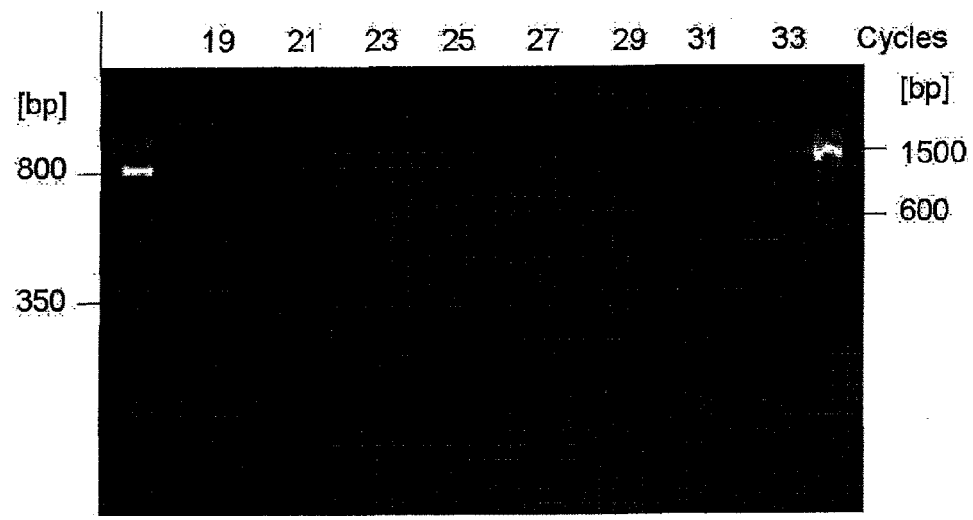
FIG. 8 shows the agarose gel analysis result of 1st PCR (moderately suppressive PCR) small scale carried out with Example 3.

500 ng of polysomal polyA− RNA were heat-denatured at 65° C. for 10 min in a final volume of 2 µl with 50 µM of strand-switching oligonucleotide (5'-TAGTCGAACT-GAAGGTCTCCAGCArGrGrG-3') (SEQ ID NO: 20) and 5 µM of random RT primer (GTACCAGCAGTAGTCGAACT-GAAGGTCTCCTCTN$_{15}$) (SEQ ID NO: 21), in 264 µM D-Threalose (Nacalai Tesque) and 1.32 M D-Sorbitol (WAKO) and then transferred quickly on ice/water mix. RT was accomplished in a volume of 10.5 µl adding the following components to reach these final concentrations: 1.19× first strand buffer (Invitrogen), 595 µM dNTPs (TaKaRa), 1.24 mM DTT (Invitrogen), 881 mM betaine (WAKO) and 200 units of SuperScriptII (Invitrogen), and incubated at 22° C. for 10 min, 50° C. for 30 min, 75° C. for 15 min in a MWG thermocycler. The tubes were then immediately transferred on ice/water mix. For the second strand synthesis a small scale moderately suppressive PCR reaction was performed to evaluate the optimal number of cycles, defined as the last cycle before the intensity of the product ceases to increase. 1 µl of first strand cDNA were amplified in a total volume of 100 µl using a mixture containing 1× ExTaq Buffer (TaKaRa), 200 µM dNTPs (TaKaRa), 100 nM forward PCR primer (5'-TAGTCGAACTGAAGGTCTCCAGC-3') (SEQ D NO: 22), 100 nM reverse PCR primer (5'-GTACCAGCAG-TAGTCGAACTGAAGGTCTCCTCT-3') (SEQ ID NO: 23), and 5 units of ExTaq (TaKaRa) with the following PCR program 5 min at 95° C., nx(15 s at 95° C., 10 s at 65° C., 2 min at 68° C.), 15 min at 68° C. and using hot start. 10 µl aliquotes were taken every two cycles and analyzed on 2% agarose gel. (FIG. 8). A large scale moderately suppressive PCR preparation using all the first-strand cDNA (9 µl) was performed in 9 reaction of 100 µl PCR products were pooled and cleaned using CTAB and GE Healthcare GFX purification columns.

Figure 9:
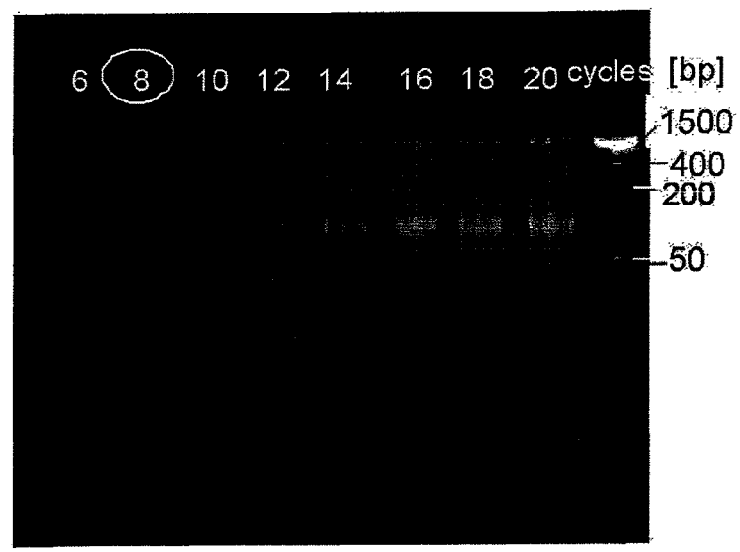
FIG. 9 shows the agarose gel analysis result of 2nd PCR small scale carried out with Example 3.

All the cDNAs were digested at 37° C. for 4 hours in a volume of 100 µl each, using 100 units of EcoP15I (NEB), 1× buffer 3 (NEB), 1 mM ATP (NEB), 1×BSA (NEB). The low molecular weight cleavage products were purified through the Microcon YM-100 membranes (Millipore) and the flow-through was concentrated on Microcon YM-10 (Millipore) according to the manufacturer's instructions. The two oligonucleotides 5'-NNGTCCTGTAGAACTCTGAACCTGT-3' (SEQ ID NO: 24) and 5'-ACAGGTTCAGAGTTCTACAGGAC-3' (SEQ ID NO: 25) were annealed in 10 µl at 1 mM each in a thermocycler heated at 95° C. and left to cool down to room temperature to form ligation adapters. 10 pmol adapters were ligated to 10 µl of the EcoP15I cleavage products using 10 µl of Mighty Ligation Mix (TaKaRa) and incubated for 16 hours at 16° C. in a thermocycler. Optimal number of cycles for the ligation product to be amplified was determined by PCR with 50 nM of forward PCR primer (5'-AATGATACGGCG ACCACCGACAGGTTCAGAGTTCTACAG-3') (SEQ ID NO: 26), 50 nM of reverse PCR primer (5'-CAAGCAGAAGACGGCATACGATAGTC-GAACTGAAGGTCTC CAG-3') (SEQ ID NO: 27), 1× ExTaq buffer (TaKaRa), 200 µM dNTPs (TaKaRa), 5 units of ExTaq (TaKaRa) and 1 µl of ligation product in a total volume of 100 µl. The program was 2 min 95° C., nx(10 s at 95° C., 10 s at 57° C.). For the large-scale amplification, 5×100 µl of PCR were performed with 1 µl of ligation product in each tube and 8 cycles (FIG. 9).

Figure 10:
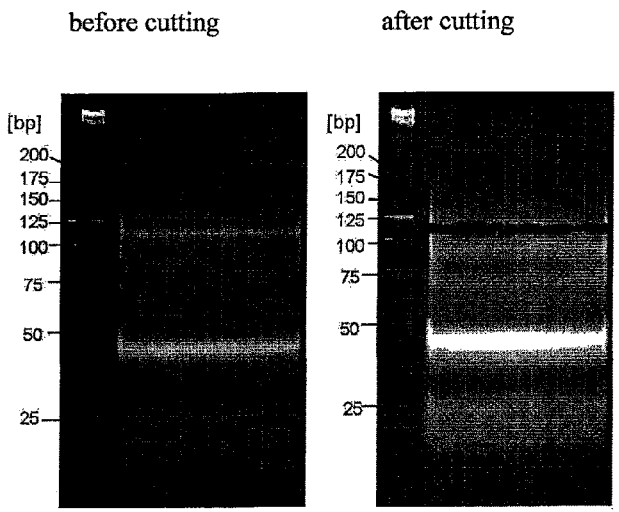
FIG. 10 shows the agarose gel analysis of the PCR products before/after cutting carried out with Example 3.
Figure 11:
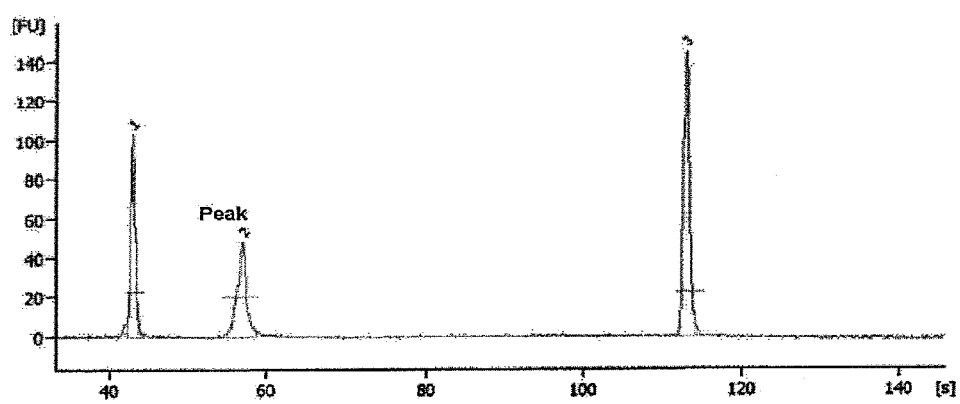
FIG. 11 shows the result of Bio Analyzer carried out with Example 3.

The excess of the primers was digested with 5 units of Exonuclease I (TaKaRa) per 100 µl PCR reaction at 37° C. for 15 min and then the enzyme was heat inactivated at 55° C. for 15 min. Then the PCR products were purified by electrophoresis on 8% polyacrylamide gel and the band corresponding to the expected size (112 base pairs) was cut and extracted by Qiaquick gel extraction kit (Qiagen)(FIG. 10). The purity and the concentration of the sample was analyzed with Agilent 2100 Bioanalyzer (FIG. 11).

The library was sequenced using a illumine-Solexa platform. 23,204,073 reads were recorded, and 17,902,698 CAGE tags were extracted. 26.31% of these tags were mapped to human ribosomal DNA and 82.42% to the human genome.

Example 4

In this experiment, nucleolus total RNA from the K562 cell line was used to create CAGE tags by random priming.

Figure 12:
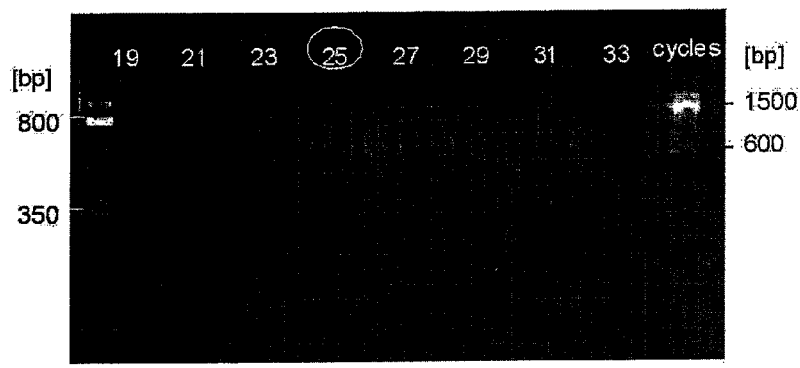
FIG. 12 shows the agarose gel analysis result of 1st PCR (moderately suppressive PCR) small scale carried out with Example 4.

500 ng of nucleolus total RNA were heat-denatured at 65° C. for 10 min in a final volume of 2 µl with 50 µM of strand-switching oligonucleotide (5'-TAGTCGAACTGAAGGTCTCCAGCArGrGrG-3') (SEQ ID NO: 28), and 5 µM of random RT primer (5'-GTACCAGCAGTAGTC-GAACTGAAGGTCTCCTCTN$_{15}$-3') (SEQ ID NO: 29) in 264 µM D-Threalose (Nacalai Tesque) and 1.32 M D-Sorbitol (WAKO) and then transferred quickly on ice/water mix. RT was accomplished in a volume of 10.5 µl adding the following components to reach these final concentrations: 1.19× first strand buffer (Invitrogen), 595 µM dNTPs (TaKaRa), 1.24 mM DTT (Invitrogen), 881 mM betaine (WAKO) and 200 units of SuperScriptII (Invitrogen), and incubated at 22° C. for 10 min, 50° C. for 30 min, 75° C. for 15 min in a MWG thermocycler. The tubes were then immediately transferred on ice/water mix. For the second strand synthesis a small scale moderately suppressive PCR reaction was performed to evaluate the optimal number of cycles, defined as the last cycle before the intensity of the product ceases to increase. 1 µl of first strand cDNA were amplified in a total volume of 100 µl using a mixture containing 1× ExTaq Buffer (TaKaRa), 200 µM dNTPs (TaKaRa), 100 nM forward PCR primer (5'-TAGTCGAACTGAAGGTCTCCAGC-3') (SEQ ID NO: 30), 100 nM reverse PCR primer (5'-GTACCAGCAG-TAGTCGAACTGAAGGTCTCCTCT-3') (SEQ ID NO: 31), and 5 units of ExTaq (TaKaRa) with the following PCR program 5 min at 95° C., nx(15 s at 95° C., 10 s at 65° C., 2 min at 68° C.), 15 min at 68° C. and using hot start. 10 µl aliquotes were taken every two cycles and analyzed on 2% agarose gel (FIG. 12). A large scale moderately suppressive PCR preparation using all the first-strand cDNA (9 µl) was performed in 9 reaction of 100 µl. PCR products were pooled and cleaned using CTAB and GE Healthcare GFX purification columns.

Figure 13:
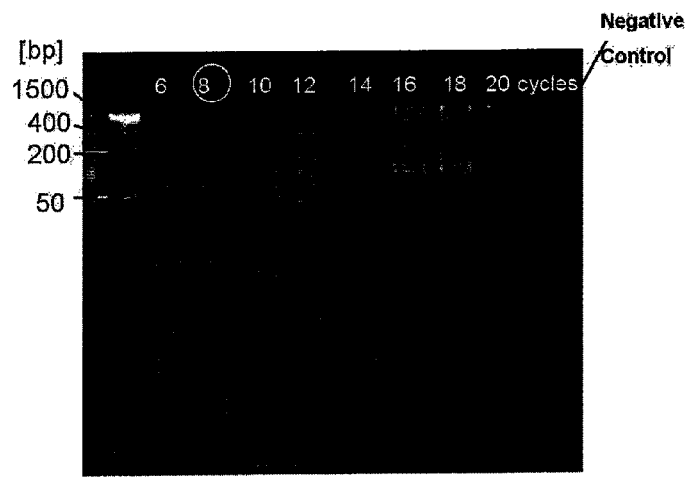
FIG. 13 shows the agarose gel analysis result of 2nd PCR small scale carried out with Example 4.

All the cDNAs were digested at 37° C. for 4 hours in a volume of 100 µl each, using 100 units of EcoP15I (NEB), 1× buffer 3 (NEB), 1 mM ATP (NEB), 1×BSA (NEB). The low molecular weight cleavage products were purified through the Microcon YM-100 membranes (Millipore) and the flow-through was concentrated on Microcon YM-10 (Millipore) according to the manufacturer's instructions. The two oligonucleotides (5'-NNGGACTGTAGAACTCTGAACCTGT-3') (SEQ ID NO: 32) and (5'-ACAGGTTCAGAGTTCTA-CAGTCC-3') (SEQ ID NO: 33 were annealed in 10 µl at 1 mM each in a thermocycler heated at 95° C. and left to cool down to room temperature to form ligation adapters. 10 pmol adapters were ligated to 10 µl of the EcoP15I cleavage products using 10 µl of Mighty Ligation Mix (TaKaRa) and incubated for 16 hours at 16° C. in a thermocycler. Optimal number of cycles for the ligation product to be amplified was determined by PCR with 50 nM of forward PCR primer (5'-AATGATACGGCGACCACCGACAGGTTCA-GAGTTCTACAG-3') (SEQ ID NO: 34), 50 nM of reverse PCR primer (5'-CAAGCAGAAGACGGCATACGATAGTC GAACTGAAGGTCTCCAG-3') (SEQ ID NO: 35), 1× ExTaq buffer (TaKaRa), 200 µM dNTPs (TaKaRa), 5 units of ExTaq (TaKaRa) and 1 µl of ligation product in a total volume of 100 The program was 2 min 95° C., nx(10 s at 95° C., 10 s at 57° C.). For the large-scale amplification, 5×100 µl of PCR were performed with 1 µl of ligation product in each tube and 8 cycles (FIG. 13).

Figure 14:
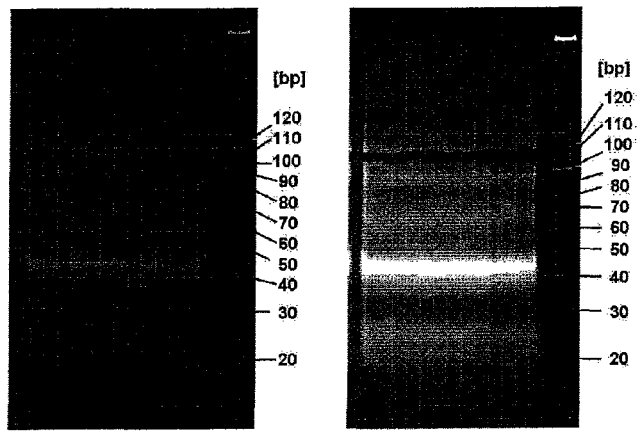
FIG. 14 shows the agarose gel analysis of the PCR products before/after cutting carried out with Example 4.
Figure 15:
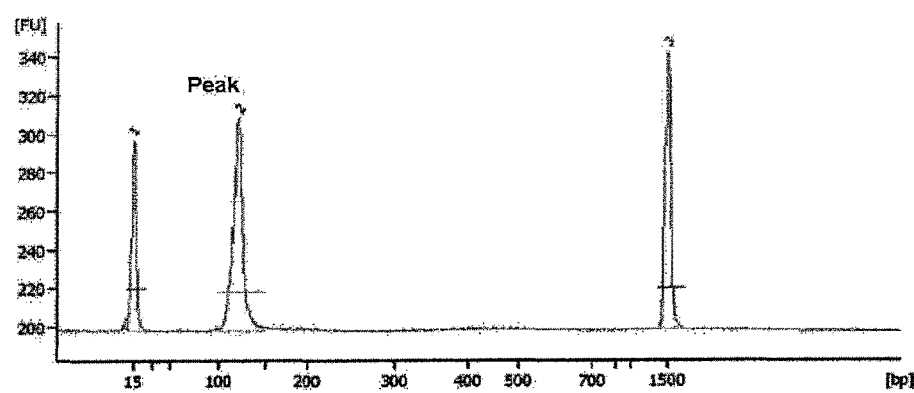
FIG. 15 shows the result of Bio Analyzer carried out with Example 4.

The excess of the primers was digested with 5 units of Exonuclease I (TaKaRa) per 100 µl PCR reaction at 37° C. for 15 min and then the enzyme was heat inactivated at 55° C. for 15 min. Then the PCR products were purified by electrophoresis on 8% polyacrylamide gel and the band corresponding to the expected size (112 base pairs) was cut and extracted by Qiaquick gel extraction kit (Qiagen)(FIG. 14). The purity and the concentration of the sample was analyzed with Agilent 2100 Bioanalyzer (FIG. 15).

The library was sequenced using a illumine-Solexa platform. 27,839,343 reads were recorded, and 21,856,936 CAGE tags were extracted. 26.01% of these tags were mapped to human ribosomal DNA and 76.58% to the human genome.

Example 5

In this experiment, nuclear plasma total RNA from the K562 cell line was used to create CAGE tags by random priming.

Figure 16:
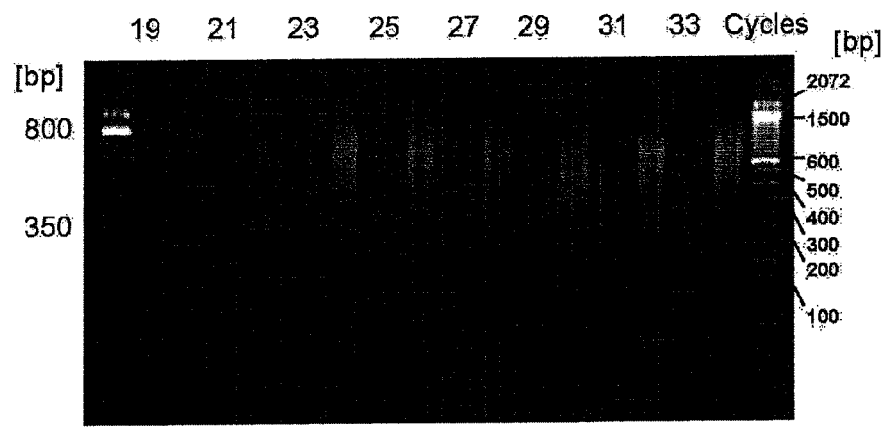
FIG. 16 shows the agarose gel analysis result of 1st PCR (moderately suppressive PCR) small scale carried out with Example 5.

500 ng of nuclear plasma total RNA were heat-denatured at 65° C. for 10 min in a final volume of 2 µl with 50 µM of strand-switching oligonucleotide (5'-TAGTCGAACT-GAAGGTCTCCAGCArGrGrG-3') (SEQ ID NO: 36) and 5 µM of random RT primer (5'-GTACCAGCAGTAGTC-GAACTGAAGGTCTCCTCTN$_{15}$-3') (SEQ ID NO: 37) in 264 µM D-Threalose (Nacalai Tesque) and 1.32 M D-Sorbitol (WAKO) and then transferred quickly on ice/water mix. RT was accomplished in a volume of 10.5 µl adding the following components to reach these final concentrations: 1.19× first strand buffer (Invitrogen), 595 µM dNTPs (TaKaRa), 1.24 mM DTT (Invitrogen), 881 mM betaine (WAKO) and 200 units of SuperScriptII (Invitrogen), and incubated at 22° C. for 10 min, 50° C. for 30 min, 75° C. for 15 min in a MWG thermocycler. The tubes were then immediately transferred on ice/water mix. For the second strand synthesis a small scale moderately suppressive PCR reaction was performed to evaluate the optimal number of cycles, defined as the last cycle before the intensity of the product ceases to increase. 1 µl of first strand cDNA were amplified in a total volume of 100 µl using a mixture containing 1× ExTaq Buffer (TaKaRa), 200 µM dNTPs (TaKaRa), 100 nM forward PCR primer (5'-TAGTCGAACTGAAGGTCTCCAGC-3') (SEQ ID NO: 38), 100 nM reverse PCR primer (5'-GTACCAGCAG-TAGTCGAACTGAAGGTCTCCTCT-3') (SEQ ID NO: 39), and 5 units of ExTaq (TaKaRa) with the following PCR program 5 min at 95° C., n×(15 s at 95° C., 10 s at 65° C., 2 min at 68° C.), 15 min at 68° C. and using hot start. 10 µl aliquotes were taken every two cycles and analyzed on 2% agarose gel (FIG. 16). A large scale moderately suppressive PCR preparation using all the first-strand cDNA (9 µl) was performed in 9 reaction of 100 PCR products were pooled and cleaned using CTAB and GE Healthcare GFX purification columns.

Figure 17:
FIG. 17 shows the agarose gel analysis result of 2nd PCR small scale carried out with Example 5.

All the cDNAs were digested at 37° C. for 4 hours in a volume of 100 µl each, using 100 units of EcoP15I (NEB), 1× buffer 3 (NEB), 1 mM ATP (NEB), 1×BSA (NEB). The low molecular weight cleavage products were purified through the Microcon YM-100 membranes (Millipore) and the flow-through was concentrated on Microcon YM-10 (Millipore) according to the manufacturer's instructions. The two oligonucleotides (5'-NNGAGCTGTAGAACTCTGAACCTGT-3') (SEQ ID NO: 40) and (5'-ACAGGTTCAGAGTTCTA-CAGCTC-3') (SEQ ID NO: 41) were annealed in 10 µl at 1 mM each in a thermocycler heated at 95° C. and left to cool down to room temperature to form ligation adapters. 10 pmol adapters were ligated to 10 µl of the EcoP15I cleavage products using 10 µl of Mighty Ligation Mix (TaKaRa) and incubated for 16 hours at 16° C. in a thermocycler. Optimal number of cycles for the ligation product to be amplified was determined by PCR with 50 nM of forward PCR primer (5'-AATGATACGGCGACCACCGACAGGTTCA-GAGTTCTACAG-3') (SEQ ID NO: 42), 50 nM of reverse PCR primer (5'-CAAGCAGAAGACGGCATACGATAGTC-GAACT GAAGGTCTCCAG-3'(SEQ ID NO: 43)), 1× ExTaq buffer (TaKaRa), 200 µM dNTPs (TaKaRa), 5 units of ExTaq (TaKaRa) and 1 µl of ligation product in a total volume of 100 µl. The program was 2 min 95° C., n×(10 s at 95° C., 10 s at 57° C.). For the large-scale amplification, 5×100 µl of PCR were performed with 1 µl of ligation product in each tube and 8 cycles (FIG. 17).

Figure 18:
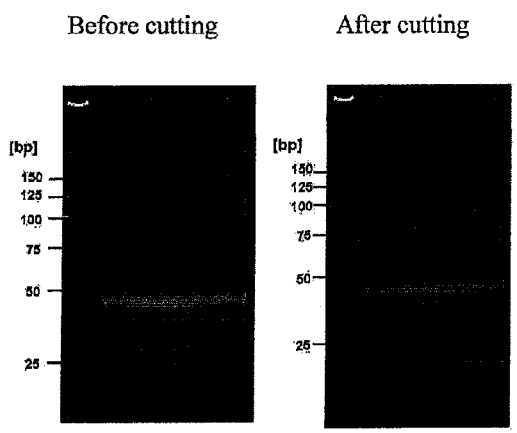
FIG. 18 shows the agarose gel analysis of the PCR products before/after cutting carried out with Example 5.
Figure 19:
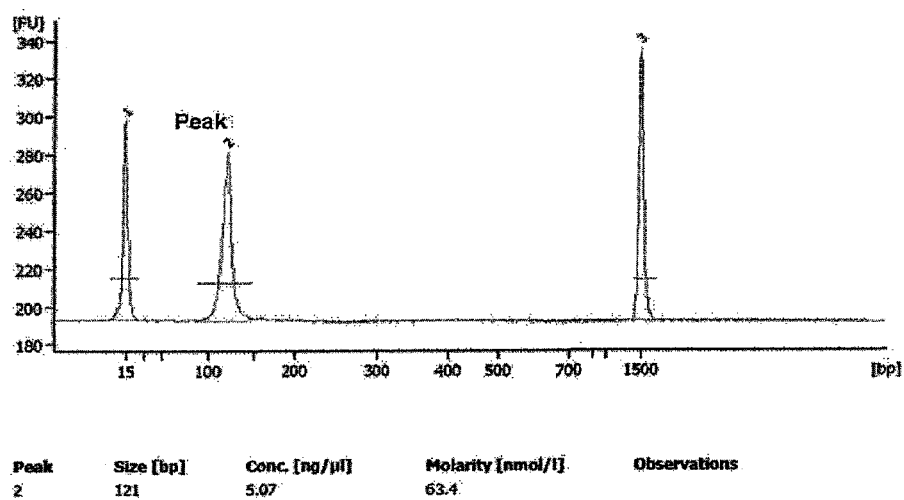
FIG. 19 shows the result of Bio Analyzer carried out with Example 5.

The excess of the primers was digested with 5 units of Exonuclease I (TaKaRa) per 100 µl PCR reaction at 37° C. for 15 min and then the enzyme was heat inactivated at 55° C. for 15 min. Then the PCR products were purified by electrophoresis on 8% polyacrylamide gel and the band corresponding to the expected size (112 base pairs) was cut and extracted by Qiaquick gel extraction kit (Qiagen)(FIG. 18). The purity and the concentration of the sample was analyzed with Agilent 2100 Bioanalyzer (FIG. 19).

The library was sequenced using a illumine-Solexa platform. 25,305,506 reads were recorded, and 20,328,111 CAGE tags were extracted. 10.95% of these tags were mapped to human ribosomal DNA and 86.30% to the human genome.

Example 6

In this experiment, chromatin total RNA from the K562 cell line was used to create CAGE tags by random priming.

Figure 20:
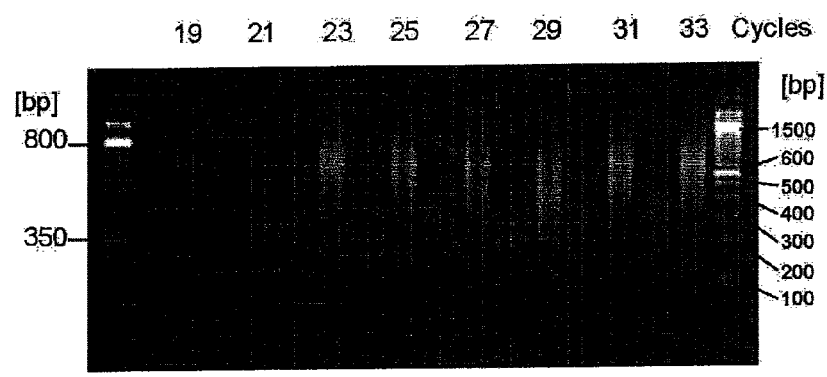
FIG. 20 shows the agarose gel analysis result of 1st PCR (moderately suppressive PCR) small scale carried out with Example 6.

500 ng of chromatin total RNA were heat-denatured at 65° C. for 10 min in a final volume of 2 µl with 50 µM of strand-switching oligonucleotide (5'-TAGTCGAACT-GAAGGTCTCCAGCArGrGrG-3') (SEQ ID NO: 44) and 5 µM of random RT primer (5'-GTACCAGCAGTAGTC-GAACTGAAGGTCTCCTCTN$_{15}$-3') (SEQ ID NO: 45) in 264 µM D-Threalose (Nacalai Tesque) and 1.32 M D-Sorbitol (WAKO) and then transferred quickly on ice/water mix. RT was accomplished in a volume of 10.5 µl adding the following components to reach these final concentrations: 1.19× first strand buffer (Invitrogen), 595 µM dNTPs (TaKaRa), 1.24 mM DTT (Invitrogen), 881 mM betaine (WAKO) and 200 units of SuperScriptII (Invitrogen), and incubated at 22° C. for 10 min, 50° C. for 30 min, 75° C. for 15 min in a MWG thermocycler. The tubes were then immediately transferred on ice/water mix. For the second strand synthesis a small scale moderately suppressive PCR reaction was performed to evaluate the optimal number of cycles, defined as the last cycle before the intensity of the product ceases to increase. 1 µl of first strand cDNA were amplified in a total volume of 100 µl using a mixture containing 1× ExTaq Buffer (TaKaRa), 200 µM dNTPs (TaKaRa), 100 nM forward PCR primer (5'-TAGTCGAACTGAAGGTCTCCAGC-3') (SEQ ID NO: 46), 100 nM reverse PCR primer (5'-GTACCAGCAG-TAGTCGAACTGAAGGTCTCCTCT-3') (SEQ ID NO: 47), and 5 units of ExTaq (TaKaRa) with the following PCR program 5 min at 95° C., n×(15 s at 95° C., 10 s at 65° C., 2 min at 68° C.), 15 min at 68° C. and using hot start. 10 µl aliquotes were taken every two cycles and analyzed on 2% agarose gel (FIG. 20). A large scale moderately suppressive PCR preparation using all the first-strand cDNA (9 µl) was performed in 9 reaction of 100 µl. PCR products were pooled and cleaned using CTAB and GE Healthcare GFX purification columns.

Figure 21:
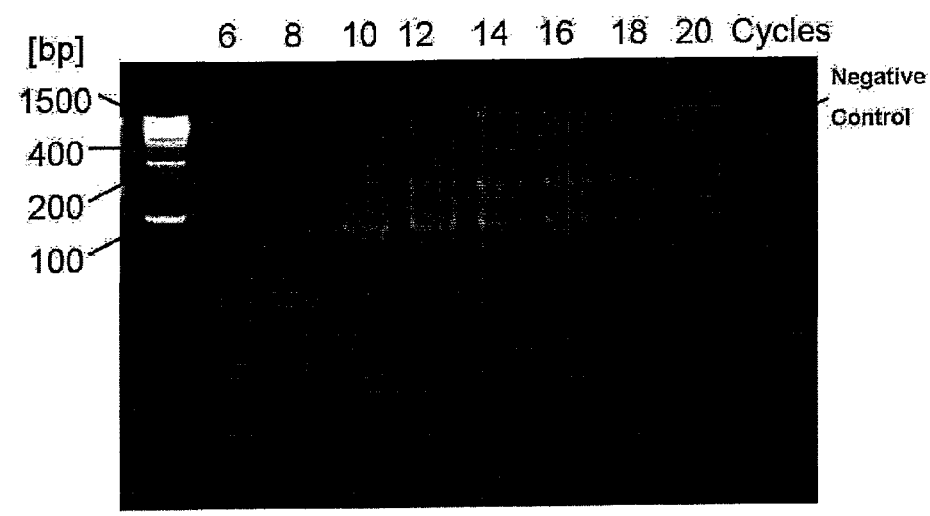
FIG. 21 shows the agarose gel analysis result of 2nd PCR small scale carried out with Example 6.

All the cDNAs were digested at 37° C. for 4 hours in a volume of 100 µl each, using 100 units of EcoP15I (NEB), 1× buffer 3 (NEB), 1 mM ATP (NEB), 1×BSA (NEB). The low molecular weight cleavage products were purified through the Microcon YM-100 membranes (Millipore) and the flow-through was concentrated on Microcon YM-10 (Millipore) according to the manufacturer's instructions. The two oligonucleotides (5'-NNGCTCTGTAGAACTCTGAACCTGT-3') (SEQ ID NO: 48) and (5'-ACAGGTTCAGAGTTCTA-CAGAGC-3') (SEQ ID NO: 49) were annealed in 10 µl at 1 mM each in a thermocycler heated at 95° C. and left to cool down to room temperature to form ligation adapters. 10 pmol adapters were ligated to 10 µl of the EcoP15I cleavage products using 10 µl of Mighty Ligation Mix (TaKaRa) and incubated for 16 hours at 16° C. in a thermocycler Optimal number of cycles for the ligation product to be amplified was determined by PCR with 50 nM of forward PCR primer (5'-AATGATACGGCGACCACCGACAGGTTCA-GAGTTCTACAG-3') (SEQ ID NO: 50), 50 nM of reverse PCR primer (5'-CAAGCAGAAGACGGCATACGATAGTC GAACTGAAGGTCTCCAG-3') (SEQ ID NO: 51), 1× ExTaq buffer (TaKaRa), 200 µM dNTPs (TaKaRa), 5 units of ExTaq (TaKaRa) and 1 µl of ligation product in a total volume of 100 µl. The program was 2 min 95° C., n×(10 s at 95° C., 10 s at 57° C.). For the large-scale amplification, 5×100 µl of PCR were performed with 1 µl of ligation product in each tube and 8 cycles (FIG. 21).

Figure 22:
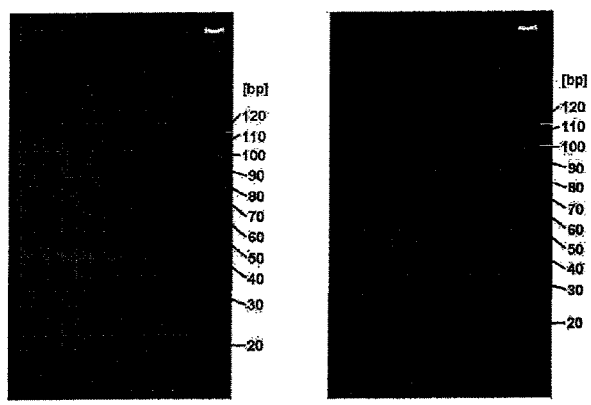
FIG. 22 shows the agarose gel analysis of the PCR products before/after cutting carried out with Example 6.
Figure 23:
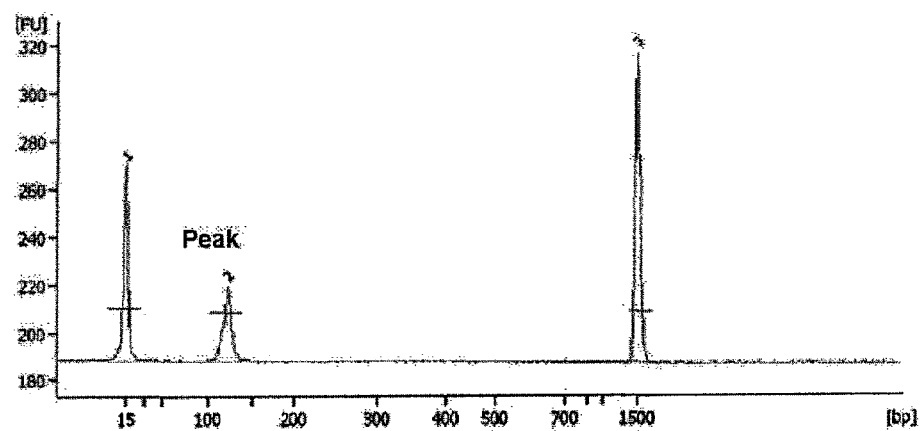
FIG. 23 shows the result of Bio Analyzer carried out with Example 6.

The excess of the primers was digested with 5 units of Exonuclease I (TaKaRa) per 100 µl PCR reaction at 37° C. for 15 min and then the enzyme was heat inactivated at 55° C. for 15 min. Then the PCR products were purified by electrophoresis on 8% polyacrylamide gel and the band corresponding to the expected size (112 base pairs) was cut and extracted by Qiaquick gel extraction kit (Qiagen)(FIG. 22). The purity and the concentration of the sample was analyzed with Agilent 2100 Bioanalyzer (FIG. 23).

The library was sequenced using a illumine-Solexa platform. 21,253,077 reads were recorded, and 16,137,405 CAGE tags were extracted. 5.28% of these tags were mapped to human ribosomal DNA and 86.71% to the human genome.

Example 7

In this experiment, total RNA were prepared from microdissected brain tissues from the rat neonate to create CAGE tags by random priming. The stages of rat neonate are 3, 5, 7, 9, 12, 18, 28 days. The microdissected samples were containing between 10 and 20 ng of RNA. We also used commercial total RNA for control (whole embryo and whole adult brain).

Figure 24:
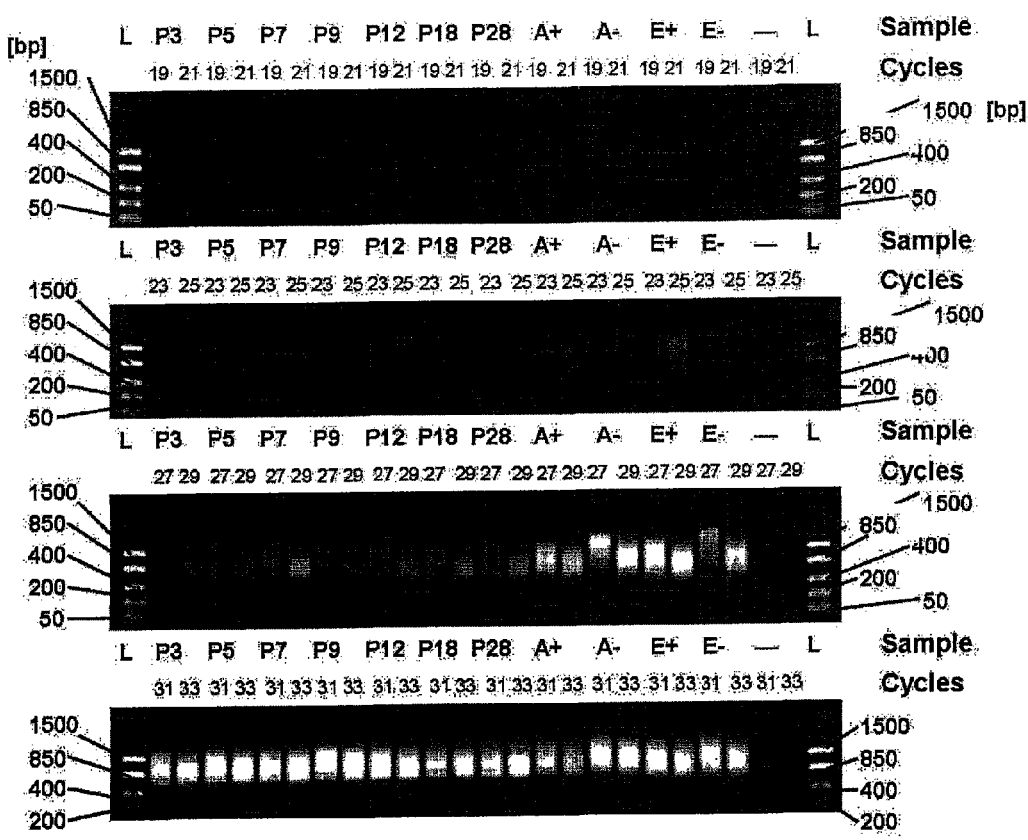
FIG. 24 shows the agarose gel analysis result of 1st PCR (moderately suppressive PCR) small scale carried out with Example 7. A—: no strand-switching oligonucleotide, E—: no strand-switching oligonucleotide, —: no template
Figure 25:
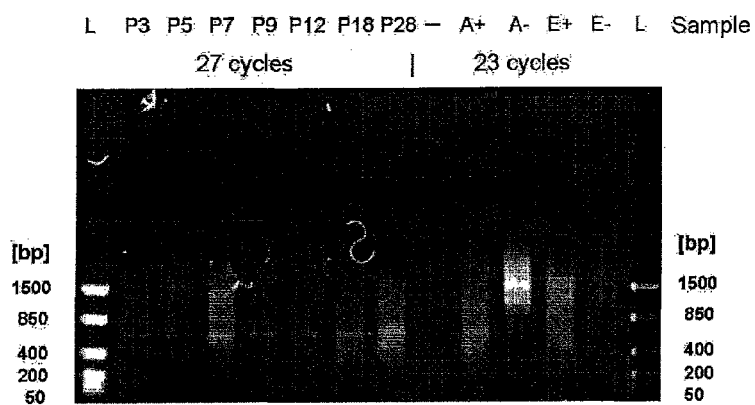
FIG. 25 shows the agarose gel analysis result of 1st round of 1st PCR (moderately suppressive PCR) large scale carried out with Example 7. A—: no strand-switching oligonucleotide, E—: no strand-switching oligonucleotide, —: no template
Figure 26:
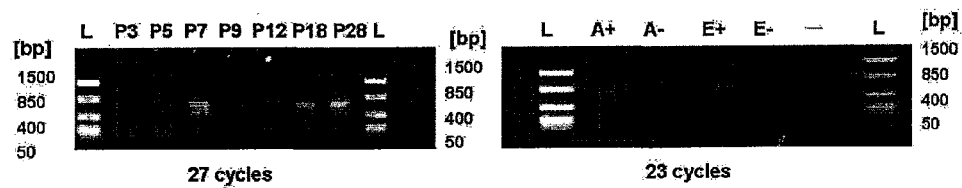
FIG. 26 shows the agarose gel analysis result of 2nd round of 1st PCR (moderately suppressive PCR) large scale carried out with Example 7.

Between 10 and 20 ng of total RNA were heat-denatured at 65° C. for 10 min in a final volume of 2 µl with 50 µM of strand-switching oligonucleotide (TAGTCGAACTGAAGGTCTCCAGCArGrGrG) (SEQ ID NO: 52) and 5 µM of random RT primer (GTACCAGCAGTAGTCGAACTGAAGGTCTCCTCTN$_{15}$) (SEQ ID NO: 53), in 264 µM D-Threalose (Nacalai Tesque) and 1.32 M D-Sorbitol (WAKO) and then transferred quickly on ice/water mix. RT was accomplished in a volume of 10.5 µl adding the following components to reach these final concentrations: 1.19× first strand buffer (Invitrogen), 595 µM dNTPs (TaKaRa), 1.24 mM DTT (Invitrogen), 881 mM betaine (WAKO) and 200 units of SuperScriptII (Invitrogen), and incubated at 22° C. for 10 min, 50° C. for 30 min, 75° C. for 15 min in a MWG thermocycler. The tubes were then immediately transferred on ice/water mix. For the second strand synthesis a small scale moderately suppressive PCR reaction was performed to evaluate the optimal number of cycles, defined as the last cycle before the intensity of the product ceases to increase. 1.5 µl of first strand cDNA were amplified in a total volume of 100 nl using a mixture containing 1× ExTaq Buffer (TaKaRa), 200 µM dNTPs (TaKaRa), 100 nM forward PCR primer (TAGTCGAACTGAAGGTCTCCAGC) (SEQ ID NO: 54), 100 nM reverse PCR primer primer (GTACCAGCAGTAGTCGAACTGAAGGTCTCCTCT) SEQ ID NO; 55), and 5 units of ExTaq (TaKaRa) with the following PCR program 5 min at 95° C., n×(15 s at 95° C., 10 s at 65° C., 2 min at 68° C.), 15 min at 68° C. and using hot start. 5 µl aliquotes were taken every two cycles and analyzed on 2% agarose gel (FIG. 24). A large scale moderately suppressive PCR preparation, which was divided in two rounds, using the first-strand cDNA was performed in two rounds of 2 reactions of 100 µl (FIG. 25, 26). PCR products were purified on QIAquick (Qiagen).

All the cDNAs were digested at 37° C. for 4 hours in a volume of 100 µl each, using 100 units of EcoP15I (NEB), 1× buffer 3 (NEB), 1 mM ATP (NEB), 1×BSA (NEB). The low molecular weight cleavage products were purified through the Microcon YM-100 membranes (Millipore) and the flow-through was concentrated on Microcon YM-10 (Millipore) according to the manufacturer's instructions. The nine pairs of oligonucleotides, which were
5'-NNAAACTGTAGAACTCTGAACCTGT-3' (SEQ ID NO: 56) and
5'-ACAGGTTCAGAGTTCTACAGTTT-3'(SEQ ID NO: 57),
5'-NNACCCTGTAGAACTCTGAACCTGT-3'(SEQ ID NO: 58) and
5'-ACAGGTTCAGAGTTCTACAGGGT-3'(SEQ ID NO: 59),
5'-NNAGGCTGTAGAACTCTGAACCTGT-3' (SEQ ID NO: 60) and
5'-ACAGGTTCAGAGTTCTACAGCCT-3'(SEQ ID NO: 61),
5'-NNATTCTGTAGAACTCTGAACCTGT-3'(SEQ ID NO: 62) and
5'-ACAGGTTCAGAGTTCTACAGAAT-3'(SEQ ID NO: 63),
5'-NNCTACTGTAGAACTCTGAACCTGT-3' (SEQ ID NO: 64) and
5'-ACAGGTTCAGAGTTCTACAGTAG-3'(SEQ ID NO: 65),
5'-NNCACCTGTAGAACTCTGAACCTGT-3' (SEQ ID NO: 66) and
5'-ACAGGTTCAGAGTTCTACAGGTG-3'(SEQ ID NO: 67),
5'-NNCCGCTGTAGAACTCTGAACCTGT-3' (SEQ ID NO: 68) and
5'-ACAGGTTCAGAGTTCTACAGCGG-3'(SEQ ID NO: 69),
5'-NNCGTCTGTAGAACTCTGAACCTGT-3' (SEQ ID NO: 70) and
5'-ACAGGTTCAGAGTTCTACAGACG-3', (SEQ ID NO: 71) and
5'-NNGAGCTGTAGAACTCTGAACCTGT-3' (SEQ ID NO: 72) and
5'-ACAGGTTCAGAGTTCTACAGCTC-3'(SEQ ID NO: 73), were annealed in 10 µl at 1 mM each in a thermocycler heated at 95° C. and left to cool down to room temperature to form ligation adapters. 10 pmol adapters were ligated to 10 µl of the EcoP15I cleavage products using 10 µl of Mighty Ligation Mix (TaKaRa) and incubated for 16 hours at 16° C. in a thermocycler. Optimal number of cycles for the ligation product to be amplified was determined by PCR with 50 nM of forward PCR primer (AATGATACGGCGACCACCGACAGGTTCAGAGTTCTACAG) (SEQ ID NO: 74), 50 nM of reverse PCR primer (CAAGCAGAAGACGGCATACGATAGTCGAACTGAA GGTCTCCAG) (SEQ ID NO: 75), 1× ExTaq buffer (TaKaRa), 200 µM dNTPs (TaKaRa), 5 units of ExTaq (TaKaRa) and 2 µl of ligation product in a total volume of 100 µl. The program was 2 min 95° C., n×(10 s at 95° C., 10 s at 57° C.). For the large-scale amplification, 2~4×100 µl of PCR were performed with 2 µl of ligation product in each tube and 13 cycles.

The excess of the primers was digested with 5 units of Exonuclease I (TaKaRa) per 100 µl PCR reaction at 37° C. for 15 min and then the enzyme was heat inactivated at 55° C. for 15 min. Then the PCR products were purified by electrophoresis on 8% polyacrylamide gel and the band corresponding to the expected size (112 base pairs) was cut and extracted by Qiaquick gel extraction kit (Qiagen)(FIG. 27). The purity of the sample was analyzed with electrophoresis (FIG. 28). The library was sequenced using a illumina-Solexa platform.

Example 8

In this experiment, as well as above, total RNA were prepared from microdissected brain tissues from the rat neonate to create CAGE tags by random priming. The stages of rat neonate are 3, 5, 7, 9, 12, 18, 28 days. The microdissected samples were containing between 10 and 20 ng of RNA. We also used commercial total RNA for control (whole embryo and whole adult brain).

Figure 29:
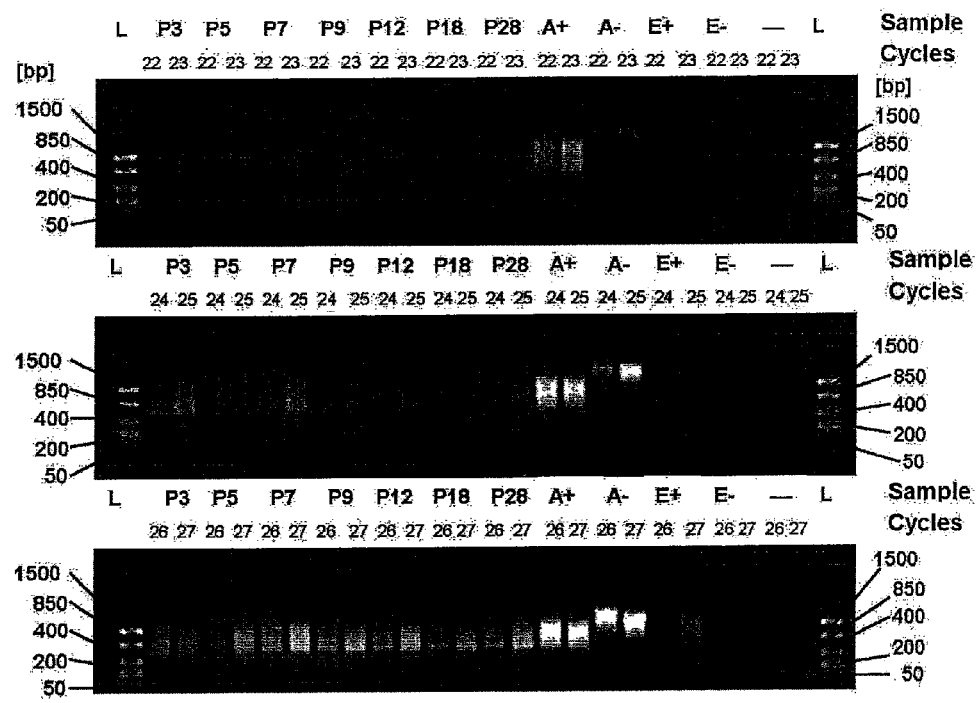
FIG. 29 shows the agarose gel analysis result of 1st PCR (moderately suppressive PCR) small scale carried out with Example 8. A—: no strand-switching oligonucleotide, E—: no strand-switching oligonucleotide, —: no template
Figure 30:
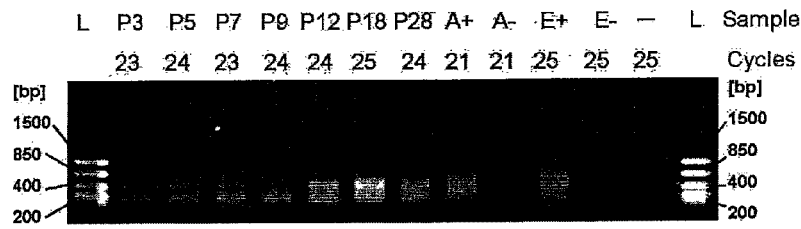
FIG. 30 shows the agarose gel analysis result of 1st round of 1st PCR (moderately suppressive PCR) large scale carried out with Example 8. A—: no strand-switching oligonucleotide, E—: no strand-switching oligonucleotide, —: no template

Between 10 and 20 ng of total RNA were heat-denatured at 65° C. for 10 min in a final volume of 2 µl with 50 µM of strand-switching oligonucleotide (TAGTCGAACTGAAG-GTCTCCAGCArGrGrG)(SEQ ID NO: 76) and 5 µM of random RT primer (GTACCAGCAGTAGTCGAACTGAAG-GTCTCCTCTN$_{15}$) (SEQ ID NO: 77), in 264 µM D-Threalose (Nacalai Tesque) and 1.32 M D-Sorbitol (WAKO) and then transferred quickly on ice/water mix. RT was accomplished in a volume of 10.5 µl adding the following components to reach these final concentrations: 1.19× first strand buffer (Invitrogen), 595 µM dNTPs (TaKaRa), 1.24 mM DTT (Invitrogen), 881 mM betaine (WAKO) and 200 units of SuperScriptII (Invitrogen), and incubated at 22° C. for 10 min, 50° C. for 30 min, 75° C. for 15 min in a MWG thermocycler. The tubes were then immediately transferred on ice/water mix. For the second strand synthesis a small scale moderately suppressive PCR reaction was performed to evaluate the optimal number of cycles, defined as the last cycle before the intensity of the product ceases to increase. 1.5 of first strand cDNA were amplified in a total volume of 100 µl using a mixture containing 1× ExTaq Buffer (TaKaRa), 200 µM dNTPs (TaKaRa), 100 nM forward PCR primer (TAGTCGAACTGAAGGTCTCCAGC) (SEQ ID No: 78), 100 nM reverse PCR primer primer (GTACCAGCAG-TAGTCGAACTGAAGGTCTCCTCT) (SEQ ID NO: 79), and 5 units of ExTaq (TaKaRa) with the following PCR program 5 min at 95° C., n×(15 s at 95° C., 10 s at 65° C., 2 min at 68° C.), 15 min at 68° C. and using hot start. 5 µl aliquotes were taken every two cycles and analyzed on 2% agarose gel (FIG. 29). A large scale moderately suppressive PCR preparation, which was divided in two rounds, using the first-strand cDNA was performed in two rounds of 2 reactions of 100 µl (FIG. 30, 31). PCR products were purified on QIAquick (Qiagen).

All the cDNAs were digested at 37° C. for 4 hours in a volume of 100 µl each, using 100 units of EcoP15I (NEB), 1× buffer 3 (NEB), 1 mM ATP (NEB), 1×BSA (NEB). The low molecular weight cleavage products were purified through the Microcon YM-100 membranes (Millipore) and the flow-through was concentrated on Microcon YM-10 (Millipore) according to the manufacturer's instructions. The nine pairs of oligonucleotides, which were
5'-NNAAACTGTAGAACTCTGAACCTGT-3' (SEQ ID NO: 80) and
5'-ACAGGTTCAGAGTTCTACAGTTT-3'(SEQ ID NO: 81),
5'-NNACCCTGTAGAACTCTGAACCTGT-3'(SEQ ID NO: 82) and
5'-ACAGGTTCAGAGTTCTACAGGGT-3'(SEQ ID NO: 83),
5'-NNAGGCTGTAGAACTCTGAACCTGT-3' (SEQ ID NO: 84) and
5'-ACAGGTTCAGAGTTCTACAGCCT-3'(SEQ ID NO: 85),
5'-NNATTCTGTAGAACTCTGAACCTGT-3' (SEQ ID NO: 86) and
5'-ACAGGTTCAGAGTTCTACAGAAT-3'(SEQ ID NO: 87),
5'-NNCGTCTGTAGAACTCTGAACCTGT-3' (SEQ ID NO: 88) and
5'-ACAGGTTCAGAGTTCTACAGACG-3' (SEQ ID NO: 89),
5'-NNGGACTGTAGAACTCTGAACCTGT-3'(SEQ ID NO: 90) and
5'-ACAGGTTCAGAGTTCTACAGTCC-3' (SEQ ID NO: 91),
5'-NNGTCCTGTAGAACTCTGAACCTGT-3' (SEQ ID NO: 92) and
5'-ACAGGTTCAGAGTTCTACAGGAC-3' (SEQ ID NO: 93),
5'-NNGAGCTGTAGAACTCTGAACCTGT-3' (SEQ ID NO: 94) and
5'-ACAGGTTCAGAGTTCTACAGCTC-3' (SEQ ID NO: 95), and
5'-NNGCTCTGTAGAACTCTGAACCTGT-3' (SEQ ID NO: 96) and
5'-ACAGGTTCAGAGTTCTACAGAGC-3, (SEQ ID NO: 97) were annealed in 10 µl at 1 mM each in a thermocycler heated at 95° C. and left to cool down to room temperature to form ligation adapters. 10 pmol adapters were ligated to 10 µl of the EcoP15I cleavage products using 10 µl of Mighty Ligation Mix (TaKaRa) and incubated for 16 hours at 16° C. in a thermocycler. Optimal number of cycles for the ligation product to be amplified was determined by PCR with 50 nM of forward PCR primer (AATGATACGGCGACCACCGA-CAGGTTCAGAGTTCTACAG) (SEQ ID NO: 98), 50 nM of reverse PCR primer (CAAGCAGAAGACGGCATACGAT-AGTCGAACTGAA GGTCTCCAG) (SEQ ID NO: 99), 1× ExTaq buffer (TaKaRa), 200 µM dNTPs (TaKaRa), 5 units of ExTaq (TaKaRa) and 2 µl of ligation product in a total volume of 100 µl. The program was 2 min 95° C., n×(10 s at 95° C., 10 s at 57° C.). For the large-scale amplification, 2-4×100 µl of PCR were performed with 2 µl of ligation product in each tube and 13 cycles.

The excess of the primers was digested with 5 units of Exonuclease I (TaKaRa) per 100 µl PCR reaction at 37° C. for 15 min and then the enzyme was heat inactivated at 55° C. for 15 min. Then the PCR products were purified by electrophoresis on 8% polyacrylamide gel and the band corresponding to the expected size (112 base pairs) was cut and extracted by Qiaquick gel extraction kit (Qiagen)(FIG. 32, 33). The purity of the sample was analyzed with electrophoresis (FIG. 28). The library was sequenced using a illumina-Solexa platform.

Example 9

In this experiment, total RNA from the C2C12 MBc WT cell line was used to create CAGE tags by random priming.

1 µg of total RNA were heat-denatured at 65° C. for 10 min in a final volume of 2 µl with 5 µM of random RT primer (5'-GTACCAGCAGTAGTCGAACTGAAGG TCTC-CTCTN$_{15}$-3') (SEQ ID NO: 100), in 264 µM D-Threalose (Nacalai Tesque) and 1.32 M D-Sorbitol (WAKO) and then transferred quickly on ice/water mix. RT was accomplished in a volume of 10.5 µl adding the following components to reach these final concentrations: 1.19× first strand buffer (Invitrogen), 595 µM dNTPs (TaKaRa), 1.24 mM DTT (Invitrogen), 881 mM betaine (WAKO) and 200 units of SuperScriptII (Invitrogen), and incubated at 22° C. for 10 min, 50° C. for 30 min, 75° C. for 15 min in a MWG thermocycler. The tubes were then immediately transferred on ice/water mix. For the second strand synthesis a small scale moderately suppressive PCR reaction was performed to evaluate the optimal number of cycles, defined as the last cycle before the intensity of the product ceases to increase. 2.0 µl of first strand cDNA were amplified in a total volume of 100 µl using a mixture containing 1× ExTaq Buffer (TaKaRa), 200 µM dNTPs (TaKaRa), 100 nM L1-6 forward PCR primer (5'-

TAGTCGAACTGAAGGTCTCCAGCACAA-GAAGCCTACAGGACT-3') (SEQ ID NO: 101) or L1-13 forward PCR primer (5'-TAGTCGAACTGAAGGTCTC-CAG CGCCTACAGGACTCCAAATA-3') (SEQ ID NO: 102), 100 nM reverse PCR primer (GTACCAGCAGTAGTC-GAACTGAAGGTCTCCTCT) (SEQ ID NO: 103), and 5 units of ExTaq (TaKaRa) with the following PCR program 5 min at 95° C., n×(15 s at 95° C., 10 s at 65° C., 2 min at 68° C.), 15 min at 68° C. and using hot start. 5 µl aliquotes were taken every two cycles and analyzed on 1.5% agarose gel (FIG. 34). A large scale moderately suppressive PCR preparation using the first-strand cDNA was performed in 5 reactions of 100 µl. PCR products were purified on QIAquick (Qiagen).

Figure 35:
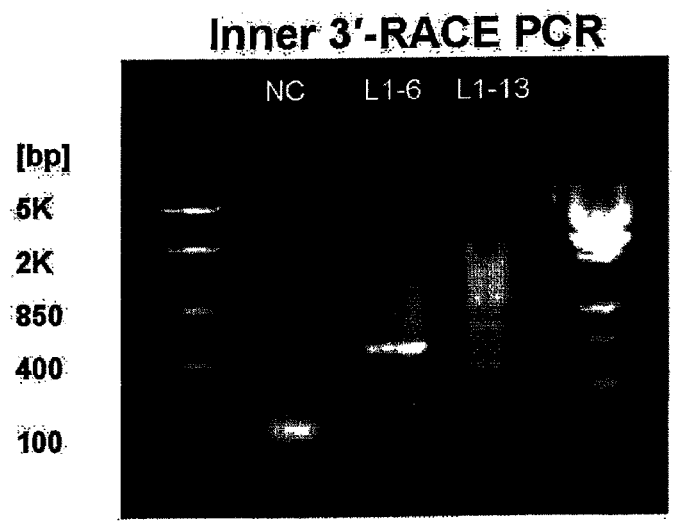
FIG. 35 shows the purity of PCR products carried out with Example 9. 1.5% Agarose gel: 100V, 12 min, NC: Negative control (no template)

Inner 3' RACE PCR was performed with a part of sequencing adapters. 2.0 µl of PCR products were amplified in a total volume of 100 µl using a mixture containing 1× ExTaq Buffer (TaKaRa), 200 µM dNTPs (TaKaRa), 100 nM L1-6 454-A up forward PCR primer (5'-CATCTGTTCCCTCCCTGTCT-CAGACAAGAAGCCTACAGGACT-3') (SEQ ID NO: 104 or L1-13 454-A up forward PCR primer (5'-CATCTGTT CCCTCCCTGTCTCAGGCCTACAGGACTCCAAATA-3') (SEQ ID NO: 105, 100 nM reverse 454-B up PCR primer (5'-CTATCCCCTGTTGCGTGTCTCAGTAGTCG AACT-GAAGGTCTCCTCT-3') (SEQ ID NO: 106, and 5 units of ExTaq (TaKaRa) with the following PCR program 5 min at 94° C., 35 cycles×(30 s at 94° C., 30 s at 60° C., 2 min at 72° C.), 15 min at 72° C. and using hot start. PCR products were purified by QIAGEN MinElute column (Qiagen) and analyzed on 1.5 agarose gel (FIG. 35).

Figure 36:
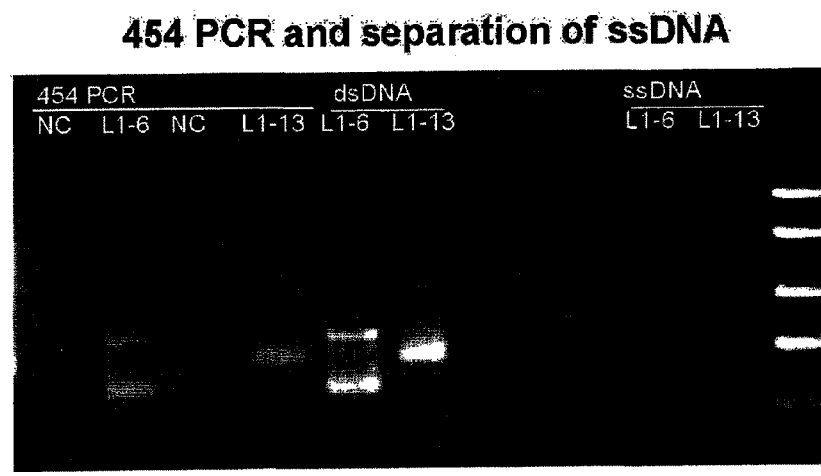
FIG. 36 shows the results of 454 PCR and separation of ssDNA carried out with Example 9. 1.5% Agarose gel: 100V, 20 min, NC: Negative control (no template)

For synthesizing the biotinylated PCR products with biotinylated primers, 20 ng (2.0 µl) of inner PCR products were amplified in a total volume of 100 µl using a mixture containing 1× ExTaq Buffer (TaKaRa), 200 µM dNTPs (TaKaRa), 100 nM 454-A up forward PCR primer (5'-CCATCTCATC-CCTGCGTGTCCCATCTGTTCCCTCCCTG TCTCAG-3') (SEQ ID NO: 107), 100 nM reverse 454-B up biotinylated PCR primer (5'-Biotin-CCTATCCCCTGTGTGCCTTGC-CTATCCCCTGTTGCGTGTCTCAG-3') (SEQ ID NO: 108), and 5 units of ExTaq (TaKaRa) with the following PCR program 5 min at 94° C., 5 cycles×(30 s at 94° C., 30 s at 60° C., 2 min at 72° C.), 15 min at 72° C. and using hot start. PCR products were purified and concentrated by QIAGEN MinElute column (Qiagen) and analyzed on 1.5% agarose gel (FIG. 36).

For single strand DNA separation, PCR products were treated with 0.1N NaOH and single strand PCR products were binded to M-270 magnetic beads (invitrogen) and separated. Separated ssDNAs were purified by MinElute purification kit (Qiagen) and their elution volume was 15 µl. The purity and the concentration of the samples were analyzed with Agilent 2100 Bioanalyzer. The library (L1-6 and L1-13) were mixed each, and finally sequenced using FLX-454 sequencer.

Example 10

In this experiment, nuclear polyA– RNA, nuclear polyA+ RNA, cytoplasm polyA– RNA and cytoplasm polyA+ RNA from the K562 cell line were used to create CAGE tags by random priming.

Figure 37:
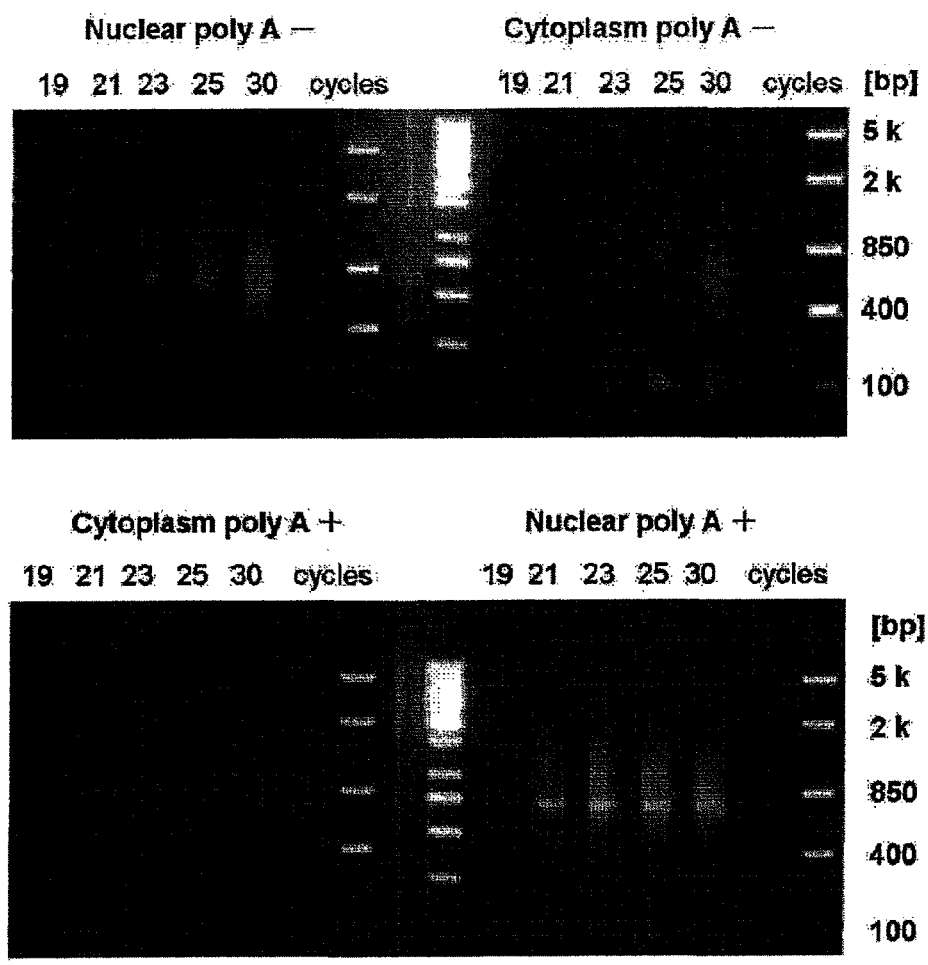
FIG. 37 shows the agarose gel analysis result of 1st PCR (moderately suppressive PCR) small scale carried out with Example 10.

The volume of water was reduced to 2 µl each by centrifugal evaporation at room temperature in the presence of 100 ng of RNA, 0.66 M D-Threalose (Nacalai Tesque), 3.3 M D-Sorbitol (WAKO), 100 µM of TS oligonucleotide (5'-TAGTC-GAACTGAAGGTCTCCAGCA(rG)(rG)(rG)-3') (SEQ ID NO:109), 10 µM of random RT primer (5'-TAGTCGAACT-GAAGGTCTCCGAACCGCTCTTCCGA TC-3' (SEQ ID NO: 110) was added to nuclear polyA– RNA, 5'-TAGTC-GAACTGAAGGTCTCCGAACCGCTCTTC-CGATCTCGANNNNNN-3' (SEQ ID NO: 111) was added to nuclear polyA+ RNA, 5'-TAGTCGAACTGAA GGTCTC-CGAACCGCTCTTCCGATCTATCNNNNNN-3' (SEQ ID NO: 112) was added to cytoplasm polyA– RNA and 5'-TAGTCGAACTGAAGGTCTCCGAACCGC TCTTC-CGATCTGC-3' 3' (SEQ ID NO: 113) was added to cytoplasm polyA+ RNA). The mixture was then heat-denatured at 65° C. for 10 min in a thermocycler (MWG) and transferred quickly on a ice/water mixture, to avoid the formation of secondary structures. Reverse transcription and template switching were accomplished together in a volume of 10.5 µl with the following components: 1.19× first strand buffer (Invitrogen), 595 µM dNTPs (TaKaRa), 1.24 mM DTT (Invitrogen), 881 mM betaine (Spiess and Ivell, 2002) (WAKO), and 200 units of SuperScriptII (Invitrogen). And they were incubated at 22° C. for 10 min, 50° C. for 30 min, 75° C. for 15 min in a MWG thermocycler. The tubes were then immediately transferred on ice/water mix. For the second strand synthesis a small scale moderately suppressive PCR reaction was performed to evaluate the optimal number of cycles, defined as the last cycle before the intensity of the product ceases to increase. 1 µl of first strand cDNA were amplified in a total volume of 100 µl using a mixture containing 1× ExTaq Buffer (TaKaRa), 200 µM dNTPs (TaKaRa), 1.0 µM forward PCR primer (5'-TAGTCGAACTGAAGGTCTCCAGC-3') (SEQ ID NO: 114), 1.0 µM reverse PCR primer (5'-TGACGTCGTCTAGTCGAACTGAAGGTCTCCG AACC-3') (SEQ ID NO: 115), and 5 units of ExTaq (TaKaRa) with the following PCR program 5 min at 95° C., n×(15 s at 95° C., 10 s at 65° C., 2 min at 68° C.), 00 at 4° C. and using hot start. 10 µl aliquotes were taken every two cycles and analyzed on 1.5 agarose gel. (FIG. 37). A large scale moderately suppressive PCR preparation using the first-strand cDNA was performed in 1 reaction of 100 µl. PCR products were pooled and cleaned using CTAB and GE Healthcare GFX purification columns.

Then PCR reaction was performed again. Optimal number of cycles for the PCR product to be amplified was determined by PCR with 1.0 µM of forward PCR primer (5'-AAT-GATACGGCGACCACCGAGATCTACAC-TAGTCGAACTGAAGG-3') (SEQ ID NO: 116), 1.0 µM of reverse PCR primer (5'-CAAGCAGAAGACGGCATAC-GAGATC GGTCTCGGCATTCCTGCTGAACCGCTCT-TCCGATCT-3') (SEQ ID NO: 117), 1× ExTaq buffer (TaKaRa), 200 µM dNTPs (TaKaRa), 2.5 units of ExTaq (TaKaRa) and 20 ng of PCR product in a total volume of 100 µl. The program was 5 min 95° C., 10 sec at 55° C., 2 min at 68° C., n×(15 sec at 95° C., 10 sec at 65° C., 2 min at 68° C.), 00 at 4° C. For the large-scale amplification, 5×50 µl of PCR were performed with 20 ng of PCR product in each tube. (FIG. 38). PCR products were mixed and the excess of the primers were removed by AMpure beads (Agencourt). And purification and separation were performed by 1.5% agarose gel (FIG. 39). The mixed sample was separated to 3 parts, which are short size, middle size and long size. After this, separated samples were sequenced with Solexa-GA2 PE.

Example 11

In this experiment, total RNA from HepG2 cell line (human) was used to create CAGE tags by random priming.

Reverse transcription reaction started by mixing 1 µg of RNA with 0.66 M D-Threalose (Nacalai Tesque), 3.3 M D-Sorbitol (WAKO), 100 µM of each TS oligonucleotide (5'-TAGTCGAACTGAAGGTCTCCAGCA(rG)(rG)(rG)-3'

Figure 40:
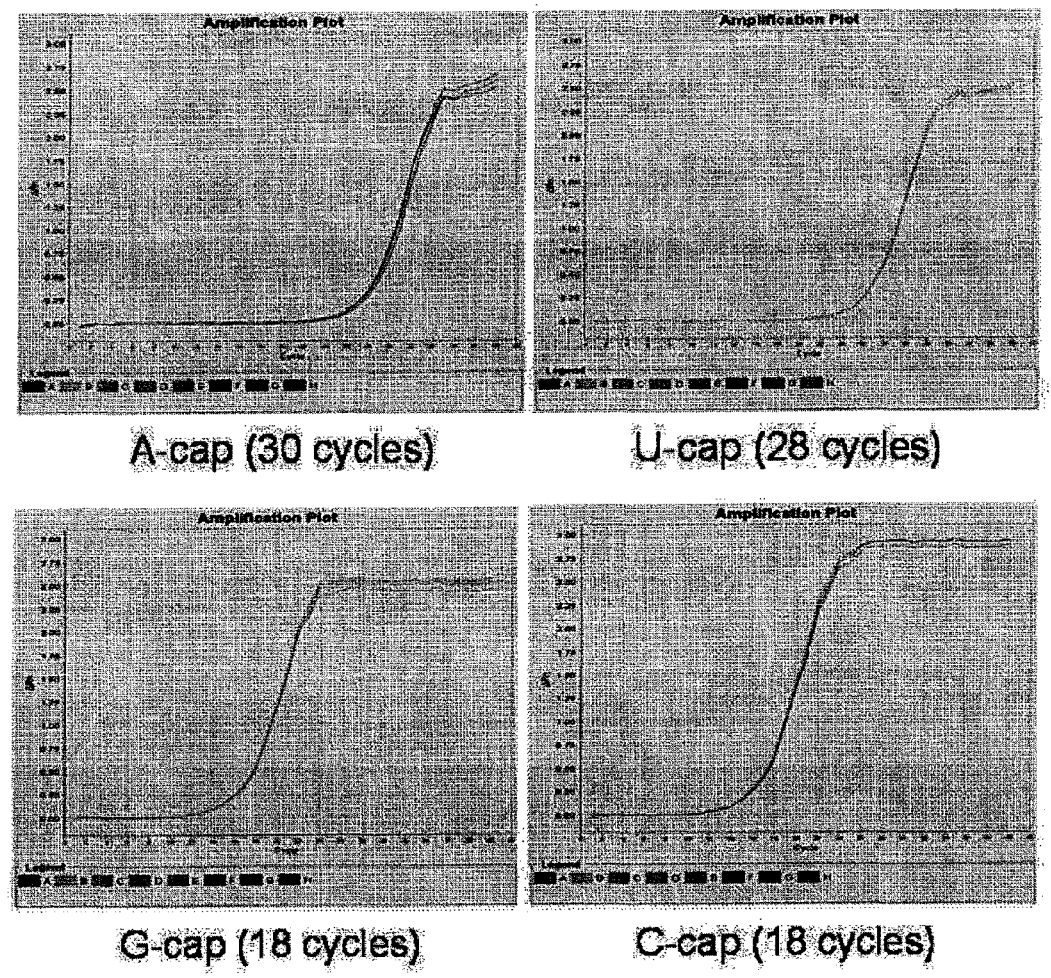
FIG. 40 shows the result of Real-time PCR carried out with Example 11.
Figure 41:
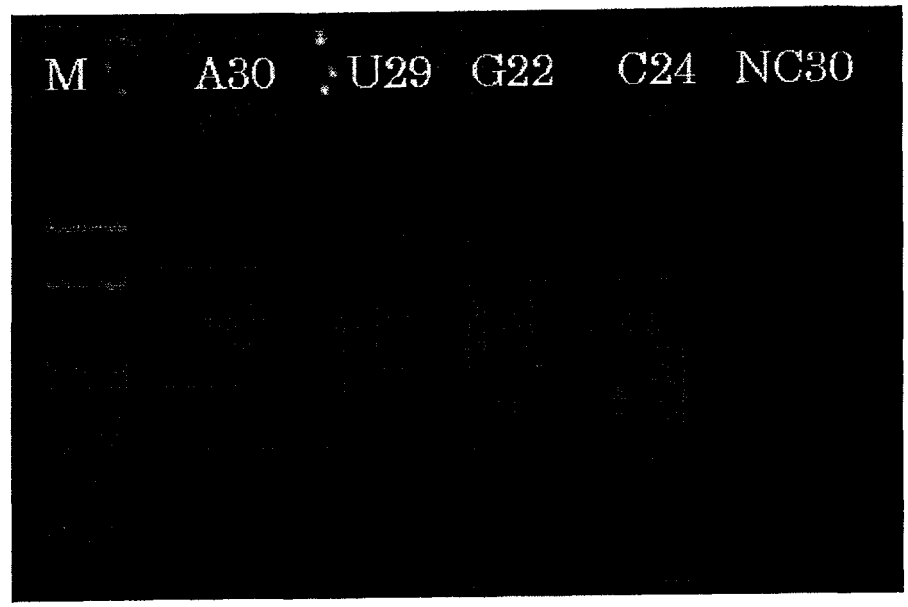
FIG. 41 shows the result of $1^{st}$ PCR (moderately suppressive PCR) large scale preparation using the first-strand cDNA carried out with Example 11.
Figure 42:
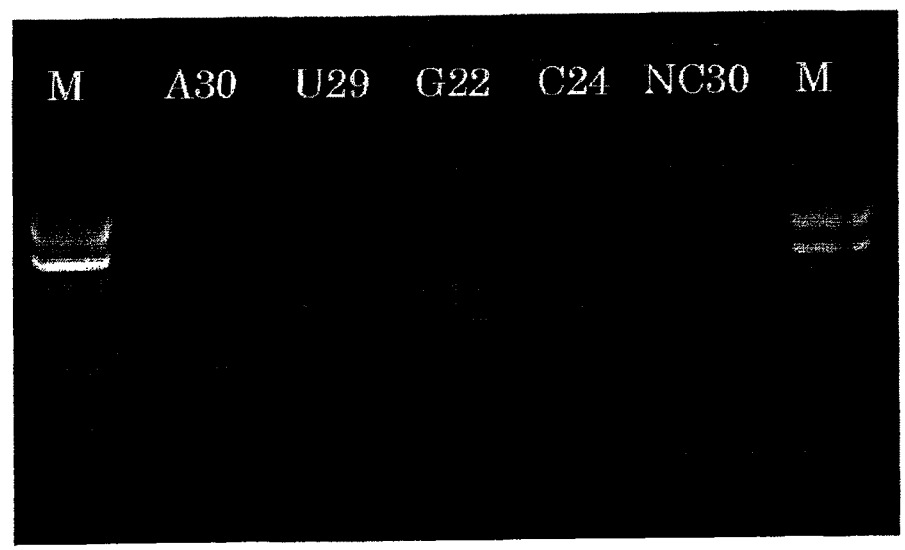
FIG. 42 shows the 1st PCR products (GFX-CTAB) after purification carried out with Example 11.

(SEQ ID NO: 118), 5'-TAGTCGAACTGAAGGTCTC-CAGCA(rA)(rA)(rA)-3' (SEQ ID NO: 119), 5'-TAGTC-GAACTGAAGGTCTCCAGCA(rC)(rC)(rC)-3' (SEQ ID NO: 120), and 5'-TAGTCGAACTGAAGGTCTCCAGCA (rU)(rU)(rU)-3' (SEQ ID NO: 121), wherein rA, rC and rU show riboadenosine, ribocytosine and ribouridine, respectively.) and 10 μM of random RT primer (5'-TAGTCGAACT-GAAGGTCTCCGAACCGCTCTTCCGATCT-3'(SEQ ID NO: 122). The volume of the each mixture was kept 2 μl by centrifugal evaporation and then heat-denatured at 65° C. for 10 min in a thermocycler (MWG) and transferred quickly on a ice/water mixture, to avoid the formation of secondary structures. Reverse transcription and template switching were accomplished together in a volume of 10.5 μl with the following components: 1.19× first strand buffer (Invitrogen), 595 μM dNTPs (TaKaRa), 1.24 mM DTT (Invitrogen), 881 mM betaine (Spiess and Ivell, 2002) (WAKO), and 200 units of SuperScript III (Invitrogen). And they were incubated at 22° C. for 10 min, 50° C. for 30 min, 75° C. for 15 min in a MWG thermocycler. The tubes were then immediately transferred on ice/water mix. To guess the optimum cycles, Realtime PCR was performed by using 1 μl of 5× diluted RT samples as template, forward PCR primer (5'-TAGTC-GAACTGAAGGTCTCCAGC-3') (SEQ ID NO: 123), reverse PCR primer (5'-TGACGTCGTCTAGTCGAACT-GAAGGTCTCCGAACC-3') (SEQ ID NO: 124) and SYBR Premix ExTaq (Perfect Real Time) (TAKARA) with attached protocol in Applied Bio-Systems StepOne Real Time PCR System (FIG. 40). Then the second strand synthesis a small scale moderately suppressive PCR reaction was performed to confirm the optimal number of cycles, defined as the last cycle before the intensity of the product ceases to increase. 1 μl of first strand cDNA were amplified in a total volume of 100 μl using a mixture containing 1× ExTaq Buffer (TaKaRa), 200 μM dNTPs (TaKaRa), 1.0 μM forward PCR primer (5'-TAGTCGAACTGAAGGTCTCCAGC-3') (nucleotides 1-23 of SEQ ID NO: 1), 1.0 μM reverse PCR primer (5'-TGACGTCGTCTAGTCGAA CTGAAGGTCTC-CGAACC-3') (SEQ ID NO: 126), and 5 units of ExTaq (TaKaRa) with the following PCR program 5 min at 95° C., n×(15 s at 95° C., 10 s at 65° C., 2 min at 68° C.), ∞ at 4° C. and using hot start. 5 μl aliquotes were taken every two cycles and analyzed on 1.5% agarose gel. A large scale moderately suppressive PCR preparation using the first-strand cDNA was performed in 2 reaction of 100 μl (FIG. 41). PCR products were pooled and cleaned using CTAB and GE Healthcare GFX purification columns and checked by 1.5 agarose gel (FIG. 42).

Figure 43:
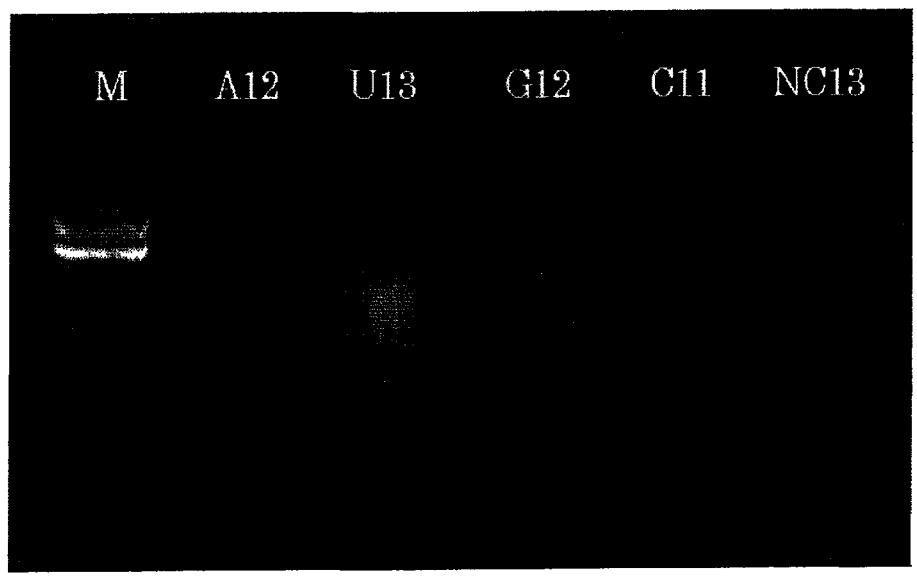
FIG. 43 shows the 2nd PCR products carried out with Example 11.
Figure 44:
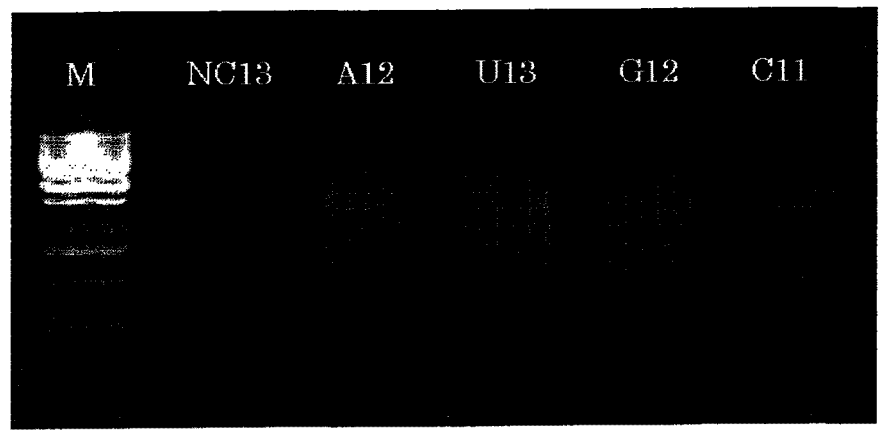
FIG. 44 shows the 2nd PCR products (AMpure) after purification carried out with Example 11.

To introduce solexa adaptors, PCR reaction was performed again. Optimal number of cycles for the PCR product to be amplified was determined by PCR with 1.0 μM of forward PCR primer (5'-AATGATACGGCGACCACCGAGATCTA-CACTAGTCGAAC TGAAGG-3') (SEQ ID NO: 127), 1.0 μM of reverse PCR primer (5'-CAAGCAGAAGACGGCAT-ACGAGATCGGTCTCGGCATTCCTGCTGAACCGCT CTTCCGATCT-3') (SEQ ID NO: 128), 1× ExTaq buffer (TaKaRa), 200 μM dNTPs (TaKaRa), 2.5 units of ExTaq (TaKaRa) and 20 ng of PCR product in a total volume of 50 lA The program was 5 min 95° C., 10 sec at 55° C., 2 min at 68° C., n×(15 sec at 95° C., 10 sec at 65° C., 2 min at 68° C.), co at 4° C. For the large-scale amplification, 2×100 μl of PCR were performed with 20 ng of PCR product in each tube (FIG. 43). The excess of the primers were removed by AMpure beads (Agencourt), and concentration of the amplified DNAs were measured by NanoDrop and checked by 1.5% agarose gel (FIG. 44). After this, all products were diluted to 10 nM solutions and mixed with equal volume. Then they were sequenced with Solexa sequencer.

Comparison of RT/Moderately Suppressive Primers

We tested four deletions and one random permutation (shuffle) of random RT primer to assess the moderately suppressive PCR protocol. Each of them had a corresponding reverse PCR primer.

50 ng of total RNA were heat-denatured at 65° C. for 10 min in a final volume of 2 μl with 50 μM of strand-switching oligonucleotide (5'-TAGTCGAACTGAAGGTCTCCAGCArGrGrG-3') (SEQ ID NO: 129) and 5 μM of random RT primer (N-15:5'-GTACCAGCAGTAGTCGAACTGAAG-GTCTCCTC N-3'(SEQ ID NO: 130), N-15-notail: 5'-TAGTCGAACTGAAGGTCTCCTC (SEQ ID NO: 131), N-15-del4:5'-GTACCAGCAGCGAACTGAAGGTCTC-CTC 3'(SEQ ID NO: 132), N-15-del8:5'-GTACCAGCAGCTGAAGGTCTCCTCT-NNNNNNN (SEQ ID NO: 133), N-15-shuffled:5'-CGTCATACCTCGGCACAATTGC-GATATCGGGT NNNNN-3') (SEQ ID NO: 134), (FIG. 45), in 264 μM D-Threalose (Nacalai Tesque) and 1.32 M D-Sorbitol (WAKO) and then transferred quickly on ice/water mix. RT was accomplished in a volume of 10.5 μl adding the following components to reach these final concentrations: 1.19× first strand buffer (Invitrogen), 595 μM dNTPs (TaKaRa), 1.24 mM DTT (Invitrogen), 881 mM betaine (WAKO) and 200 units of SuperScriptII (Invitrogen), and incubated at 22° C. for 10 min, 50° C. for 30 min, 75° C. for 15 min in a MWG thermocycler. The tubes were then immediately transferred on ice/water mix. For the second strand synthesis moderately suppressive PCR reaction was performed. 2 μl of first strand cDNA were amplified in a total volume of 100 μl using a mixture containing 1× ExTaq Buffer (TaKaRa), 200 μM dNTPs (TaKaRa), 100 nM forward PCR primer (5'-TAGTCGAACTGAAGGTCTCCAGC-3') (nucleotides 1-23 of SEQ ID NO: 135), 100 nM reverse PCR primer (N-15:5'-GTACCAGCAGTAGTCGAACTGAAG-GTCTCCTCT-3' (SEQ ID NO:136), N-15-notail: 5'-TAGTCGAACTGAAGGTCTCCTCT-3'(SEQ ID NO:137), N-15-del4: 5'-GTACCAGCAGCGAACTGAAG-GTCTCCTCT-3' (SEQ ID NO:138), N-15-del8:5'-GTAC-CAGCAGCTGAAGGTCTCCTCT-3' (nucleotides 1-25 of SEQ ID NO: 139), N-15-shuffled:5'-CGTCATACCTCG-GCACAATTGCGATATCGGGTA-3') (SEQ ID NO: 140) (FIG. 45), and 5 units of ExTaq (TaKaRa) with the following PCR program 5 min at 95° C., n×(15 s at 95° C., 10 s at 65° C., 2 min at 68° C.), 15 min at 68° C. and using hot start. 5 μl aliquotes were taken every cycles and analyzed on 1% agarose gel (FIG. 46).

From the result, removing the tail of N-15 weakened the moderately suppressive effect (signal appears in the negative control), but did not abolish it. Randomly permuting the sequence of N-15 completely abolished the moderately suppressive effect. So only very short molecules were amplified. Progressively shortening the common region (del4 and 8) had a drastic effect as strong as the randomisation.

Comparison of DNA TS Oligo

We tested a strand-switching oligonucleotide, which is a DNA oligonucleotide, to compare to a DNA/RNA hybrid where the last bases are riboguanosines.

50 ng of total RNA were heat-denatured at 65° C. for 10 min in a final volume of 2 μl with 50 μM of strand-switching oligonucleotide (DNA/RNA hybrid: 5'-TAGTCGAACT-GAAGGTCTCCAGCArGrGrG-3' (SEQ ID NO: 141), DNA/DNA 5'-TAGTCGAACTGAAGGTCTCCAG- CAGGG-3') (SEQ ID NO: 142) and 5 µM of random RT primer (5'-GTACCAGCAGTAGTCGAACTGAAG-GTCTCCTC-3') (SEQ ID NO: 143), in 264 µM D-Threalose (Nacalai Tesque) and 1.32 M D-Sorbitol (WAKO) and then transferred quickly on ice/water mix. RT was accomplished in a volume of 10.5 µl adding the following components to reach these final concentrations: 1.19× first strand buffer (Invitrogen), 595 µM dNTPs (TaKaRa), 1.24 mM DTT (Invitrogen), 881 mM betaine (WAKO) and 200 units of SuperScriptII (Invitrogen), and incubated at 22° C. for 10 min, 50° C. for 30 min, 75° C. for 15 min in a MWG thermocycler. The tubes were then immediately transferred on ice/water mix. For the second strand synthesis moderately suppressive PCR reaction was performed. 2 µl of first strand cDNA were amplified in a total volume of 100 µl using a mixture containing 1× ExTaq Buffer (TaKaRa), 200 µM dNTPs (TaKaRa), 100 nM forward PCR primer (5'-TAGTCGAACTGAAGGTCTC-CAGC-3') (SEQ ID NO: 144), 100 nM reverse PCR primer (5'-GTACCAGCAGTAGTCGAACTGAAGGTCTCCTCT-3') (SEQ ID NO: 145), and 5 units of ExTaq (TaKaRa) with the following PCR program 5 min at 95° C., n×(15 s at 95° C., 10 s at 65° C., 2 min at 68° C.), 15 min at 68° C. and using hot start. 5 µl aliquotes were taken every cycles and analyzed on 1% agarose gel (FIG. 47).

Surprisingly, the cDNAs looked almost as good if the strand-switching oligonucleotide was a DNA oligonucleotide when the last bases were guanosines, compared to a DNA/RNA hybrid where the last bases were riboguanosines.

REFERENCES

1. Yoshihide Hayashizaki, Piero Carninci, Claudio Schneider (2001). Method for making full-length cDNA libraries. U.S. Pat. No. 6,174,669.
2. Maruyama, K. & Sugano, S. (1994). *Gene* 138, 171-174.
3. Alex Chenchik, York Zhu, Luda Diatchenko, Paul Siebert (1999). Methods and compositions for full-length cDNA Cloning using a template-switching oligonucleotide. U.S. Pat. No. 5,962,272.
4. Hirzmann, J., Luo, D., Hahnen, J. & Hobom, G. (1993). *Nucleic Acids Res* 21, 3597-3598.
5. Ohtake, H., Ohtoko, K., Ishimaru, Y & Kato, S. (2004). *DNA Res* 11, 305-309.
6. Alex Chenchik, Luda Diatchenko, Paul Siebert, Sergey Lukianov, Konstantin Lukianov, Nadia Gurskaya, Victor Tarabykin, Eugene Sverdlov (1996). Method for suppressing DNA fragment amplification during PCR. U.S. Pat. No. 5,565,340.
7. Brownie J, Shawcross S, Theaker J, Whitcombe D, Ferrie R et al. (1997) The elimination of primer-dimer accumulation in PCR. Nucleic Acids Res 25: 3235-3241.
8. Shiraki, T., Kondo, S., Katayama, S., Waki, K., Kasukawa, T., Kawaji, H., Kodzius, R., Watahiki, A., Nakamura, M., Arakawa, T. et al. (2003). *Proc Natl Acad Sci USA* 100, 15776-15781.

The invention claimed is:

1. A method of manufacturing a mixture of amplified double-stranded nucleic acids comprising:
   (a) preparing a single-stranded nucleic acid comprising a single-stranded adapter 1, a single-stranded nucleic acid fragment and a single-stranded adapter 2,
      wherein said single-stranded adapter 1 comprises at least a common sequence 1 and a suffix sequence 1,
      said single-stranded adapter 2 comprises at least a suffix sequence 2 and a common sequence 2,
      wherein said common sequence 1 and said common sequence 2 are reverse-complementary, and
      said suffix sequence 1 and said suffix sequence 2 are not reverse-complementary; and
   (b) conducting PCR with said single-stranded nucleic acid prepared in step (a), a primer 1 comprising at least a part of the common sequence 1 and the suffix sequence 1, and a primer 2 comprising a part of the reverse-complement of the common sequence 2 and the reverse-complement of the suffix sequence 2 to amplify double-stranded nucleic acids,
wherein said step (a) comprises a nucleic acid strand synthesis reaction using a single-stranded template nucleic acid comprising a sequence complementary to the single-stranded nucleic acid fragment and comprising a cap structure or one or more extra 3'-ribonucleotide at 5' end thereof; an oligonucleotide comprising at 3' end thereof at least one nucleotide that can hybridize to extra 3'-nucleotides at 3' end of the single-stranded nucleic acid fragment, and a sequence reverse-complementary to the adapter 2; and a primer 3 comprising at least a random sequence or an oligo-T at 3' end thereof and a sequence corresponding to the adapter 1.

2. The method according to claim 1, wherein said adapter 1 further comprises a prefix sequence 1 at 5' end thereof and said primer 1 further comprises said prefix sequence 1 at 5' end thereof, or said primer 1 further comprises said prefix sequence 1 at 5' end thereof.

3. The method according to claim 1, wherein said adapter 2 further comprises a prefix sequence 2 at 3' end thereof and said primer 2 further comprises a sequence reverse-complementary to said prefix sequence 2 at 5' end thereof, or said primer 2 further comprises a sequence reverse-complementary to said prefix sequence 2 at 5' end thereof.

4. The method according to claim 1, wherein the single-stranded template nucleic acid is RNA and the nucleic acid strand synthesis reaction is reverse transcription reaction.

5. The method according to claim 1, wherein said common sequence 1 and said common sequence 2 comprise at least a restriction site, respectively.

6. The method according to claim 1, wherein the nucleotide length of said suffix sequence 1 and said suffix sequence 2 is 2 to 5 bases.

7. The method according to claim 1, wherein the nucleotide length of said common sequence 1 and said common sequence 2 is 15 to 30 bases.

8. The method according to claim 2, wherein the nucleotide length of said prefix sequence 1 is 8 to 15 bases.

9. The method according to claim 3, wherein the nucleotide length of said prefix sequences 2 is 8 to 15 bases.

10. The method according to claim 1, wherein each of the amplified double-stranded nucleic acids is a double-stranded cDNA comprising a sequence corresponding to a 5' end side sequence of RNA.

11. The method according to claim 4, wherein said single-stranded adapter 1 further comprises an extra sequence 1 at 3' end of the suffix sequence 1, and/or said single-stranded adapter 2 further comprises an extra sequence 2 at 5' end of the suffix sequence 2.

12. The method according to claim 11, wherein the nucleotide length of said extra sequence 1 is 15 to 30, and the nucleotide length of said extra sequence 2 is 15 to 30 bases.

* * * * *